United States Patent
Kanner et al.

(10) Patent No.: US 7,597,706 B2
(45) Date of Patent: Oct. 6, 2009

(54) ADVANCED WOUND SITE MANAGEMENT SYSTEMS AND METHODS

(75) Inventors: Glenn Kanner, Plymouth, MA (US); Kenneth Arden Eliasen, East Bridgewater, MA (US); Steven J. Tallarida, Mansfield, MA (US); Steve Bollinger, Mansfield, MA (US)

(73) Assignee: Medtronic Anqiolink, Inc., Santa Rosa, CA (US)

( * ) Notice: Subject to any disclaimer, the term of this patent is extended or adjusted under 35 U.S.C. 154(b) by 387 days.

(21) Appl. No.: 10/899,911

(22) Filed: Jul. 27, 2004

(65) Prior Publication Data

US 2004/0267312 A1 Dec. 30, 2004

Related U.S. Application Data

(63) Continuation of application No. 10/178,030, filed on Jun. 21, 2002, now Pat. No. 6,767,356, and a continuation-in-part of application No. 09/658,787, filed on Sep. 11, 2000, now Pat. No. 6,506,210.

(60) Provisional application No. 60/230,234, filed on Sep. 1, 2000.

(51) Int. Cl.
*A61B 17/064* (2006.01)

(52) U.S. Cl. ............... 606/219; 606/213; 227/175.1

(58) Field of Classification Search ........... 606/213, 606/215, 219, 220; 227/175.1, 181.1
See application file for complete search history.

(56) References Cited

U.S. PATENT DOCUMENTS

| | | | |
|---|---|---|---|
| 4,821,939 A | 4/1989 | Green | 227/19 |
| 4,887,601 A * | 12/1989 | Richards | 606/219 |
| 4,955,898 A | 9/1990 | Matsutani | 606/219 |
| 5,007,921 A | 4/1991 | Brown | 606/221 |
| 5,026,390 A | 6/1991 | Brown | 606/221 |
| 5,074,454 A | 12/1991 | Peters | 227/178 |
| 5,108,421 A | 4/1992 | Fowler | 606/213 |
| 5,115,958 A | 5/1992 | Petty | 227/180 |
| 5,129,570 A | 7/1992 | Schulze et al. | 227/19 |
| 5,158,567 A | 10/1992 | Green | 606/219 |
| 5,170,926 A | 12/1992 | Ruckdeschel et al. | 227/177 |
| 5,234,447 A * | 8/1993 | Kaster et al. | 606/153 |
| 5,251,801 A | 10/1993 | Ruckdeschel et al. | 227/177 |
| 5,297,714 A | 3/1994 | Kramer | 227/175 |
| 5,366,479 A * | 11/1994 | McGarry et al. | 606/219 |
| 5,392,978 A | 2/1995 | Velez et al. | 227/177 |
| 5,397,310 A | 3/1995 | Chu et al. | 604/158 |
| 5,413,584 A | 5/1995 | Schulze | 606/219 |

(Continued)

FOREIGN PATENT DOCUMENTS

EP 0656191 A2 6/1995

(Continued)

*Primary Examiner*—(Jackie) Tan-Uyen T Ho
*Assistant Examiner*—Christina Lauer

(57) ABSTRACT

A tissue staple that includes a pair of legs arranged generally parallel to one another connected by a pair of tabs. The tabs define an arc that extends distally from the proximal ends of the legs, and further define a slot between the tabs. The distal end of the leg may include a forked portion that defines two or more tissue piercing prongs. The location of the fork also may define a tissue stop. The legs may also include an indent that bends inwardly toward an indent formed on the other leg.

8 Claims, 55 Drawing Sheets

U.S. PATENT DOCUMENTS

| | | | | |
|---|---|---|---|---|
| 5,415,334 | A | 5/1995 | Williamson | 227/178 |
| 5,423,857 | A | 6/1995 | Rosenman et al. | 606/219 |
| 5,465,895 | A | 11/1995 | Knodel et al. | 227/176 |
| 5,478,354 | A | 12/1995 | Tovey et al. | 606/219 |
| 5,496,332 | A | 3/1996 | Sierra et al. | 606/139 |
| 5,507,776 | A | 4/1996 | Hempel | 606/219 |
| 5,540,375 | A | 7/1996 | Bolanos et al. | 227/178.1 |
| 5,544,802 | A | 8/1996 | Crainich | 227/176 |
| 5,584,856 | A | 12/1996 | Jameel et al. | 606/220 |
| 5,610,251 | A * | 3/1997 | Kneafsey et al. | 526/264 |
| 5,630,540 | A | 5/1997 | Blewett | 227/176 |
| 5,630,541 | A | 5/1997 | Williamson, IV et al. | 227/178.1 |
| 5,645,567 | A * | 7/1997 | Crainich | 606/219 |
| 5,690,269 | A | 11/1997 | Bolanos et al. | 227/176.1 |
| 5,695,524 | A | 12/1997 | Kelley et al. | |
| 5,725,554 | A * | 3/1998 | Simon et al. | 606/219 |
| 5,738,474 | A | 4/1998 | Blewett | 411/473 |
| 5,779,132 | A | 7/1998 | Knodel et al. | 227/176.1 |
| 5,810,846 | A | 9/1998 | Virnich et al. | 606/142 |
| 5,871,135 | A | 2/1999 | Williamson, IV et al. | 227/178.1 |
| 5,919,207 | A | 7/1999 | Taheri | 606/219 |
| 5,941,890 | A * | 8/1999 | Voegele et al. | 606/151 |
| 6,004,341 | A | 12/1999 | Zhu et al. | 606/198 |
| 6,015,417 | A | 1/2000 | Reynolds, Jr. | 606/151 |
| 6,149,658 | A | 11/2000 | Gardiner et al. | 606/139 |
| 6,197,042 | B1 | 3/2001 | Ginn et al. | 606/213 |
| 6,368,341 | B1 | 4/2002 | Abrahamson | 606/213 |
| 6,391,048 | B1 | 5/2002 | Ginn et al. | 606/213 |
| 6,461,364 | B1 | 10/2002 | Ginn et al. | 606/142 |
| 2002/0026208 | A1 | 2/2002 | Roe et al. | 606/190 |

FOREIGN PATENT DOCUMENTS

| | | | |
|---|---|---|---|
| EP | 0955011 A1 | 11/1999 | |
| GB | 2069650 | 8/1981 | |
| WO | WO 02/19920 A1 | 3/2002 | 17/64 |
| WO | WO 02/19922 A1 | 3/2002 | 17/68 |

* cited by examiner $F_1$

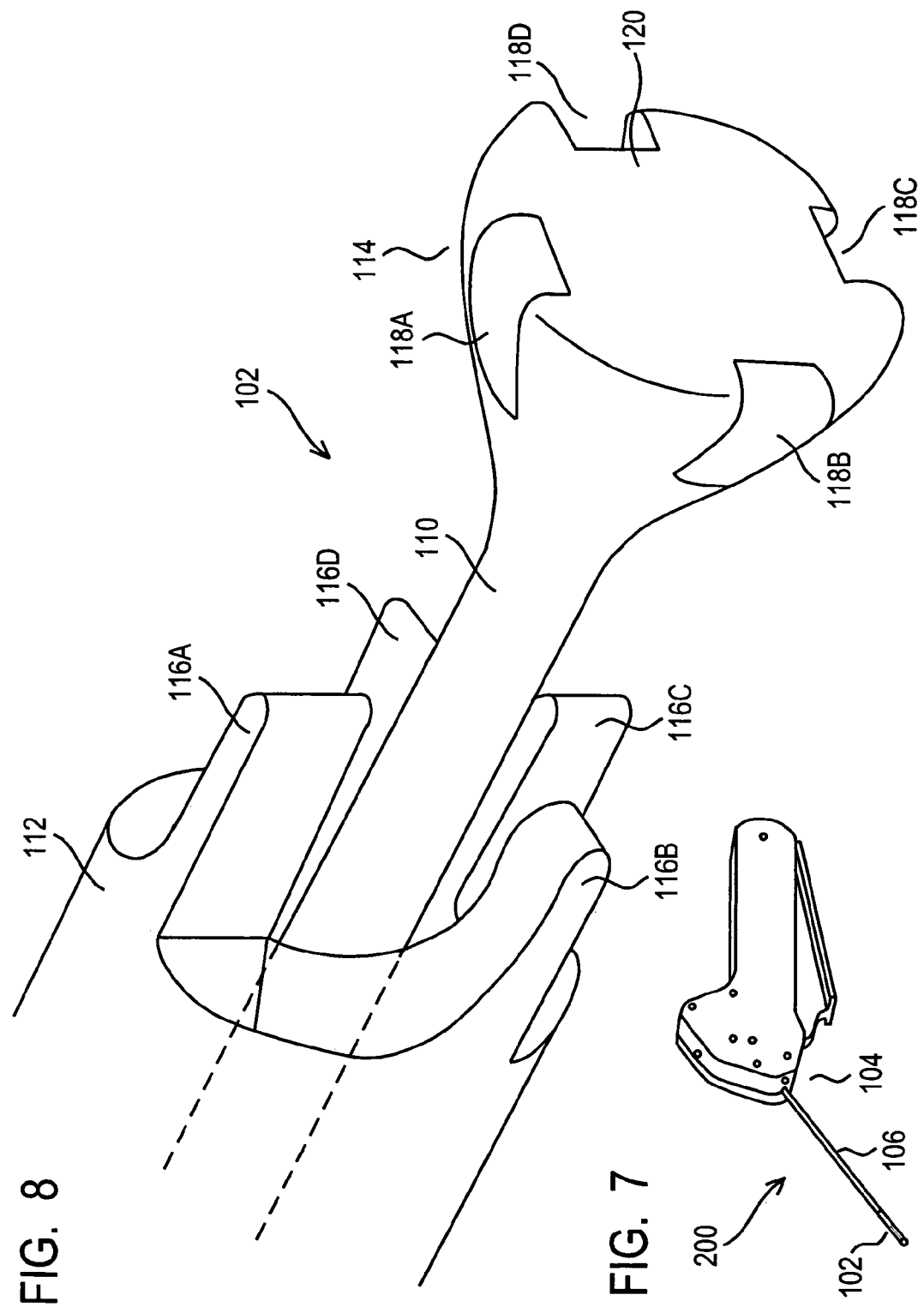

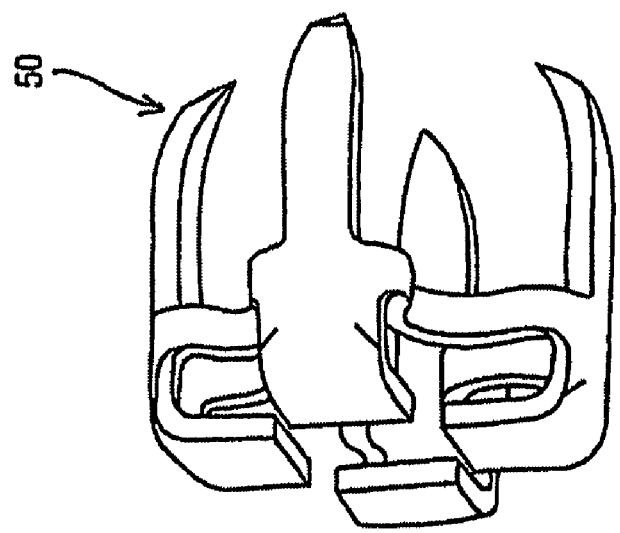
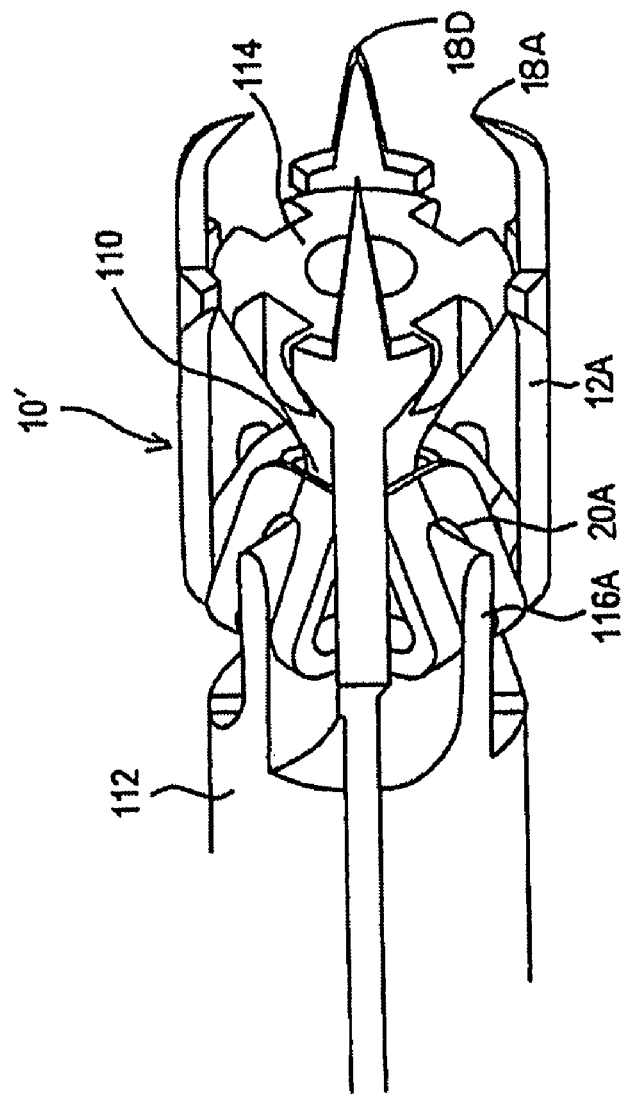
FIG. 9B
FIG. 9A

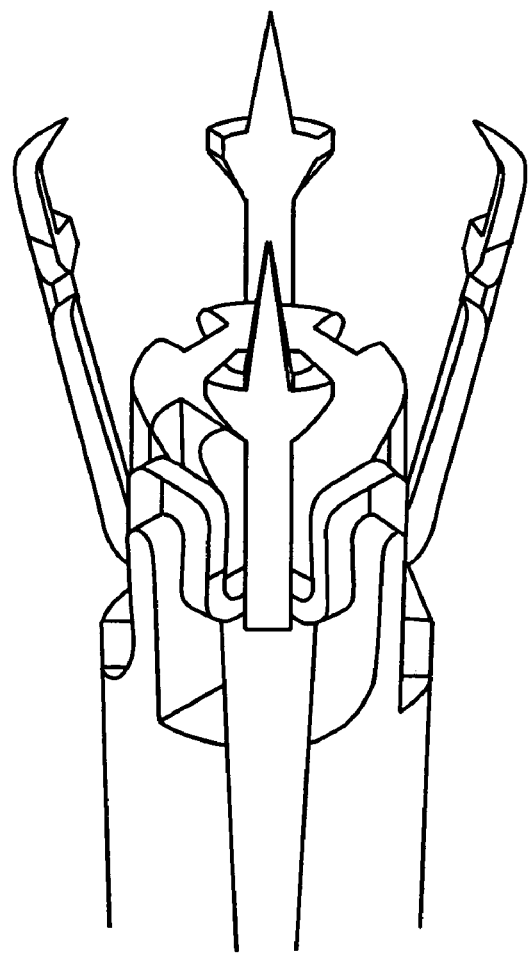
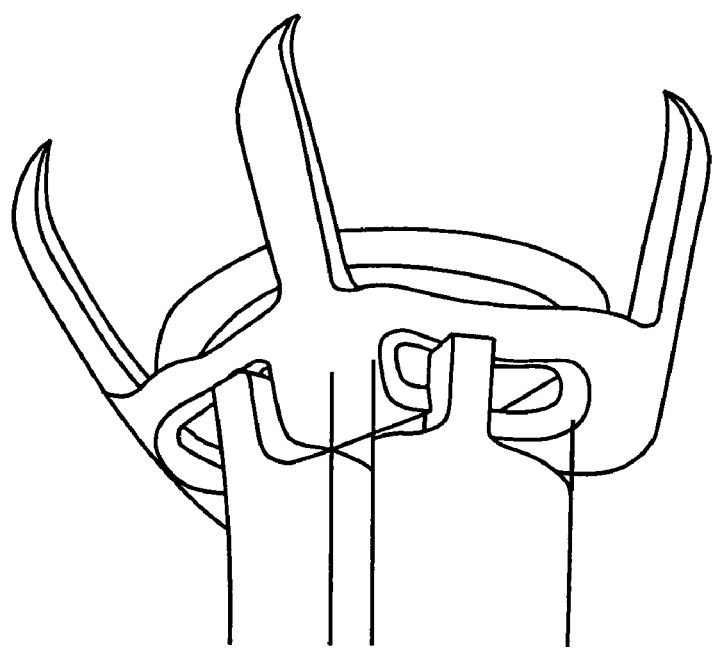
FIG. 10A
FIG. 10B

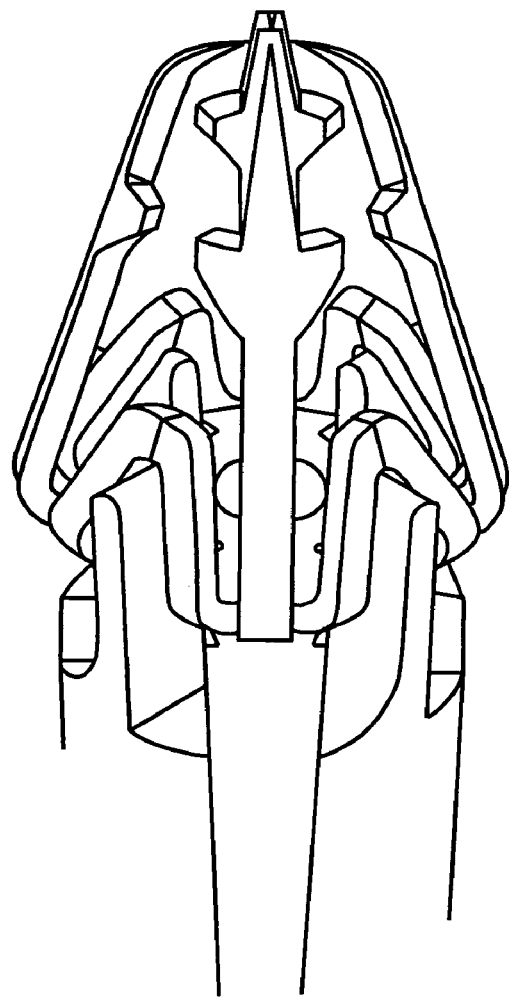
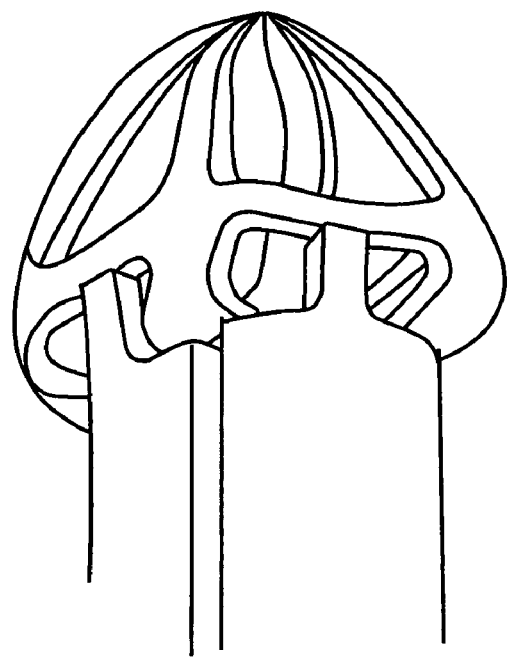
FIG. 11A
FIG. 11B

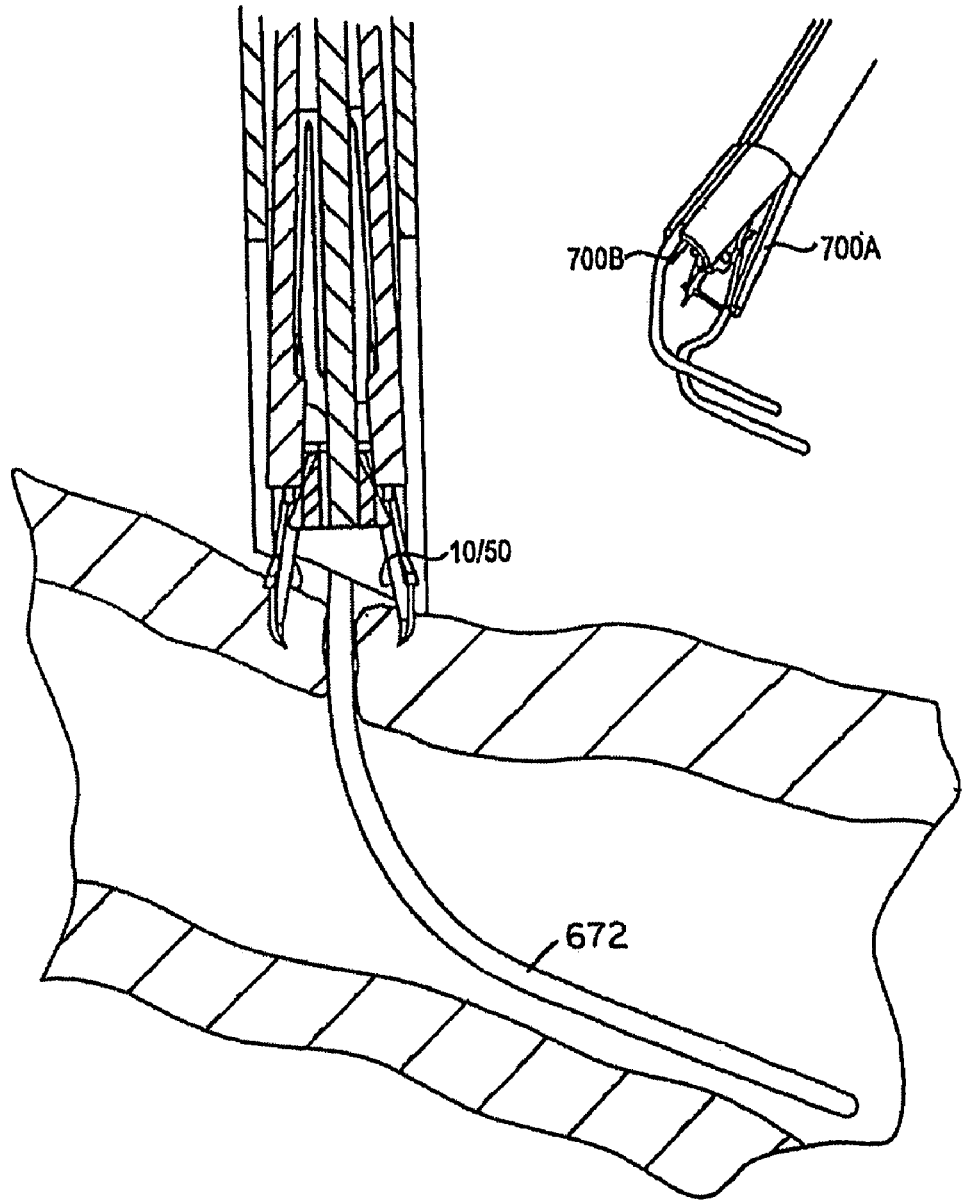

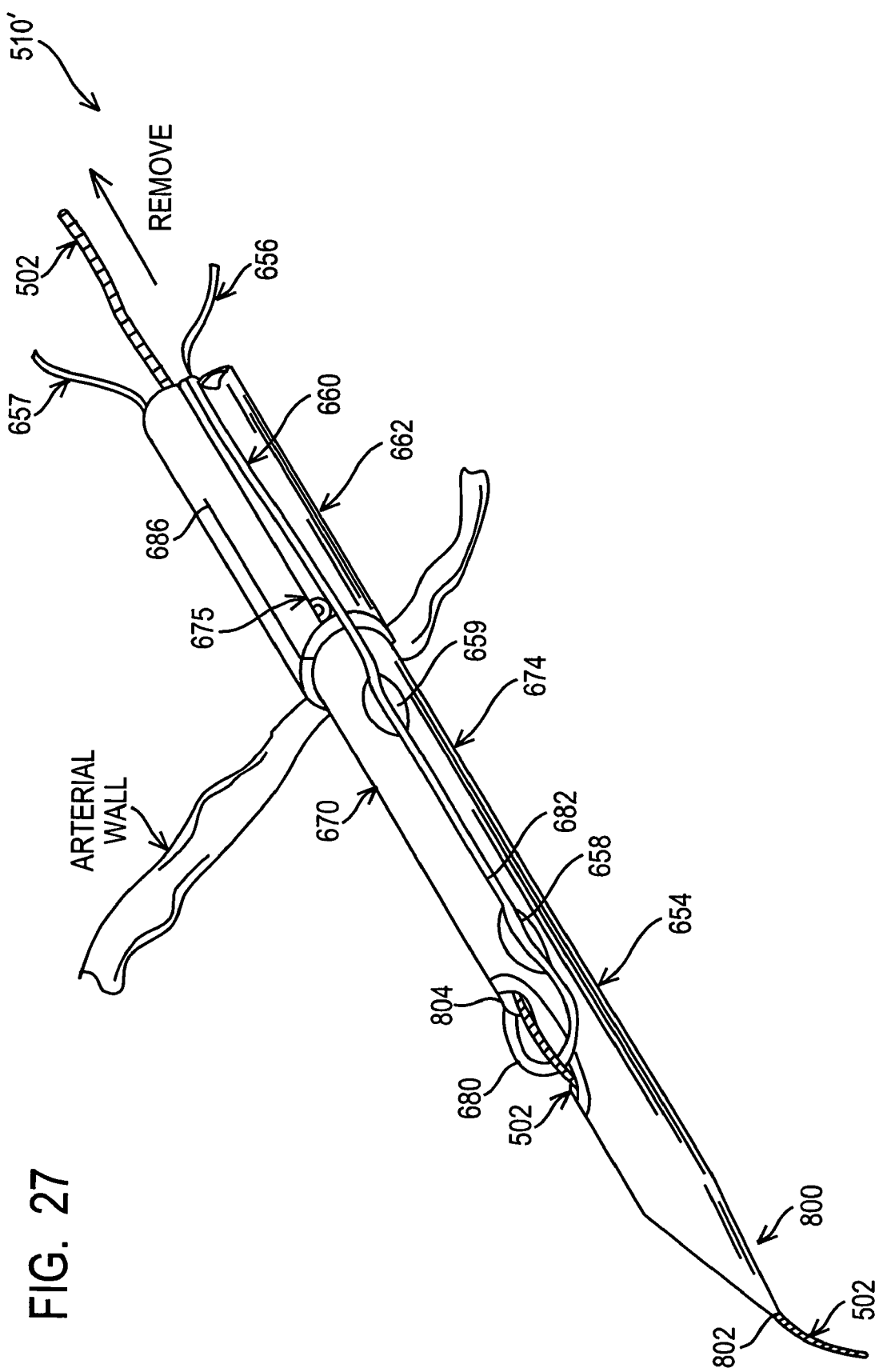

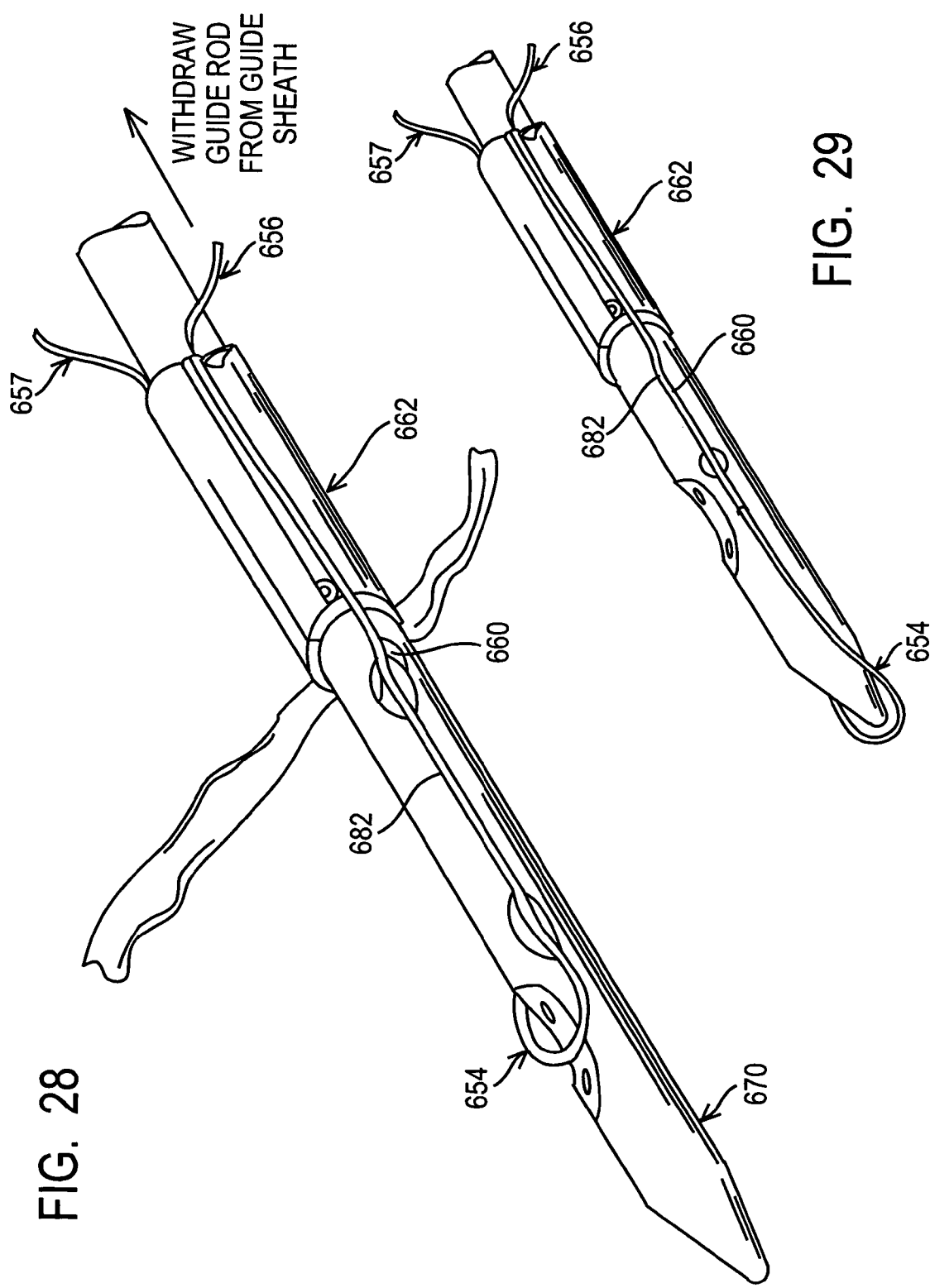

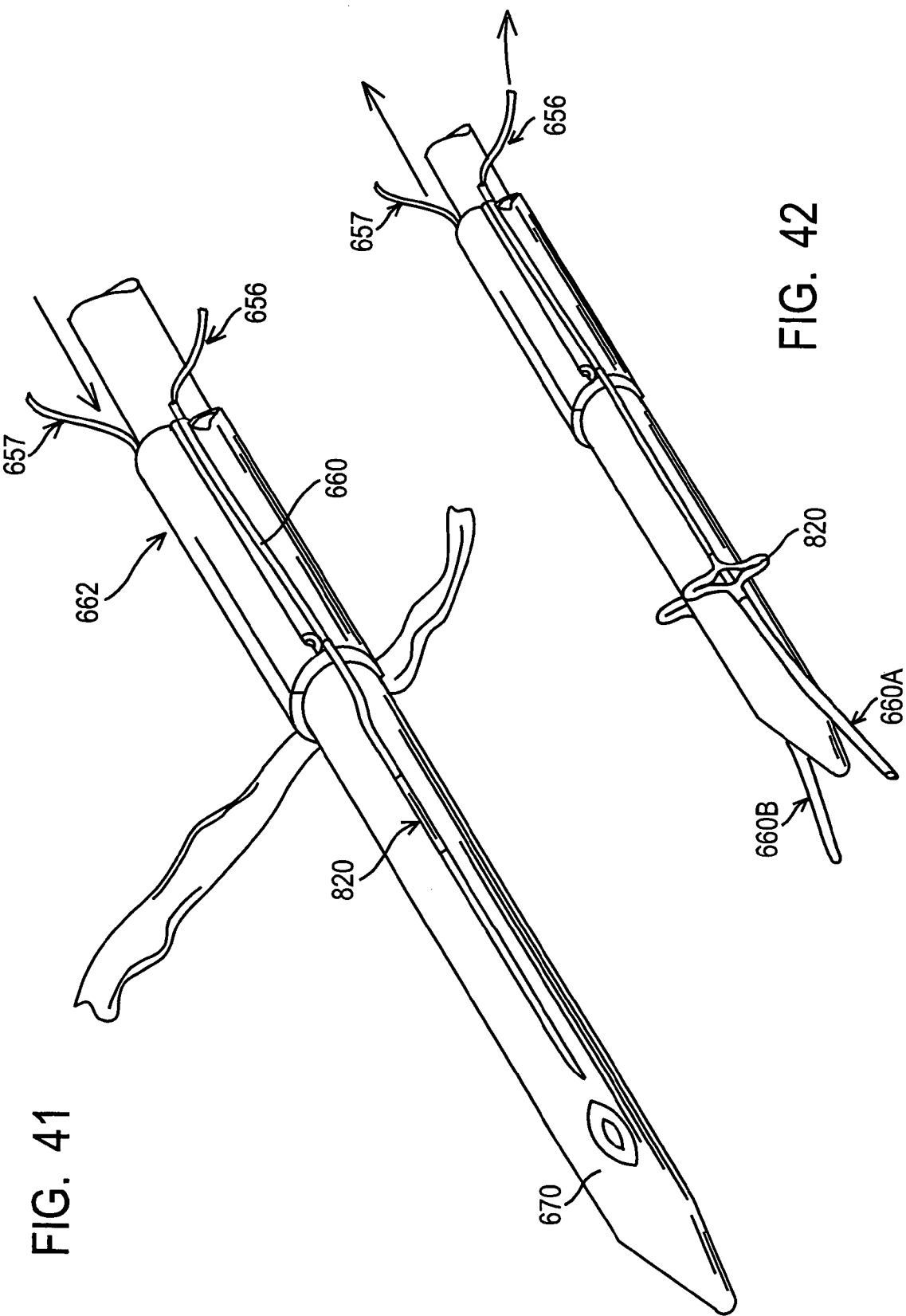

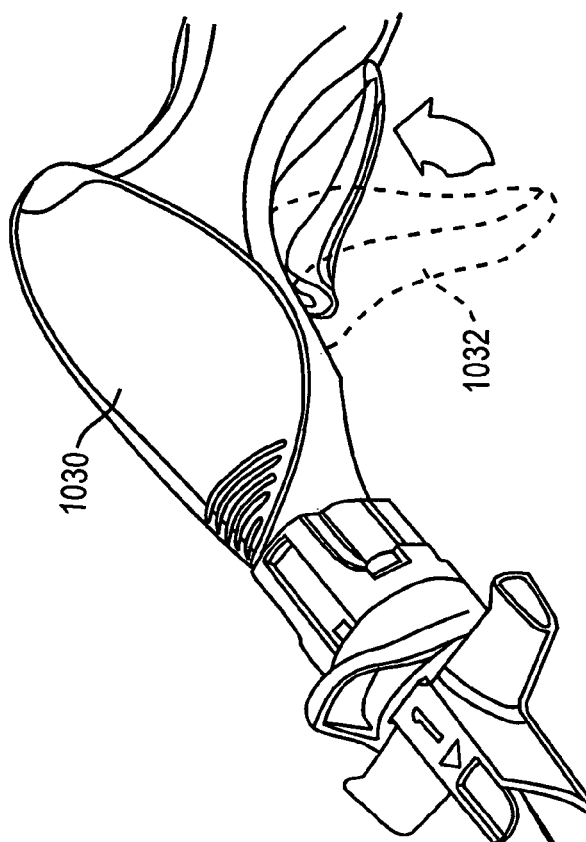
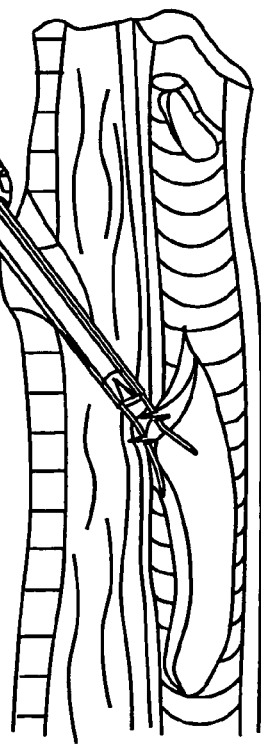
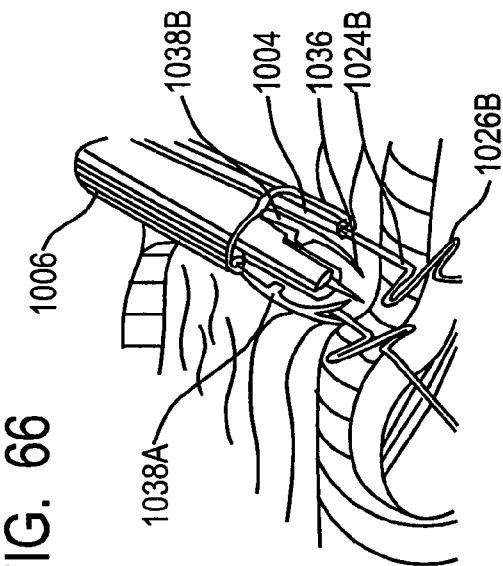
FIG. 65
FIG. 66

ADVANCED WOUND SITE MANAGEMENT SYSTEMS AND METHODS

CROSS-REFERENCE TO RELATED APPLICATIONS

The present invention is a continuation of application Ser. No. 10/178,030, fled Jun. 21, 2002, now U.S. Pat. No. 6,767, 356; and a continuation-in-part of application Ser. No. 09/658,787, filed Sep. 11, 2000, now U.S. Pat. No. 6,506,210; which claims benefit of U.S. provisional application Ser. No. 60/230,234 filed Sep. 1, 2000; assigned to the same assignee, and hereby incorporated by reference in its entirety.

BACKGROUND OF THE INVENTION

1. Field of the Invention

The present invention relates to a wound site management, for use during and after an invasive medical procedure. More specifically, the present invention relates to wound site management techniques and methodology for diagnostic and interventional procedures occurring at a wound site, for example, a puncture made in the wall of an artery or vein during a medical procedure. The puncture may be the result of a catheter-based intervention, although any puncture is contemplated, accidental or intentional. The present invention has particular utility for use in and around the femoral, radial, and brachial arteries after coronary/cardiac procedures. Other utilities include soft-tissue anchoring, tendon and artery joining, vessel anastomosis, meniscal repair, thoracic lung closure, heart repair, endoscopic procedures, esophageal repair, laparoscopy, skin/epidermal wound closure and general tissue closure.

2. Description of Related Art

Catheters/catheterization procedures are well known, and typically involve insertions through the femoral artery for diagnosis or to treat cardiovascular and/or peripheral vascular diseases. After a diagnostic or interventional catheterization, the puncture formed by the catheter must be closed. The puncture opening in the artery typically ranges from 5F for a diagnostic procedure to 610F for an interventional procedure. Traditionally, intense pressure has been applied to the puncture site for at least 30-45 minutes after removal of the catheter. Other approaches include the use of a thrombotic or collagen plug or slurry, and/orother suturing methodologies for sealing the puncture. Patients who have had a femoral puncture are then required to remain at bed rest, essentially motionless and often with a heavy sandbag placed on their upper legs, for several hours to ensure that the bleeding has stopped. This traditional method of hemostasis following femoral artery access has many inadequacies. When a blockage is removed during a procedure, the patient quickly feels better and they often have more energy than they have had in years, but they must remain motionless for several hours. The weight of the sandbag on the femoral artery often causes the lower leg to tingle or go numb. The recovery time from the medical procedure may be as little as ½ hour, but the recovery time from the wound can exceed 24 hours. The longer the recovery time, the more expensive the procedure becomes, the greater the patient discomfort, and the greater the risk of complications.

BRIEF DESCRIPTION OF THE DRAWINGS

It will be appreciated by those skilled in the art that although the following Detailed Description will proceed with reference being made to preferred embodiments the present invention is not intended to be limited to these preferred embodiments. Other features and advantages of the present invention will become apparent as the following Detailed Description proceeds, and upon reference to the Drawings, wherein like numerals depict like parts, and wherein:

FIG. 7 depicts one embodiment of the stapler of the present invention;

FIG. 8 is an isometric view of the distal tip of the stapler of FIG. 7 adapted to hold and deploy the staple of FIGS. 1-6;

FIGS. 9A-11B are isometric views of the cooperative movement of the distal tip of the stapler and the staple of the present invention;

FIGS. 18-26 depict various views of a first exemplary introducer of the present invention;

FIGS. 27-32, 39 and 39A depict various views of a second exemplary introducer of the present invention;

FIGS. 40-59 depict a fourth exemplary introducer of the present invention; and FIGS. 60-66 depict a fifth exemplary introducer of the present invention.

DETAILED DESCRIPTION OF THE INVENTION

Tissue Staple

In one aspect of the present invention, a staple is provided to close a tissue wound after a medical procedure. Although the preferred use of the staple of the present invention is to close an artery or vein following a diagnostic or interventional procedure, it should be recognized at the outset that the staple may be used for general tissue repair, not just limited to vascular repair. It will be appreciated throughout the following description that the staple of the present invention can be formed of any biocompatible and/or bioabsorbable materials, including, for example, Titanium (and Titanium alloys), stainless steel, polymeric materials (synthetic and/or natural), ceramic, etc. It will also be apparent from the following description that the staple of the present invention is preferably formed of a deformable material (such as those listed above) that undergoes plastic deformation (i.e., deformation with negligible elastic component.) As a general overview, the staple of the present invention undergoes two positions of deformation: a first position to extend the distal ends of the prongs of the staple outwardly to grab a greater amount of tissue (and also to grab tissue away from the wound locus), and a second position to move the prongs inwardly to close the wound.

Figure 1:
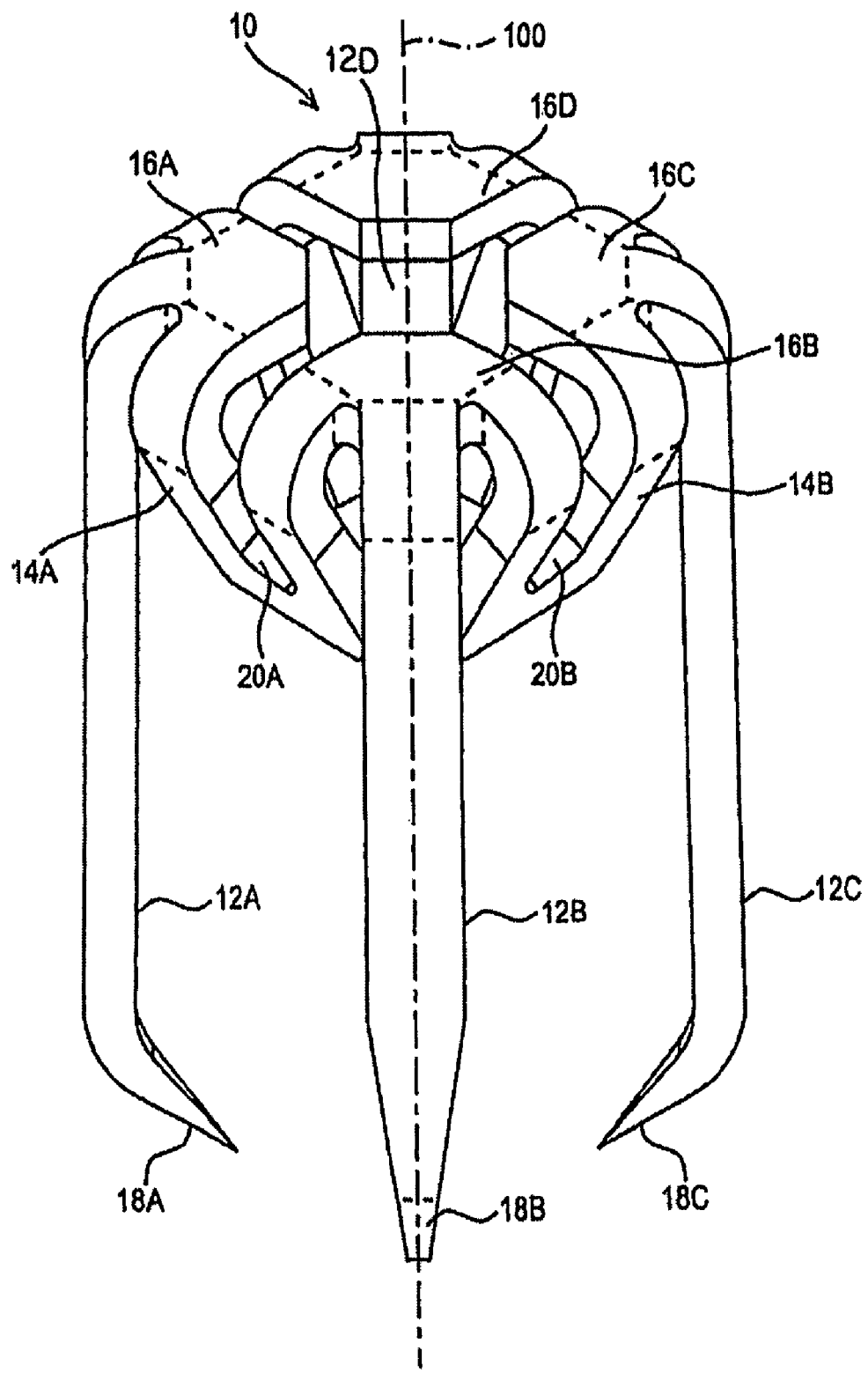
FIGS. 1-3 are isometric views of one embodiment of the staple of the present invention in formed, opened and deployed positions, respectively.
Figure 2:
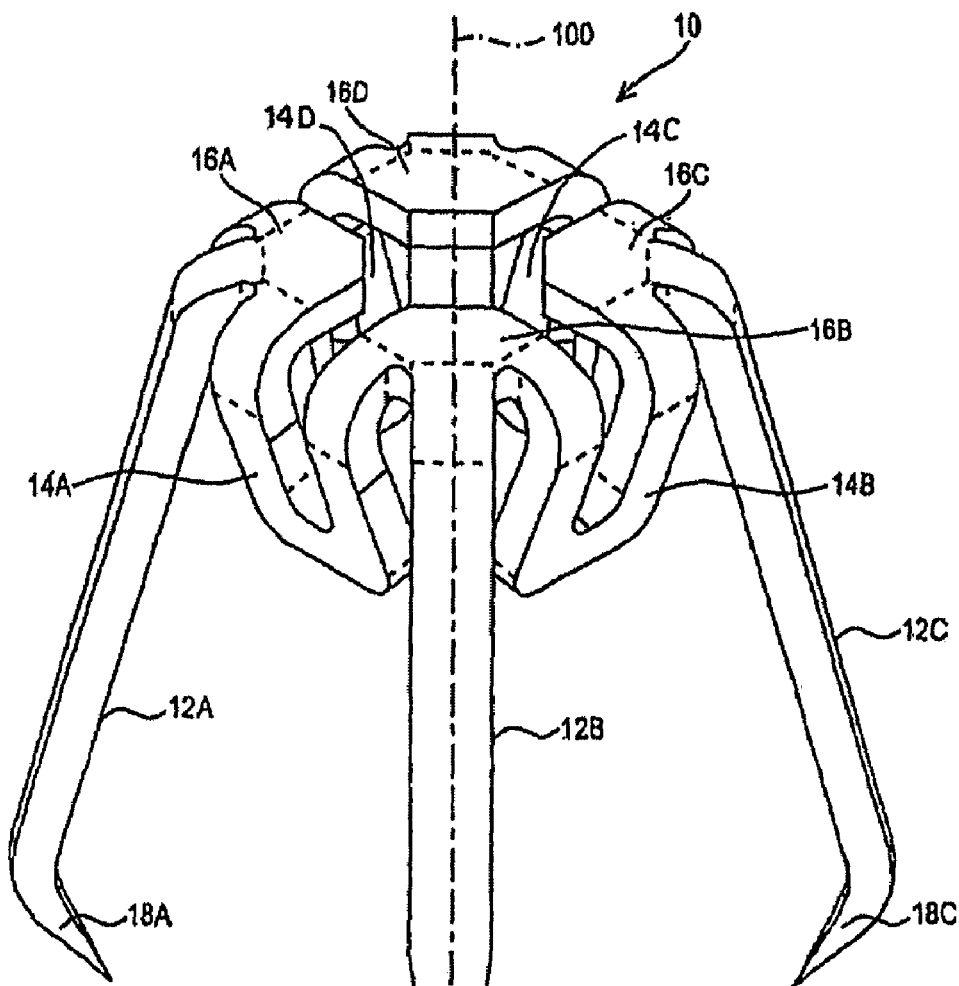
Figure 3:
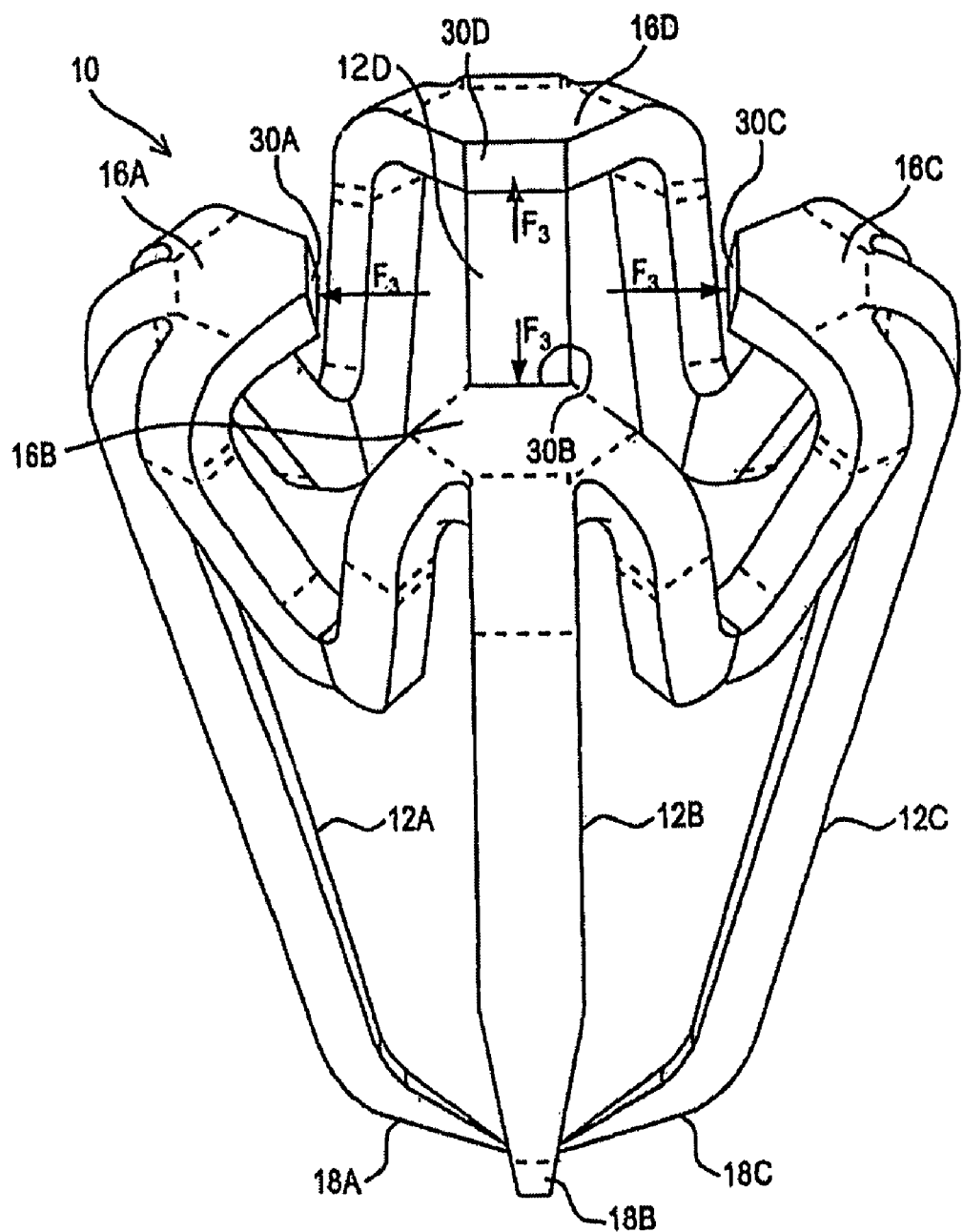

FIGS. 1, 2 and 3 depict one embodiment of staple 10 of the present invention. FIG. 1 is the staple in it's formed position, FIG. 2 is the staple just prior to deployment into tissue with the prongs extended outwardly, and FIG. 3 is the staple closed around tissue. The staple 10 of this embodiment comprises a plurality of prongs 12A-12D and a plurality of tabs 14A-14D, arranged about a centerline axis 100. Common portions, or shoulders 16A-16D are formed where the tabs meet the prongs. Each shoulder is common to both the prong and the tab and is generally defined by a relatively flat portion generally orthogonal to the centerline axis. Shoulders 16A-16D may be viewed as an extension of each prong, bent inwardly toward the centerline axis. Each of these features of the staple 10 of this embodiment is detailed below.

In the formed position (FIG. 1), prongs 12A-12D extend generally parallel to central axis 100, as shown. At the distal end of each prong, tapered points 18A-18D is formed to extend inwardly toward the centerline axis 100. At the proximal end, shoulders 16A-16D meet at prongs 12A-12D, respectively. Tabs 14A-14D are generally U-shaped, and are formed between each prong. The proximal portions of each tab are joined at consecutive shoulders, as shown. Each proximal portion of the U (i.e., each "leg" of the U-shape tab) extends first generally outward from the shoulder, and second bends inwardly and distally toward centerline axis 1100, connecting together nearest the centerline axis to form the U shape. The U-shape defines slots 20A-20D within each tab having a base positioned at the bottom thereof.

Figure 2A:
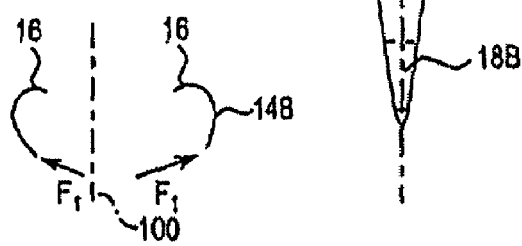

Referring specifically to FIG. 2, the staple 10 is deformed so that prongs 12A-12D extend outwardly from the centerline axis, prior to deployment into tissue. It is advantageous to extend the prongs outwardly as shown so as to grasp a large portion of tissue, and so that insertion of the prongs into the tissue occurs at a locus away from the wound site, thereby providing a more consistent wound closure (by closing the wound with more of the surrounding tissue) and ensuring complete (or near complete) closure of the wound. To deform the staple into the position shown in FIG. 2, a force $F_1$ is applied to tabs 14A-14D, as shown in relief in FIG. 2A. Force $F_1$ is generally outward (from the centerline axis) and proximal to the top of the staple, as shown in relief in FIG. 2A. This force causes the tabs to move outward from the centerline axis 1100. The outward movement of the tabs causes the shoulder portions to pivot roughly about the juncture between the shoulder and the prong (i.e., at the outer portion of the shoulder), causing the inner portions of the shoulders to move inwardly toward the centerline axis and distally. Since the prongs are attached to the outer portion of the shoulders, the movement of the shoulders in this manner causes the prongs to move outwardly. Thus, the cross-sectional diameter of the staple gets larger at the distal end (with respect to the cross-sectional diameter of the formed staple of FIG. 1). Note that the movement of the prongs is generally greater at the distal portions thereof than at the proximal portions thereof. In other words, movement of the prongs as shown in FIG. 2 is pivoted from the shoulder, thus producing a staple with outwardly extending prongs. For completeness, it should be noted that a holding force may be applied downwardly (i.e., substantially parallel to the centerline axis) against the base of the slots 20A-20D to hold the staple in place. Also, it is preferred that these forces are simultaneously applied to each tab of the staple to produce uniform deformation of each prong of the staple. As mentioned above, it is preferable that the plastic deformation of the staple is semi-permanent, so that the staple does not tend to return to the shape depicted in FIG. 1 (i.e., non-elastic deformation). Deformation of the staple into this position will be described in greater detail below in reference to the preferred stapler device of the present invention.

FIG. 3 depicts the staple 10 in a closed position. The closed position, as stated herein generally means that the prongs of the staple are moved inwardly toward each other. Although FIG. 3 depicts the tapered-tip portions of the prongs meeting generally in the vicinity of the centerline axis, however, it should be understood that the term "closed" or "deployed" as used in reference to the staple need not necessarily mean this precise configuration. It maybe required (or desirable) for some procedures to move the prongs inwardly toward each other to a greater or lesser extent than as depicted in FIG. 3. To draw the staple into the closed position depicted in this Figure, a force $F_3$ is applied to the inner surfaces 30A-30D of the shoulders. This force is generally orthogonal to the centerline axis, and the angle between each force approximates the angle between the inner surfaces 30A-30D (which, in the staple of this embodiment is approximately 90 degrees). This force causes the slots 20A-20D to spread apart and urges the shoulders outwardly. Movement in this manner also causes the shoulders to move outwardly and proximally. Proximal movement of the shoulders causes the prongs to move toward each other. Opposite to the movement of FIG. 2, deformation shown in FIG. 3 results in an expanded cross-sectional diameter of the proximal end of staple, and a diminished cross-sectional diameter of the distal end of the staple (with respect to the formed staple of FIG. 1 and the deformed staple of FIG. 2). Again, deformation of the staple 10 into this position will be described in greater detail below in reference to the preferred stapler device of the present invention.

For certain tissue application, it may be desirable that the staple of the present invention is deployed into tissue such that the prongs do not fully pierce through the tissue, but rather grasp and hold the tissue together. For example, for vascular closure applications it may be desirable that the tissue piercing tapered ends not enter the bloodstream, but rather pierce into the tissue and stop short of piercing through the tissue wall. To that end, and referring to FIG. 3A, the staple 10' of the present invention can be adapted with tissue stops 32A-32D. Preferably, tissue stops 32A-32D are located along the length of each prong, and positioned from the distal tip of the prong to permit the tapered ends to pierce tissue, but not pierce all the way through the tissue. Accordingly, the position of the stops 32A-32D along the length of the prongs is selected to facilitate tissue grabbing (but not complete tissue piercing) and can vary from application to application.

Figure 4:
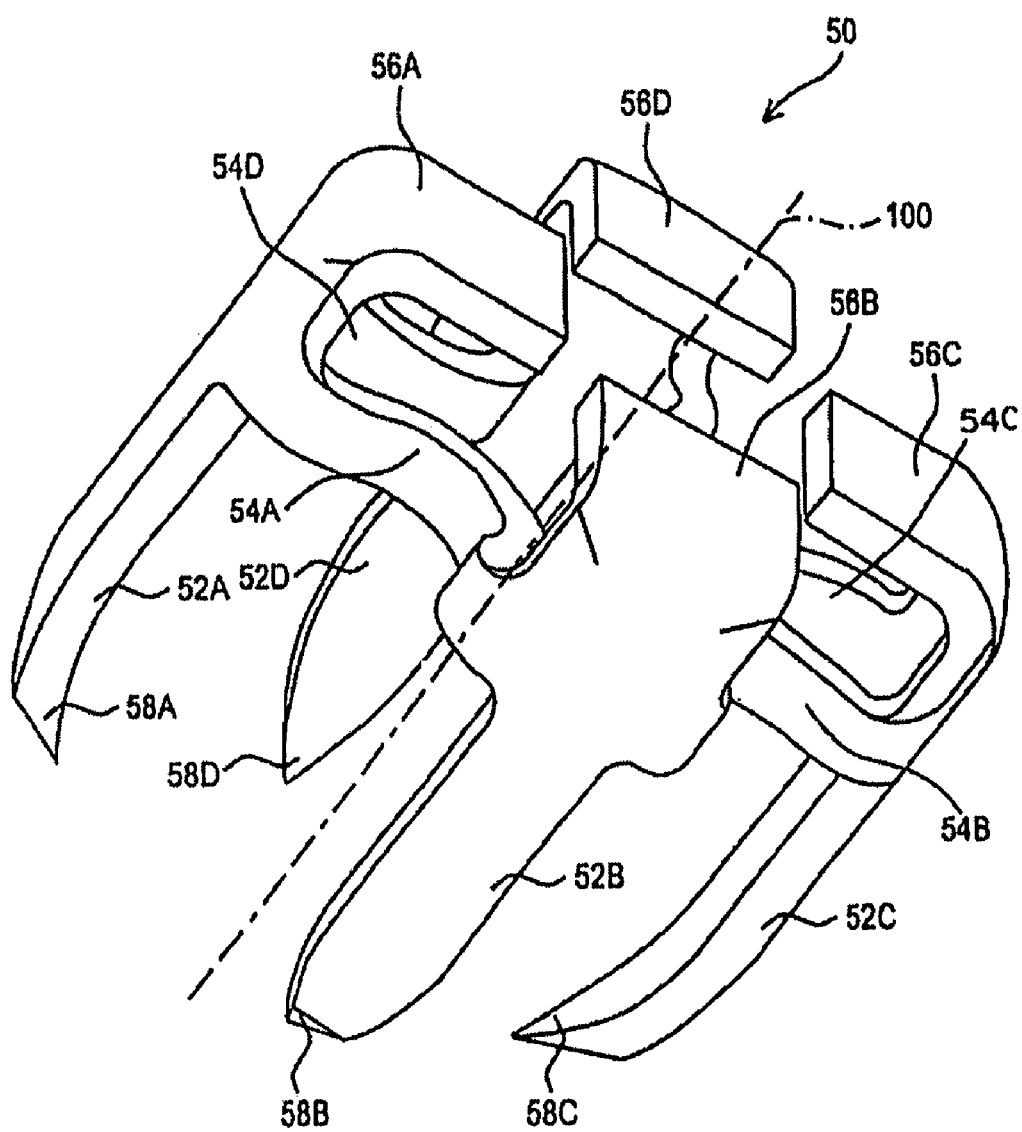
FIGS. 4-6 are isometric views of another embodiment of the staple of the present invention in formed, opened and deployed positions, respectively.
Figure 5:
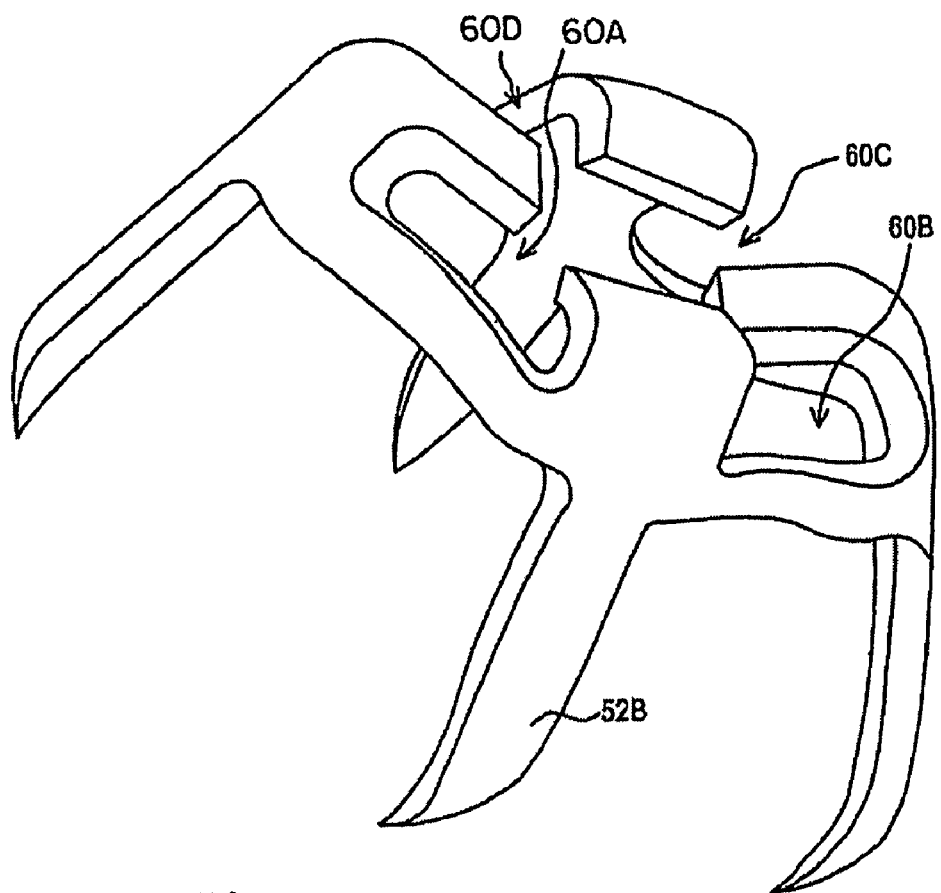
Figure 6:
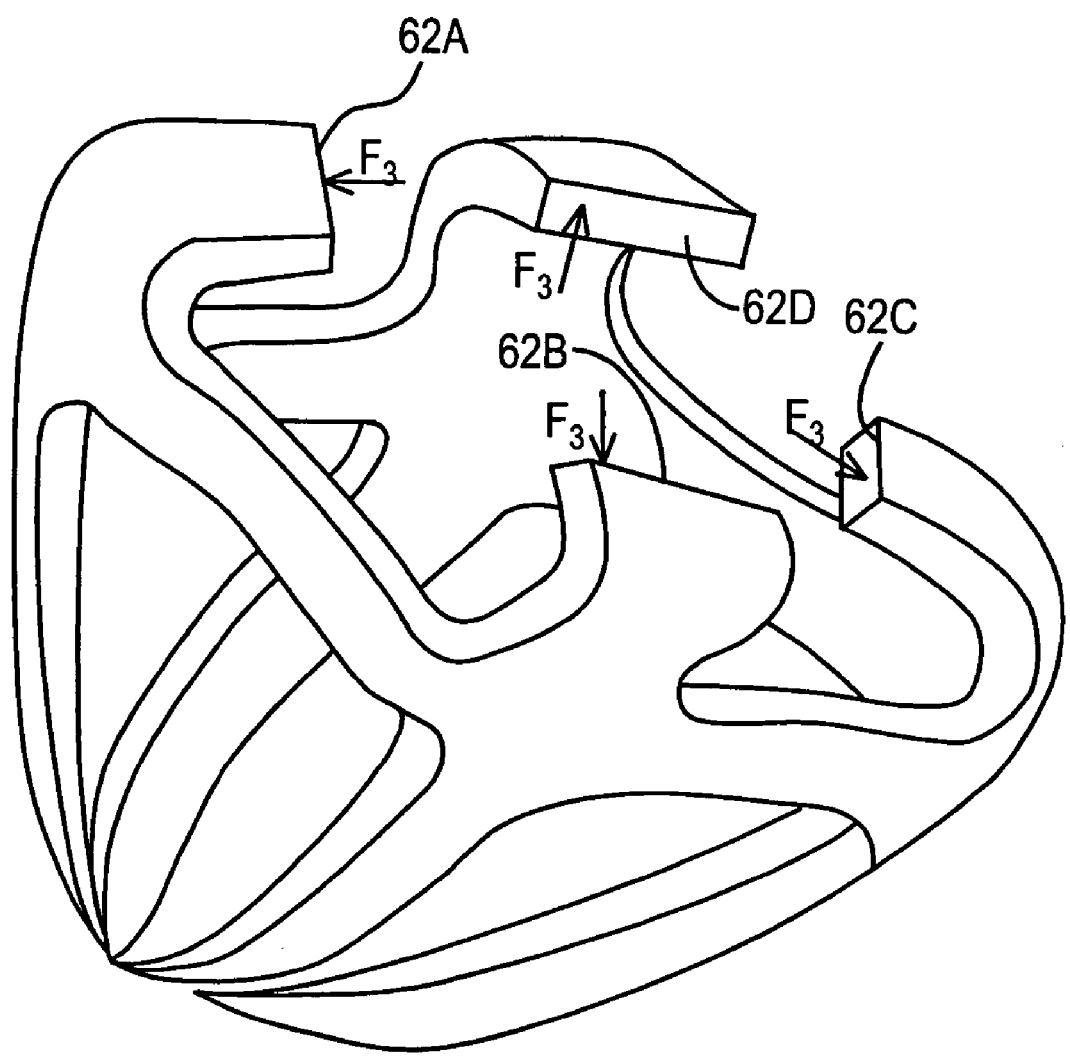

FIGS. 4-6 depict another embodiment of a staple 50 of the present invention. FIG. 4 is the staple in it's formed position, FIG. 5 is the staple just prior to deployment into tissue with the prongs extended outwardly, and FIG. 6 is the staple closed around tissue. Similar to the first embodiment, the staple 50 of this embodiment comprises a plurality of prongs 52A-52D arranged about a centerline axis 100. A shoulder 56A-56D is provided and is generally defined by a relatively flat surface, generally orthogonal to centerline axis. Shoulders 56A-56D may be viewed as an extension of each prong, bent inwardly toward the centerline axis. In this embodiment, webs 54A-54D are connected to and between each prong, and are formed to extend inwardly from each prong toward the centerline axis, creating a U shape generally orthogonal to the centerline axis (as opposed to the previous embodiment in which the U-shaped tab is positioned generally parallel to the centerline axis). Each of the features of the staple 50 of this embodiment is detailed below.

In the formed position (FIG. 4), prongs 52A-52D extend generally parallel to central axis 100, as shown. At the distal end of each prong, tapered points 58A-58D are formed to extend inwardly toward the centerline axis 100. At the proximal end, shoulders 56A-56D meet at prongs 52A-52D, respectively. Web portions (webs) 54A-54D are generally U-shaped, and are formed between each prong extending inwardly toward the centerline axis. As shown, webs connect the prongs at a position distal to the shoulders. The precise position of the webs is determined by the desired extent to which the prongs are extended outwardly, and the extent to which the web curves inward toward the centerline axis. The space between the shoulders and the web portions defines a slot 60A-60D.

Figure 5A:
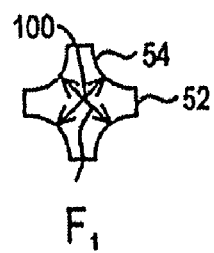

Referring specifically to FIG. 5, the staple 50 is deformed so that prongs 52A-52D extend outwardy from the centerline axis, prior to deployment into tissue. As with the previous embodiment, it is advantageous to extend the prongs outwardly as shown so as to grasp a large portion of tissue, and so that insertion of the prongs into the tissue occurs at a locus away from the wound site, thereby providing a more consistent wound closure (by closing the wound with more of the surrounding tissue) and ensuring complete (or near complete) closure of the wound. To deform the staple into the position shown in FIG. 5, a force $F_1$ is applied to webs 54A-54D, as shown in relief in FIG. 5A. Force $F_1$ is generally outward from the centerline axis and causes the webs to deform outwardly, i.e. straightening the bend of the web by moving the centermost point of the web outwardly. By deformation of the web portions in this manner, the prongs move outwardly. Thus, the cross-sectional diameter of the staple gets larger at the distal end (with respect to the cross-sectional diameter of the formed staple of FIG. 4). Note that the movement of the prongs is generally greater at the distal portions thereof than at the proximal portions thereof, thus producing a staple with outwardly extending prongs. For completeness, it should be noted that a holding force may be applied downwardly (i.e., substantially parallel to the centerline axis) against the top of the webs in slots 60A-60D to hold the staple in place. Also, it is preferred that these forces are simultaneously applied to each web of the staple to produce uniform deformation of each prong of the staple. As mentioned above, it is preferable that the deformation of the staple is plastic, so that the staple does not tend to return to the shape depicted in FIG. 4. Deformation of the staple into this position will be described in greater detail below in reference to the preferred stapler device of the present invention.

FIG. 6 depicts the staple 50 in a closed or deployed position. The closed position, as stated herein generally means that the prongs of the staple are moved inwardly toward each other. To draw the staple into the closed position depicted in this Figure, a force $F_3$ is applied to the inner surfaces 62A-62D of the shoulders. This force is generally orthogonal to the centerline axis, and the angle between each force approximates the angle between the inner surfaces 62A-62D about the centerline axis (which, in the staple of this embodiment is approximately 90 degrees). This force urges the shoulders outwardly. Note that shoulders can only extend outwardly as far as the web portions will permit. Outward movement of the shoulders causes the prongs to move toward each other, since, there is a general pivot about the web portions. Opposite to the movement of FIG. 5, deformation shown in FIG. 6 results in an expanded cross-sectional diameter of the proximal end of staple, and a diminished cross-sectional diameter of the distal end of the staple (with respect to the formed staple of FIG. 4 and the deformed staple of FIG. 5). Again, deformation of the staple 50 into this position will be described in greater detail below in reference to the preferred stapler device of the present invention.

In either embodiment described above, it should be evident that although the Figures depict four each of the prongs, tabs and shoulders, this should be only be considered exemplary. It may be desirable to adapt the staple 10 or the staple 50 with more or fewer prongs, tabs and shoulders for a given application. Also, it is not necessary that each prong is the same length, or that each prong has the same overall dimensions. In alternative embodiments, the entire staple, or selected portions thereof can be alternatively fashioned from an elastic or shape memory (e.g., nitinol, and/or other elastic materials, including for example temperature dependant shape memory materials) material thereby permitting elastic deformation from the a static closed position to an expanded position and then elastically close about the wound. Also, the embodiment of FIGS. 4-6 can be adapted with a tissue stop positioned along the length of the prong, as shown in FIG. 3A.

Stapler Device

Figure 3A:
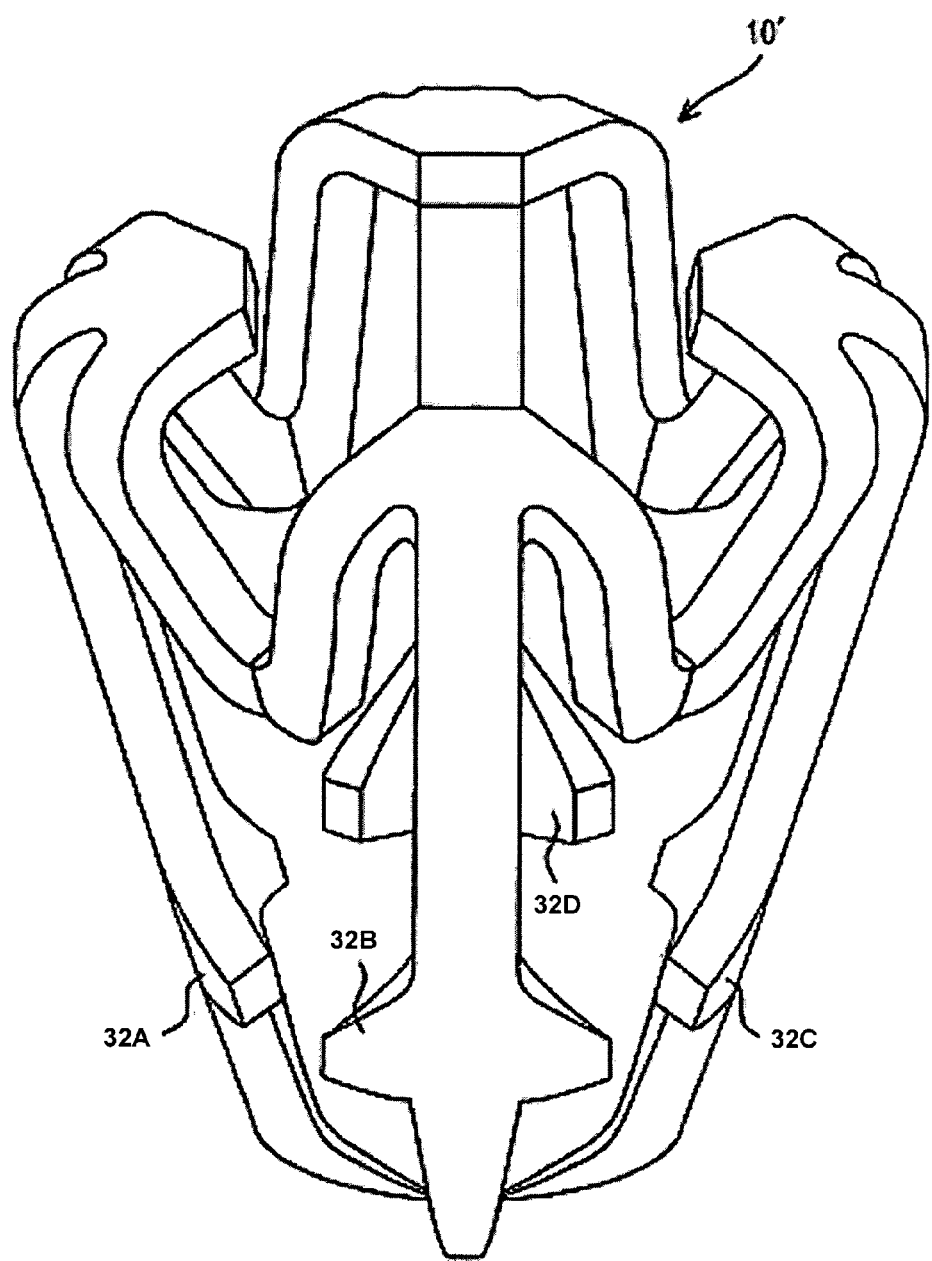
FIG. 3A depicts an isometric view of alternative staple of the embodiment of FIGS. 1-3.

Another aspect of the present invention is a stapler device to deploy the staple 10 of FIGS. 1-3, the staple 10' of FIG. 3A, and the staple 50 of FIGS. 4-6. As a general overview, the stapler of the present invention includes a distal tip for holding and deploying a staple, and an actuator mechanism to cause a staple, or at least the tissue piercing portions of a staple, to expand outwardly and then close about a wound. The stapler of the present invention facilitates one object of the present invention to ensure that the staple closes a greater amount of tissue as compared with conventional stapling mechanisms. The following description will detail various exemplary mechanisms to accomplish this goal, but it should be recognized that numerous alternatives will be readily apparent to those skilled in the art, and all such alternatives are to accomplish these objectives are deemed within the scope of the present invention.

FIG. 7 depicts an isometric view of one embodiment of a stapling device 100 of the present invention. The device generally includes an actuation mechanism 104 and a distal tip 102. FIG. 8 is a more detailed view of the distal tip 102 of the stapler device 200. The distal tip preferably comprises an inner rod member 110 slidable within an outer sleeve 112. Rod 110 includes a flared or mandrel portion 114. Mandrel 114 also includes slots 118A-118D, which in use are aligned with fingers 116A-116D. Fingers 116A-116D mate with slots 20A-20D and 60A-60D of the staple 10 and 50, respectively. Preferably, rod 110 is removable for staple attachment thereto, where a staple is positioned between the mandrel and the sleeve. The mandrel, as will be described below, is responsible for the forces generated on the staple.

FIGS. 9, 10A, 10B, 11A and 11B depict the working relationship between the staple 10' and/or 50 of the present invention and the mandrel 114/sleeve 112 of the stapler mechanism 200. In FIG. 9A, the staple 10' is placed between the mandrel 114 and sleeve 112. Slots 20A-20D of the staple engage fingers 116A-116D of the sleeve. The prongs 12A-12D of the staple are dimensioned so as to fit over the mandrel, and tabs 14A-14D are dimensioned so as to fit over the rod 110, as shown. Similarly, for the staple 50 shown in FIG. 9B the staple 50 engages the mandrel 114 and sleeve 112 (not shown). This is a static position, as no forces are applied to the staple to cause deformation. In FIG. 10A, the staple 10' is urged into the first deformed position (of FIG. 2) by the relative movement of the rod/mandrel and the sleeve. As shown, the mandrel is urged proximally. As the mandrel moves, the tabs of the staple meet the narrowest part of the mandrel. Further movement forces the tabs to move outwardly, causing the prongs to likewise move outwardly (as described above with reference to FIG. 2). Once the tabs clear the mandrel, outward movement of the tabs and prongs ceases. Similarly, in FIG. 10B, the movement of the mandrel forces webs to extend outwardly causing the prongs to extend outwardly (as described above with reference to FIG. 5). Once the webs clear the mandrel, outward movement of the prongs ceases. FIG. 11A depicts final deployment of the staple into tissue. As the mandrel is drawn further proximally and once the tabs have cleared the mandrel, the shoulders (not shown) are spread outward, forcing the prongs to move together (toward the centerline axis) and closing tissue therebetween. FIG. 11B depicts the same actuation, but for the staple 50 of FIGS. 4-6.

Figure 12:
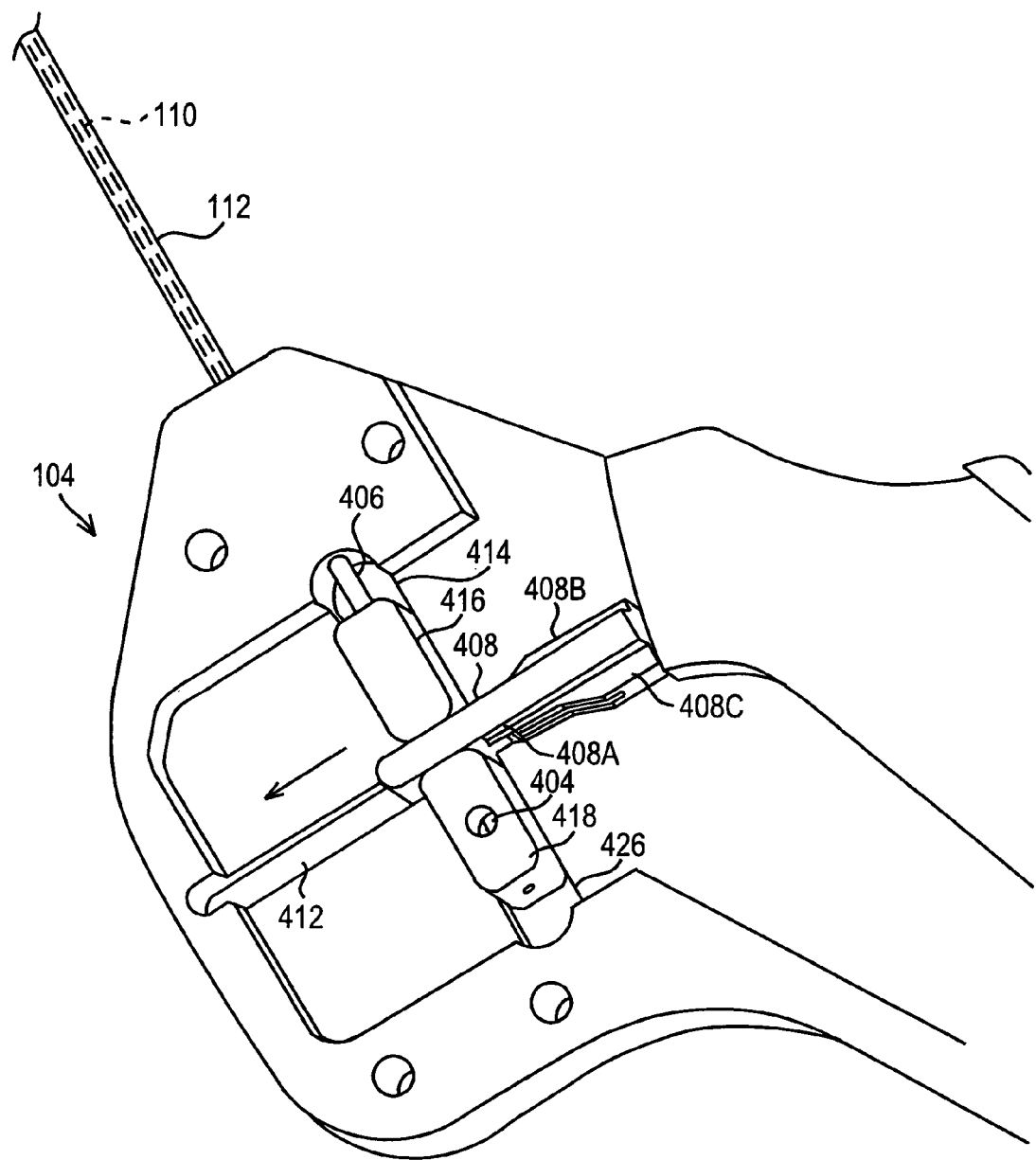
FIGS. 12-15 are isometric views of an exemplary staple deployment mechanism of the stapler of the present invention.

FIGS. 12-15 depict an exemplary actuator mechanism 104, showing the relative motion of the sleeve 112 and the mandrel rod 110. The mechanism includes a cam 408 movable in a linear motion along a slot 412. Movement of the cam can be manual or through an electronically controllable motor (not shown). The cam 408 has lobes 408A and 408C located on a first side of the cam 408 and a lobe 408B located on a second and opposing side of the cam 408. A first cam follower 418 is coupled to the mandrel rod 110, and is selectably engagable with lobes 408A and 408C. A second cam follower 416 is coupled to the sleeve 112, and is selectably engagable with lobe 408B. FIG. 12 depicts that neither cam follower is in contact with the lobes, and is indicative of an initial position of the mechanism.

Figure 13:
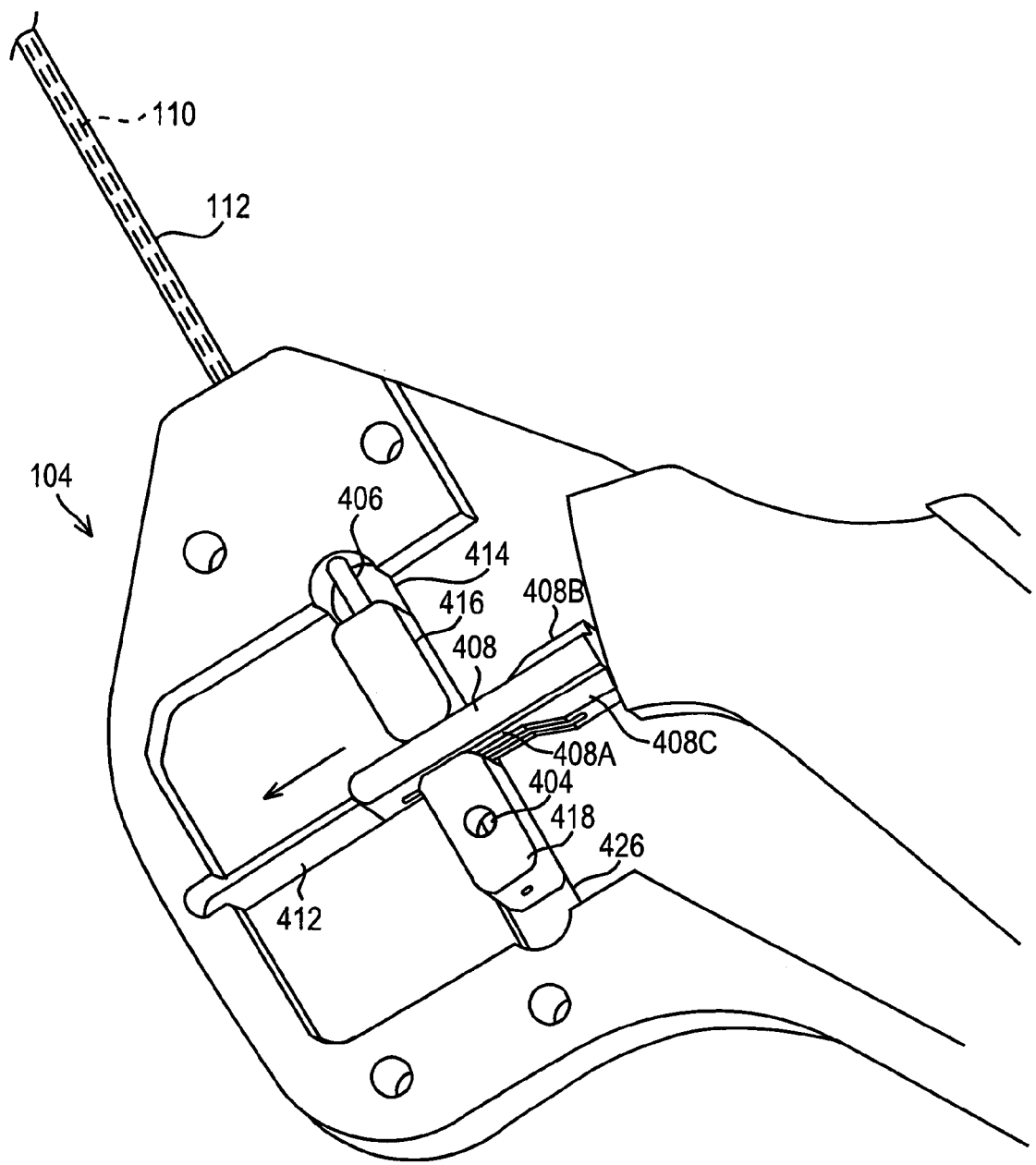
Figure 14:
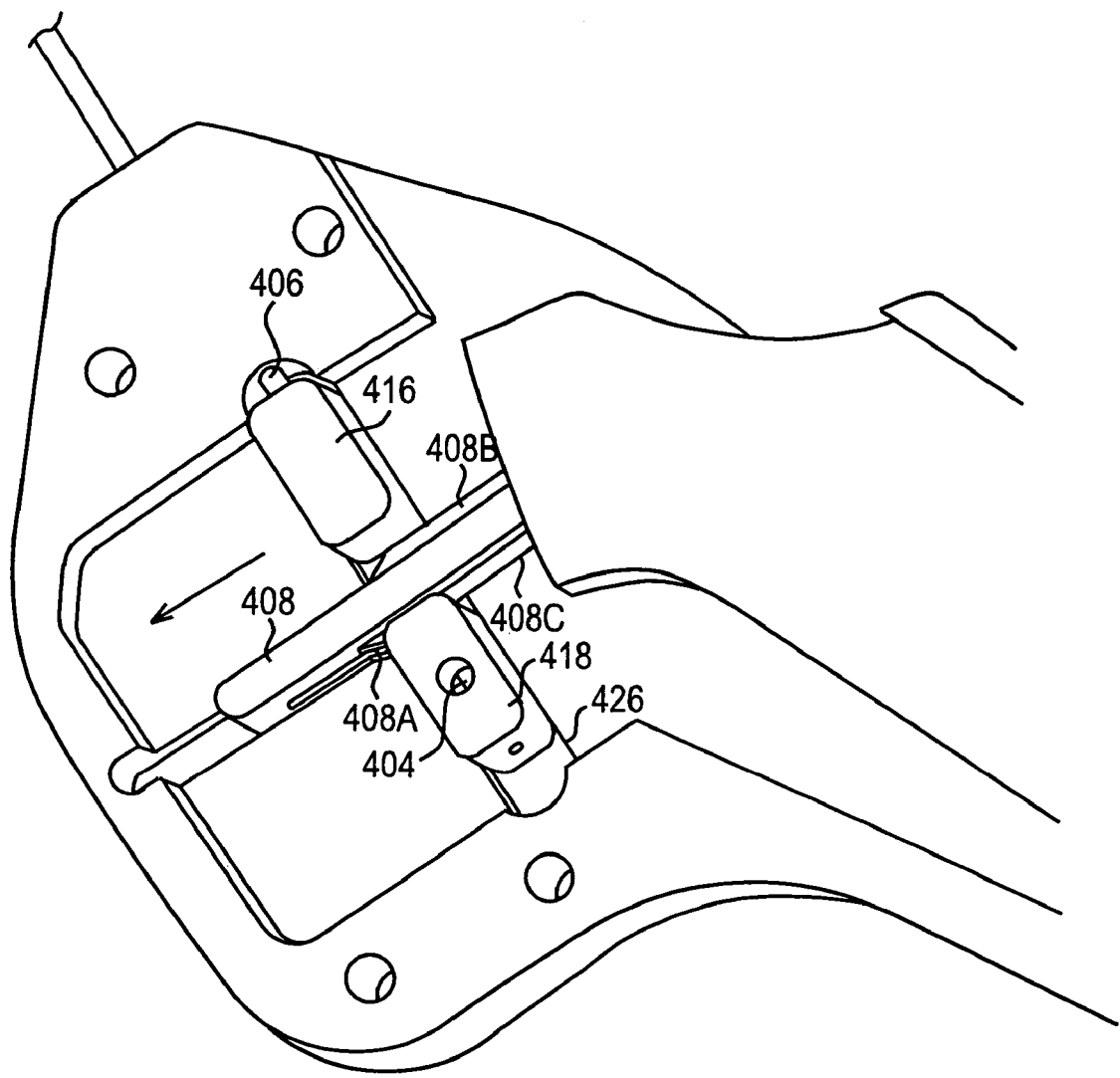
Figure 15:
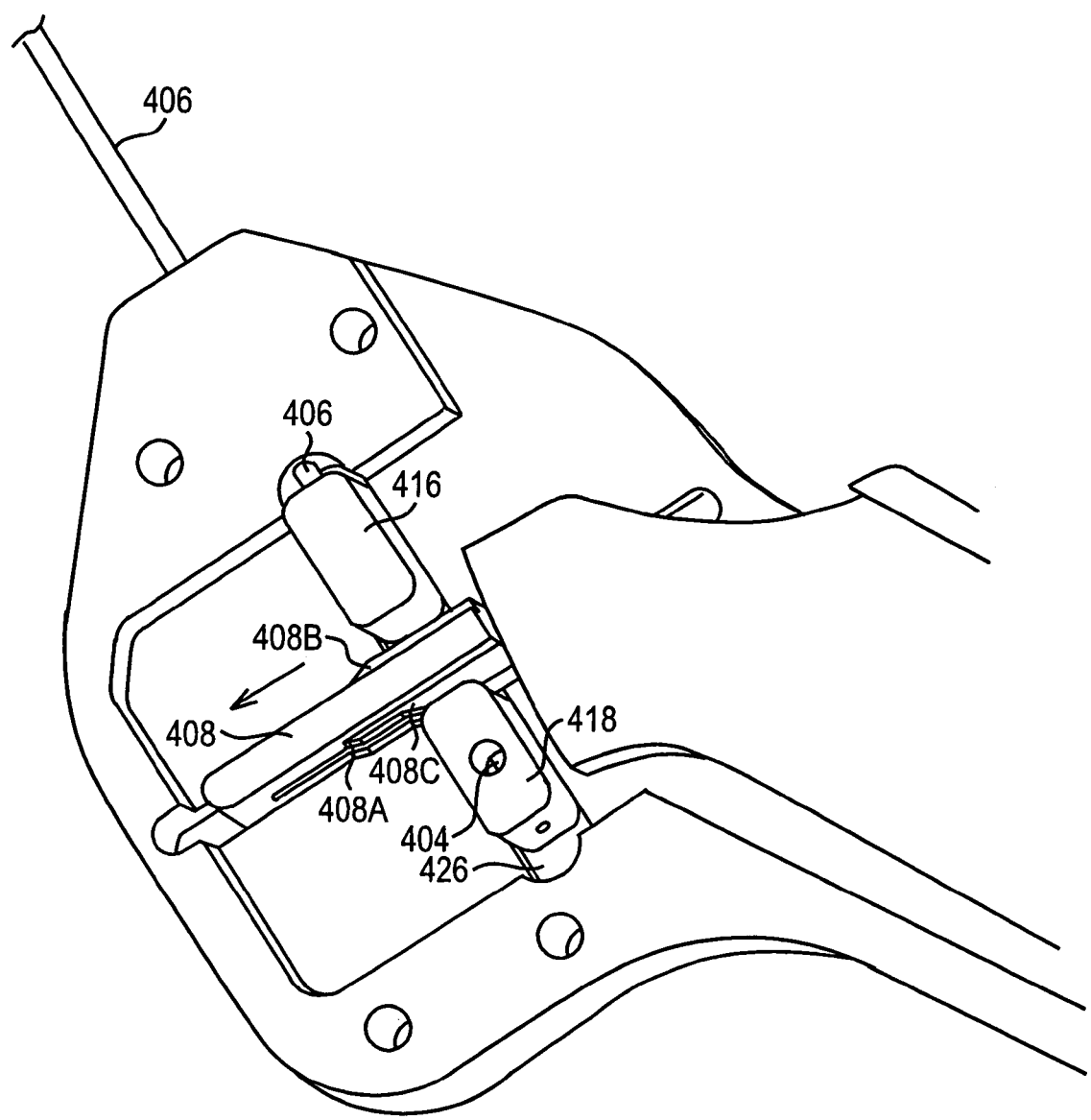

FIG. 13 depicts the mechanism 104 in a position to expand the staple between the mandrel 114 and the sleeve 112, as shown in FIG. 9A. As cam 408 is moved (as indicated by the arrow), lobe 408A urges cam follower 418 along slot 426. The mandrel rod 110 is moved proximally, causing the prongs to extend outwardly (as shown in FIGS. 2 and 5) as a result of the force of the mandrel 114 on the tabs or the web portions. With further movement of the cam 408 (FIG. 14), lobe 408B now urges cam follower 416 to move distally, thereby moving the sleeve distally relative to the mandrel rod and causing further expansion of the prongs and causing the staple to move distally. Finally, in FIG. 15, the cam is urged yet further and cam follower 418 is urged by lobe 408C causing the mandrel and madrel rod to extend further proximally. This relative movement between the cam rod and the sleeve causes the mandrel to apply a force to the shoulder portions of the staple, in turn causing inward movement of the prongs. Lobe 408C causes closure of the prongs and decouples the staple from the mandrel. This is the fully deployed staple movement.

Figure 16:
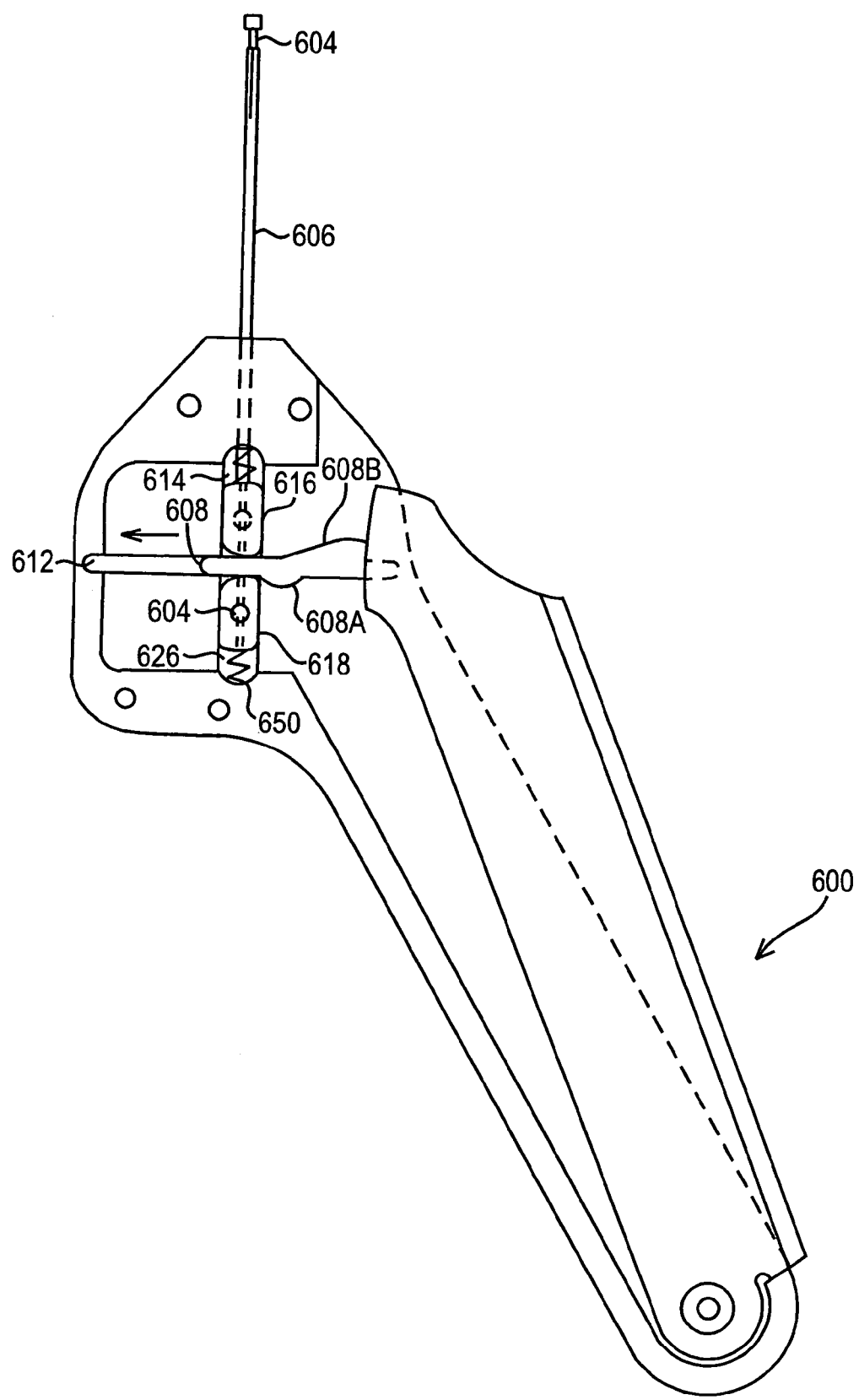
FIGS. 16 and 17 are isometric views of another exemplary staple deployment mechanism of the stapler of the present invention.
Figure 17:
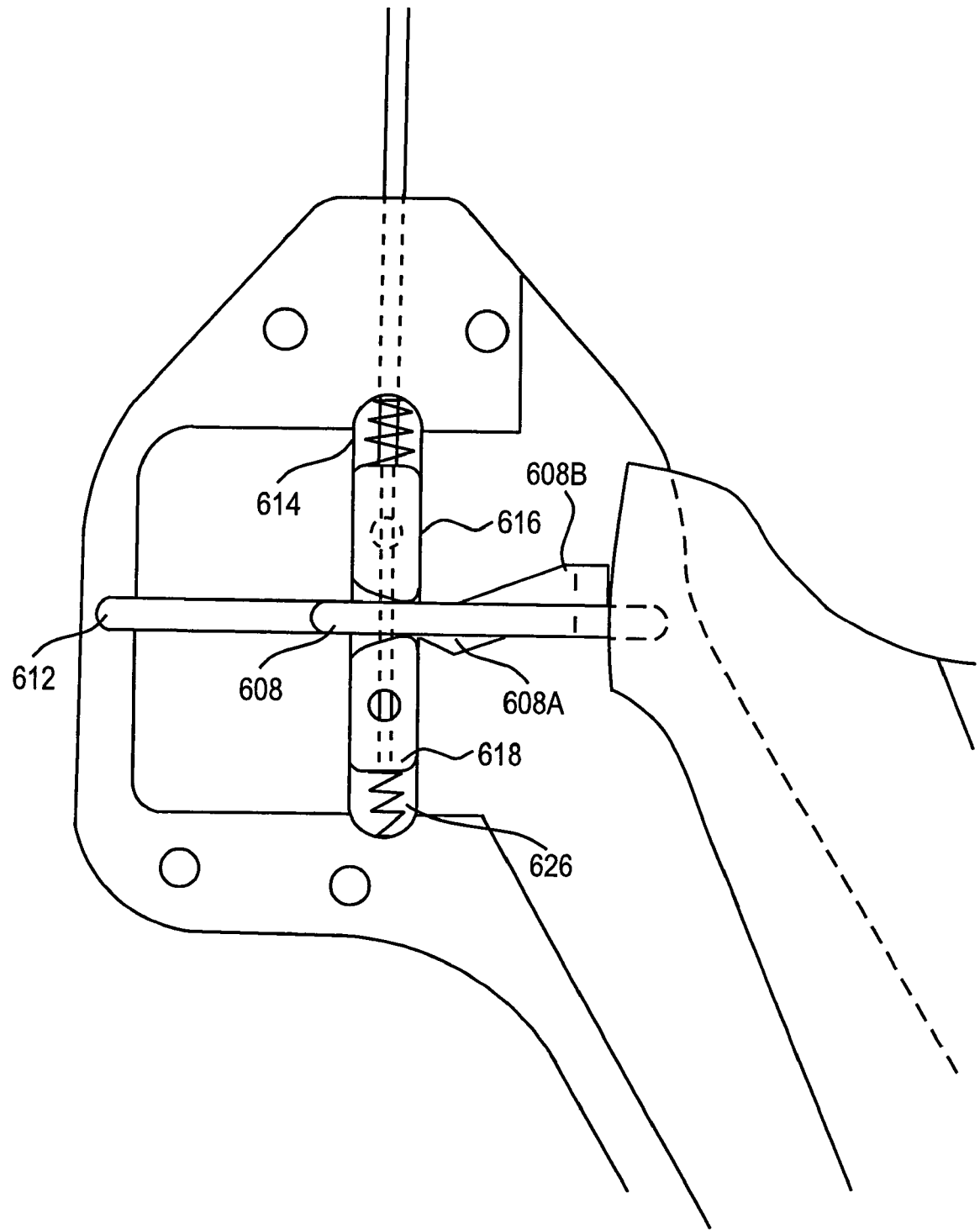

FIGS. 16 and 17 show an alternative cam mechanism. Similar to the previous example, cam 608 is urged in a direction indicated by the arrow to cause relative motion between the mandrel rod and the sleeve. Lobes 608A and 608B are located on opposite sides of cam 608. As the cam 608 is moved along slot 612, the lobe 608A urges a cam follower 618 in a linear motion along a slot 626. This urges the cam follower 618 proximally. The cam follower 618 is coupled to a mandrel rod 604. This deforms staple 10/50 in the second configuration (see FIG. 2 or 5). As the cam 608 is urged further, the cam follower 618 moves distally to stay in contact with the lobe 608A. This urges mandrel rod 604 distally. The same movement of the cam 608 urges lobe 608B to urge cam follower 616 distally. The cam follower 616 is coupled to a sleeve 606. This urges sleeve 606 distally. The downward slope of lobe 608A is parallel with upward slope of lobe 608B so the mandrel rod 604 and the sleeve 606 move distally in unison and the staple is advanced into the tissue. The movement of the cam follower 618 down the slope of lobe 608A then ceases while the movement of cam follower 616 continues up the slope of lobe 608B, the staple 10/50 is deformed into the closed or deployed configuration (see FIG. 3 or 6). Springs 614 and 650 can be provided to return cam followers 616 and 618, respectively, to an initial position. Of course an additional spring can be provided in slot 612 to move cam 608 back to an original position.

Alternatively, the actuation mechanism can include a rotating drum (not shown) to replace the cam 408 and 612. The drum may be adapted with lobes formed thereon, similar to lobes 408A-408C and 608A-608B, respectively. Other alternatives may include a rotating screw having a variable width in accordance with lobes 408A-408C or 608A-608B to actuate the mandrel rod and/or sleeve. Of course, instead of the cam mechanisms depicted in the Figures, direct linkage may be used to actuate the mandrel rod and/or sleeve.

Wound Site Management

1. First Exemplary Introducer

Figure 18:
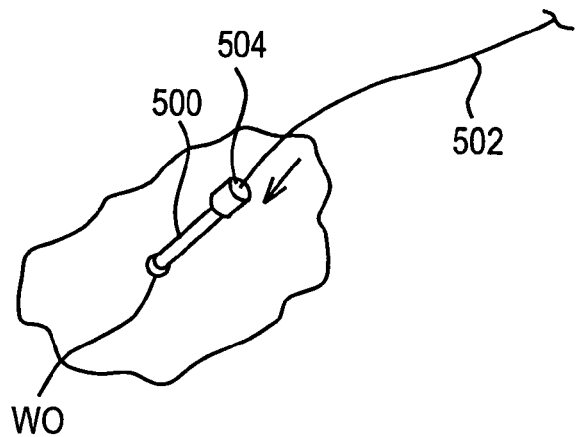
Figure 19:
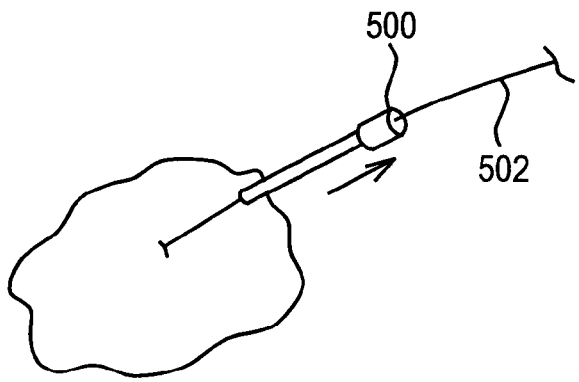

FIGS. 18-26 depict one exemplary structural and procedural embodiment of wound site management during and after a medical procedure, such as angioplasty. FIG. 18 depicts a conventional tubular sheath 500 extending through the skin, soft tissue and the puncture in the vessel wall of a patient. Typically, the sheath 500 is left in place following a completed medical procedure. To start the stabilization process of the wound site, the doctor inserts a flexible guide wire 502 through an opening 504 in the end of the dilator 500. FIG. 19 shows removal of the sheath 500 from the wound site after the guide wire 502 is properly inserted through the skin and into the artery.

Figure 20:
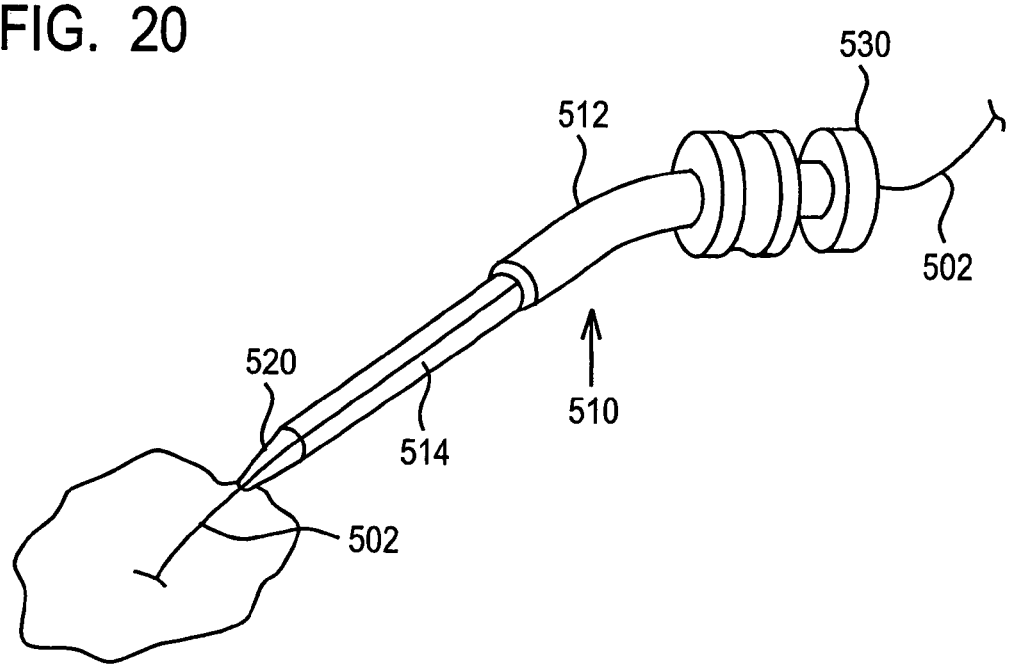

To facilitate efficient and effective wound closure, another aspect of the present invention provides an introducer formed to stretch the wound site. FIG. 20 depicts an exemplary introducer 510 of the present invention, and continues the process from FIGS. 18 and 19 where the introducer 510 slides over the guide wire 502 until a portion of the dilator 520 is placed into the artery. Details of the introducer 510 are disclosed below.

Figure 20A:
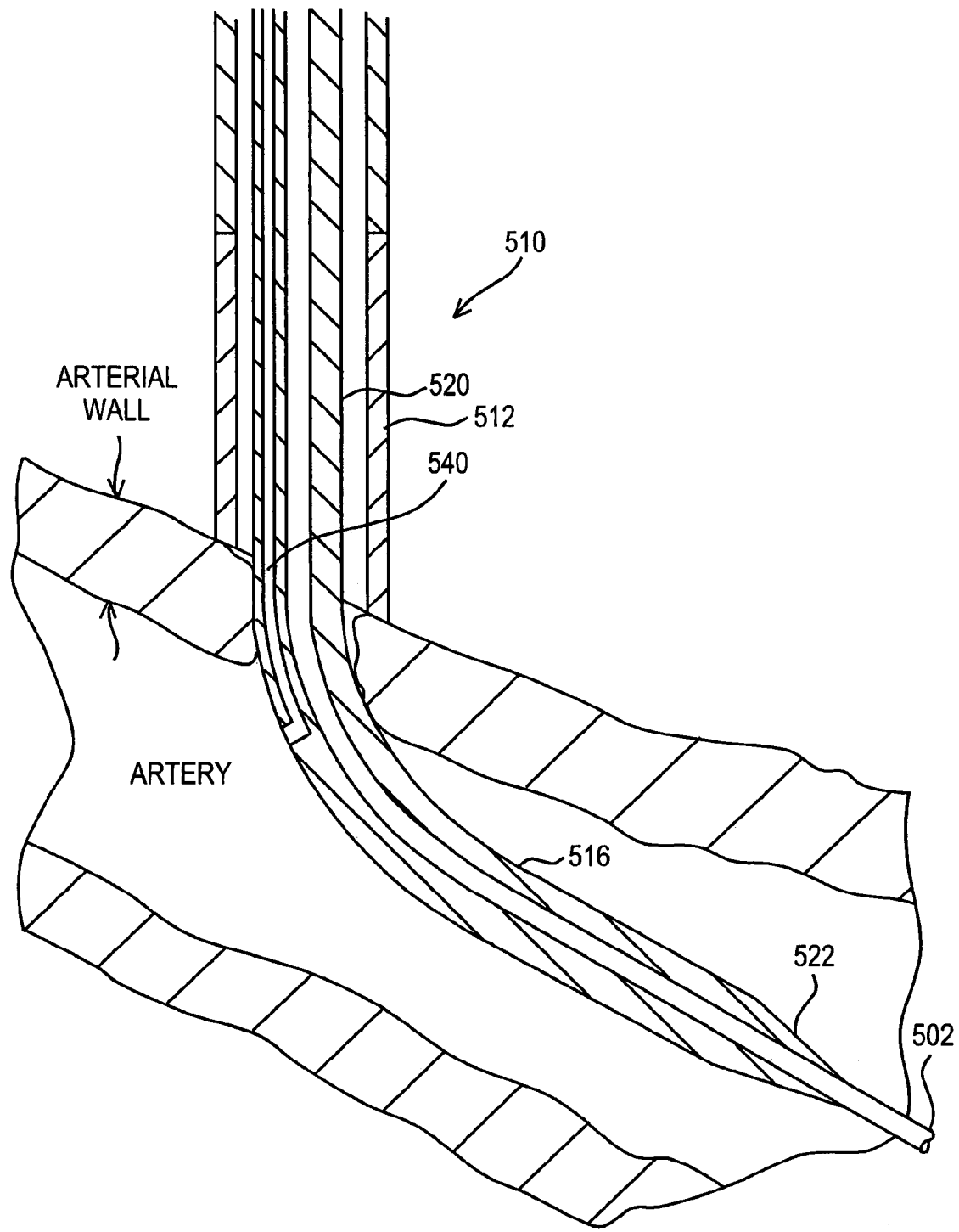
FIGS. 20A, 33, 34, 37 and 38 are isometric views of blood marling devices and methods of the introducer of the present invention.

FIG. 20 depicts the introducer 510 inserted over the guide wire 502 (already in the artery) and into the artery. The introducer is comprised of a hollow elongated guide sheath 512 and dilator 520. Referring to FIG. 20A, the doctor urges the distal end 516 of the dilator 520 into the wound, until the presence of fluid (blood) within the blood marking lumen 540 indicates that the dilator 520 is properly positioned in the artery. The blood marking lumen 540 is located at a predetermined length along the dilator 520 to allow blood to flow through a cavity (lumen) 540 to alert the doctor that the dilator 520, and more specifically the flexible distal end 516, is properly inserted in an artery to a desired depth. The distal end 516 of the dilator may include a tapered tip portion 522 to facilitate easier ingress through the skin and into the artery. An additional blood marking passageway (not shown) can be included proximal to the first blood marking passageway on the dilator or on the distal end of sheath 512 as precautionary indicator of the depth of the dilator. Presence of blood in this additional passageway is indicative of the dilator being pressed too far and into the arterial wall or into the artery. Of course, those skilled in the art will recognize that the introducer 510 will include internal passageways (lumens) for blood marking and the guide wire.

Figure 21:
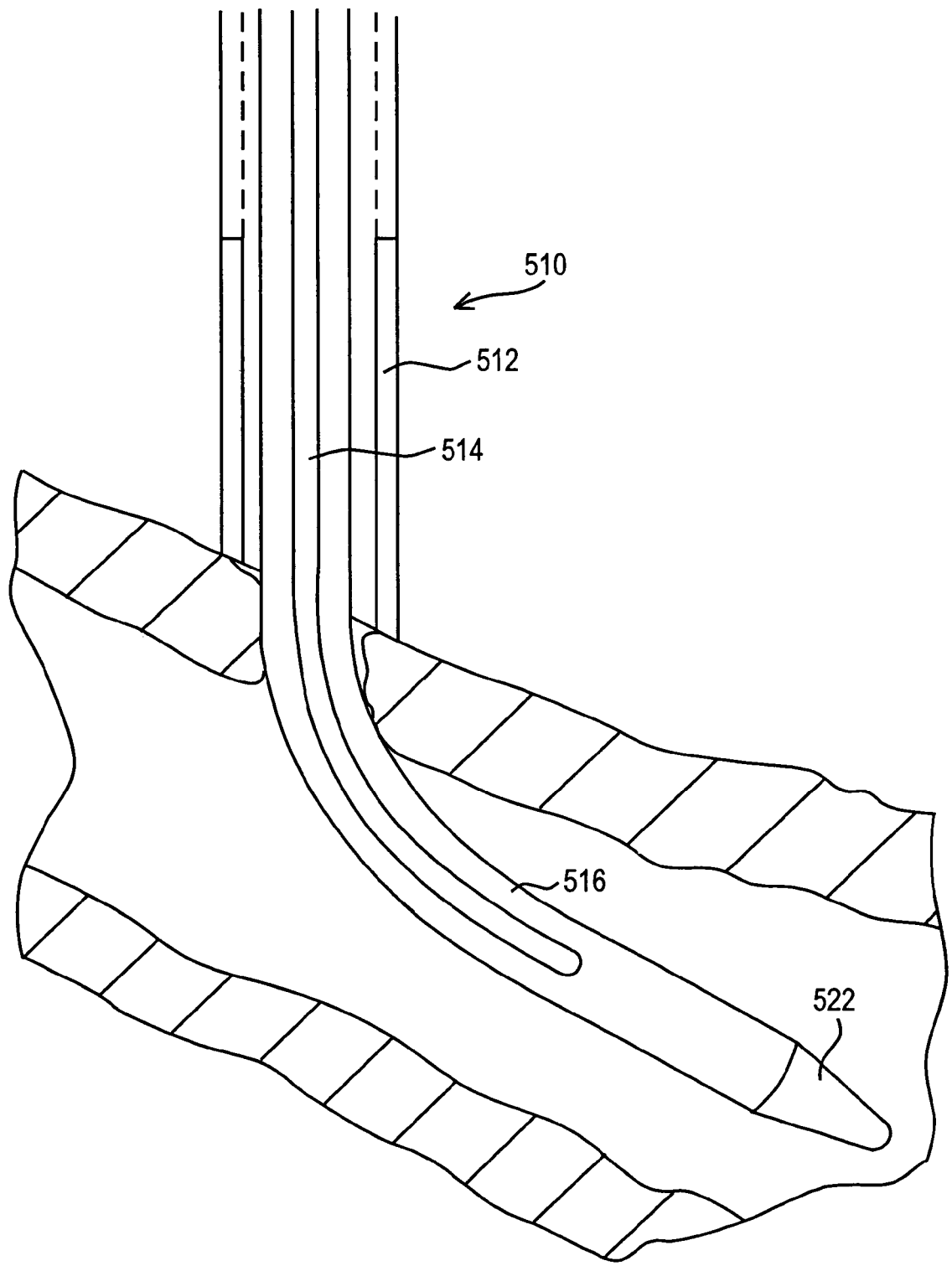
Figure 26:
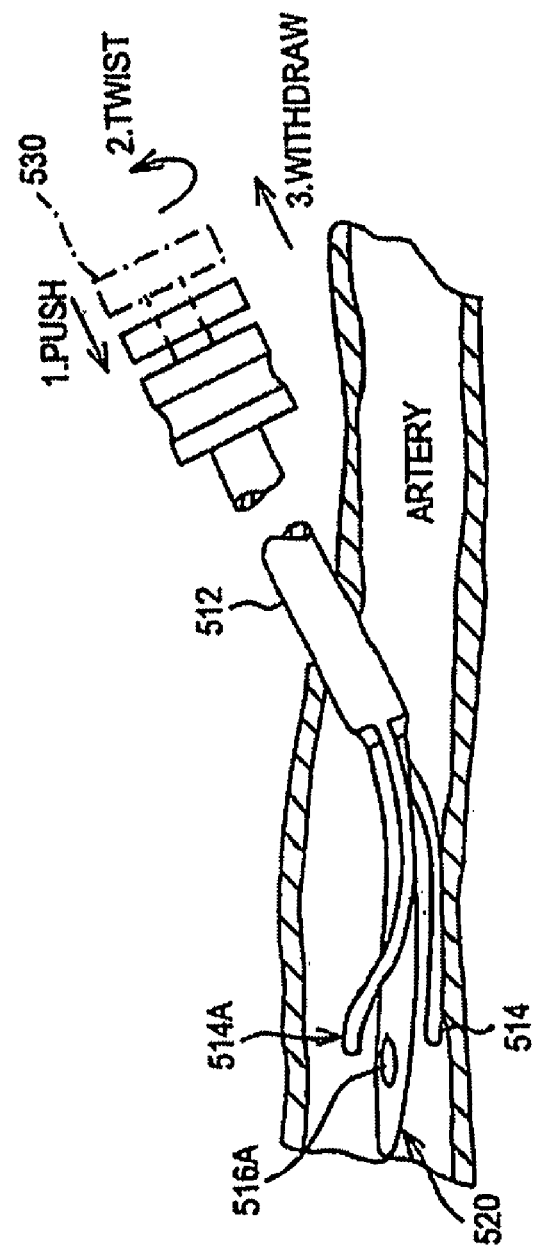

One feature of the guide sheath of this exemplary embodiment is the use of two or more wire guides 514 to maintain the sheath located on the wound site, to provide approximation of opposing sides of the wound, to ensure that the closure device (e.g., stapler/staple, suturing device, cauterization, etc) remains located about the wound so that a closure device is properly deployed, and to provide unobstructed access to the wound site. In this embodiment, wire guides 514 are formed on opposing sides of the guide sheath 512. Having the wire guides 514 on opposing sides helps to ensure that not only is the distal end of the sheath located on the wound site, but that the sheath is approximately centered thereon. The wire guides are delivered into the artery by the dilator 520, as shown in FIGS. 21 and 26. The wire guides are removably coupled to or contained within the distal end 516 of the dilator 520 and deployed into the wound, as shown in FIG. 26. The wire guides can be releasably held in openings or slots (not shown) on the sides of dilator. Once the dilator is properly inserted into the wound to a proper depth (as indicated by the BM passageway), the dilator is removed from the wound and the guide sheath. To remove the dilator 520 from the guide sheath 512, the doctor (or clinician) first holds the guide sheath 512 and advances the dilator 520 inward (distally) through the guide sheath 512. This decouples the wire guides 514A and 514B from the openings. To ensure that the wire guides 514A and 514B properly decouple from the dilator 520 before the dilator is withdrawn, a mechanism is provided that does not allow withdrawal until the guide rod has been inserted a predetermined distance. As shown in the drawing this mechanism 530 can include a mechanism that requires a twisting motion or other action prior to withdrawal. After the guide rod has been inserted the predetermined distance, the doctor extracts the guide rod. This leaves the guide sheath 512 centered on the wound with the wire guides 514A and 514B extending inside the wound.

Figure 23:
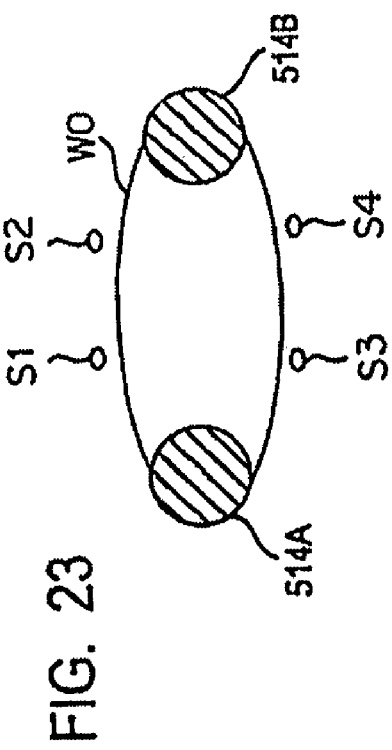

As is understood to those skilled in the vascular anatomy arts, a puncture in an artery or vein has a general tendency to manifest a slit or an elongated opening generally perpendicular to the length of the vessel. This is due to the circumferential (rather than longitudinal) cell structure of the vascular tissue which supports radial expansion and contraction of the vessel. The wire guides 514A and 514B of the present enable the wound to approximate the natural state of the wound, i.e., elongated circumferentially. The sheath may have a diameter approximately equal to the diameter of the opening or wound, so that the distance across the wire guides 514A and 514B approximately equals the dimension of the long axis of the wound, as best shown in FIG. 23. Once inside the vessel, the wire guides 514A and 514B in this position limit movement of the sheath along the long axis, and since the wound is elongated, movement along the short axis is likewise limited. In this embodiment, since the wire guides 514A and 514B are disposed on opposing sides of the sheath, any device inserted through the sheath will be approximately centered on the wound. Additionally, the wire guides are long enough to push against the opposite vessel wall (distal wall) thereby preventing the distal wall from being punctured or captured by the closure device, or the vessel from being occluded by a closure activity during a closure activity at the puncture site.

Importantly, since the wound opening tends to assume the shape shown in FIG. 23 even in the absence of the wire guides, the opposing tissue located along the short axis tends to approximate. The present invention takes advantage of this tendency. If the position of the wire guides define a circumference larger than the circumference of the wound, the tissue along the short axis tends to approximate more, because the tissue on the long axis is stretched, thereby creating tension on the wound site. In other words, in this configuration, the wire guides are dimensioned apart such that an outward force is created along the long axis of the wound site, and this causes the tissue on either side of the short axis of the wound to come together. It will be appreciated by those skilled in this art that the amount of tension required will be tissue dependant, and thus, the overall diameter of the sheath and wire guides should be sized according to the wound size and tissue strength. For example, vascular tissue is relatively elastic, and can tolerate more tension than other tissues (e.g., dura-matter, duct tissue, bladder tissue, etc.). The sheath and dilator of the present invention take these factors into consideration and are accordingly sized for the particular tissue application.

However, sufficient wound site management according to the present invention does not require that the wire guides stretch the wound. Rather, if the outside dimension across the wire guides (i.e., the outside diameter of the sheath plus the outside diameter of both wire guides) is shorter than the long axis of the elongated wound, the wire guides still serve to maintain the sheath generally located (and possibly centered) on the wound. In both circumstances, the wire guides ensure that a closure modality (e.g., staple) deployment is more accurately centered on the wound site. As described above, when tension is created on the wound site, tissue along the short axis tends to come together, and thus a certain amount of tissue is available which may be advantageously grasped by the staple during closure. Also, if the wound opening in the tissue is held taught by the sheath/wire guides, there is less tendency for the tissue surrounding the opening to slip down into the vessel during staple deployment (which would reduce the effectiveness of the closure).

FIG. 23 also shows examples of locations S1, S2, S3, and S4 of where the prongs of the staple to be inserted will line-up relative to the wound opening WO. The wire guides 514A and 514B are depicted disposed on opposing sides of the guide sheath 512, and more specifically, the wire guides are inserted into the wound opening along the long axis of the wound opening in the artery or vein, so that the wound is pulled taught along such axis.

Figures 22, 22A:
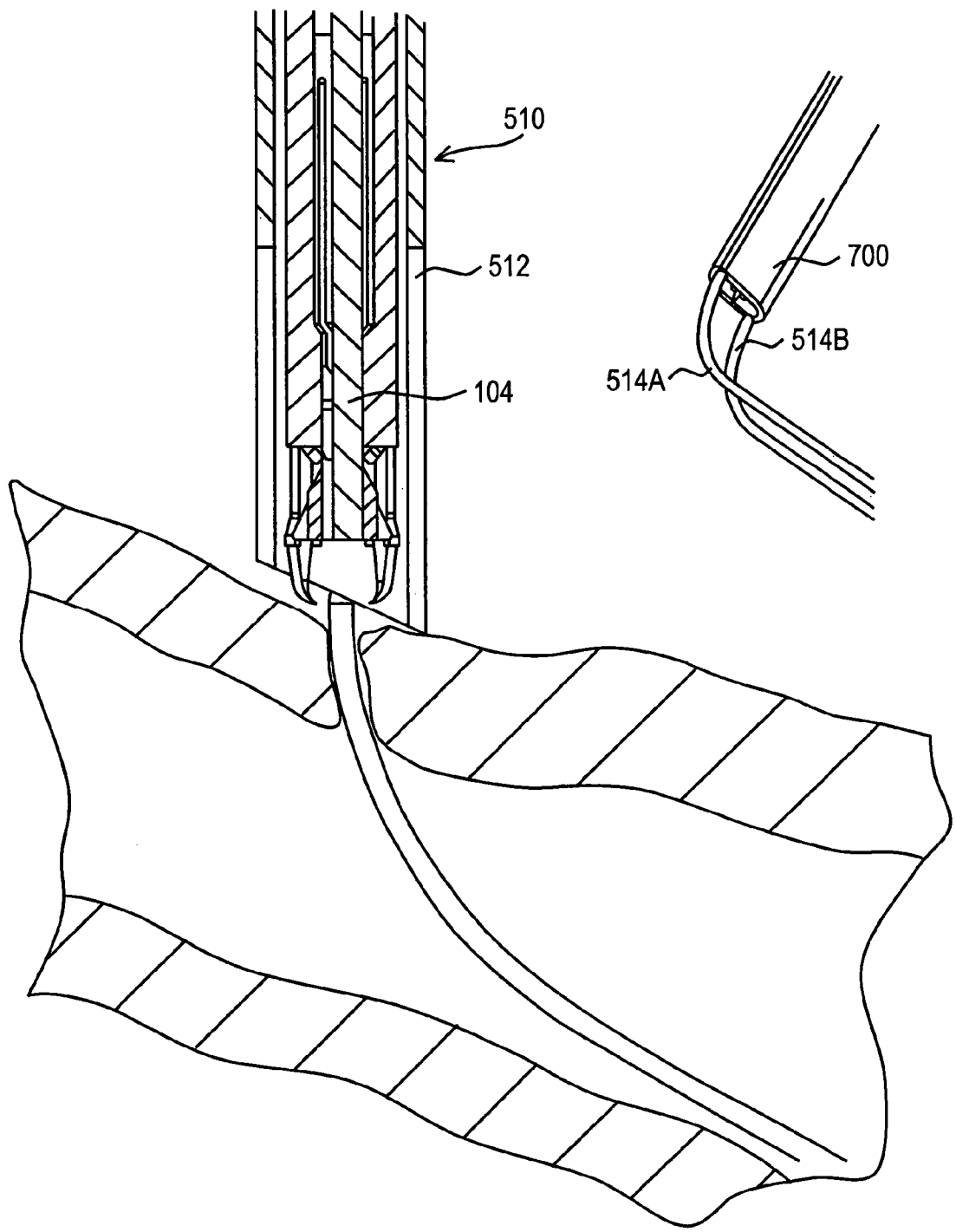
Figures 25, 25A:
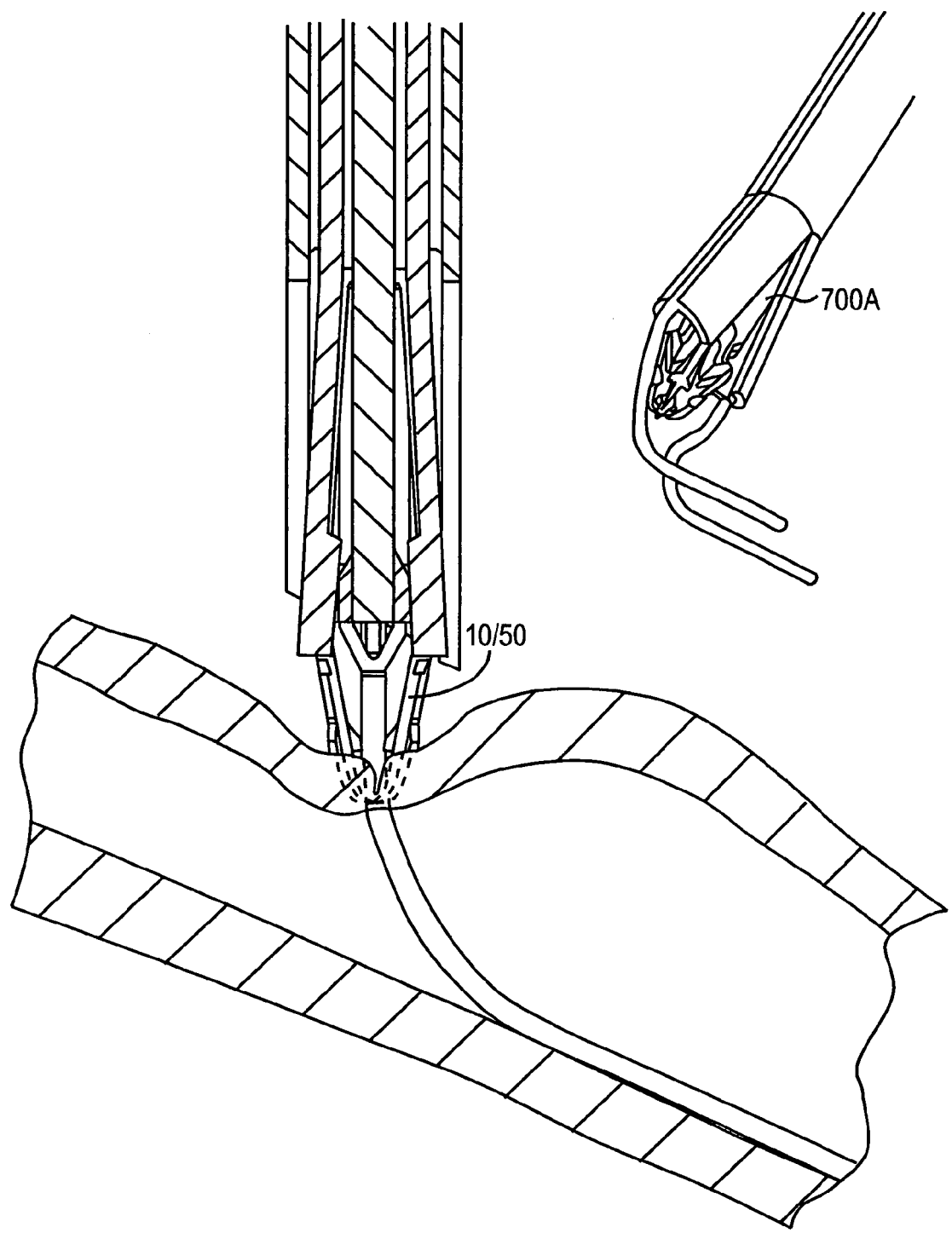

FIG. 22 shows the distal end of a stapler 104 with a staple 10/50 being inserted through the guide sheath 512 of the introducer 510. The diameter of distal end of the guide sheath 512 may be formed to expand if outward pressure is applied to inside surface of the guide sheath 512. For example, slits or weakened tear seams (described below) may be formed in the distal end of the guide sheath 512 to allow the diameter of the guide sheath to increase when pressure is applied. Alternatively, the sheath may comprise slots on the distal end to permit expansion. FIG. 22A depicts a relief view of the introducer 510, and more clearly depicts a slit or weakened tear seams 700. When the distal end of the stapler 104 is properly inserted in the guide sheath 512, the staple can be deployed into the tissue. FIG. 24 shows the first step of staple deployment, the process of which is described in detail above. Note that in FIG. 24A, the extension of the staple prongs causes the weakened tear seams or slits 700A and 700B to separate. This further causes the wire guides to expand against the long axis of the wound, thereby further approximating the tissue surrounding the opening. The diameter formed by the prongs of the staple 10/50 is now larger than the original outside diameter of the guide sheath 512. FIGS. 25 and 25A depict the staple fully deployed into tissue, the process of which is described above. The stapler, guide sheath 512 and wire guides 514 can now be removed from the closed puncture site.

2. Second Exemplar Introducer

In an alternative exemplary embodiment, instead of using wire guides 514A and 514B as described above, a loop actuation wire 654 is used in conjunction with tubular stabilization guides 660A and 660B, as in the exemplary introducer assembly 510' illustrated in FIGS. 27-32 and 39-39A. The exemplary introducer assembly 510' comprises a guide rod 670 and a guide sheath 662. The guide rod 670 is similar to the dilator 520 of the previous embodiment, and may comprise a flexible tip portion that is inserted into the artery. Accordingly, dilator and guide rod, as used herein may be considered equivalent devices and the terms used interchangeably. As before, during use, the introducer assembly is slidably disposed about a central guide wire 502. The guide sheath 662 includes a plurality of wire stabilization guides 660 (shown as 660A and 660B in FIG. 30), which may be integrated into the guide sheath 662, or alternatively, be formed separately and coupled thereto. The wire stabilization guides 660 generally comprise tubular members disposed around the outside diameter of the sheath, and the loop actuation wire is threaded into each stabilization guide, leaving end portions 656 and 657. A portion of each wire stabilization guide extends from the distal end of the sheath. Guide sheath 662 is a tubular member with an inside diameter dimensioned to slide over the guide rod 670. It is equally contemplated that the guide sheath has an oval or non-circular cross-sectional shape. The sheath further includes one or more slits or weakened tear seams 686 to provide controlled expansion of portions of the guide sheath, as will be detailed below.

The guide rod 670 is a tubular member and includes at least one slot 682 formed therein for releasably holding the loop actuation wire 654. As shown in FIG. 27, the guide rod has a main tubular body dimensioned to fit inside the guide sheath and has a tapered end 800 having an opening 802 at the tip to accept the central guide wire. To releasably hold the actuation wire, at least one longitudinal slot (or slit) 682 maybe formed in the guide rod 670 along its length. To permit temporary holding and controlled release of the loop actuation wire 654, the width of the longitudinal slot (or slit) 682 at the surface of the guide rod 670 may be less than the outside diameter of the stabilization guides 660 or the loop actuation wire 654, so that the stabilization guide and/or loop actuation wire 654 is held within the slot (as shown in FIG. 27) until released by the sliding action of the sheath over the guide rod, as described below. The loop actuation wire and/or wire guides can be held in a slot or slit formed in the guide rod (which may define a separate lumen structure in the guide rod), or alternatively the slot can be formed with a diameter less than the width of the wire or wire stabilization guide to permit the wire or wire stabilization guide to friction fit into the slot. As shown in FIGS. 27-29, the slot 682 may be bounded by a pair of recessed areas 658, 659, so that, for example, the wire guides do not catch on tissue as the guide rod is inserted and removed from an artery or vein. Alternatively, instead of defined slots formed in the guide rod, slits (not shown) may be formed in the material of the rod such that the loop actuation wire 654 is releasably held to the guide rod in a friction fit manner, and released from the guide rod in a similar manner as described above.

In this configuration, one end portion 656 of the loop actuation wire 654 is threaded inwardly into one end of the slot 682 at the first recessed area 658 and back outwardly from the slot 682 at the second recessed area 659 in the guide rod 670. Similarly, the other end portion 657 of the loop actuation wire 654 may be threaded through a second slot (not shown), which may optionally include a set of recessed areas (not shown) on the opposing side of the guide rod 670, or elsewhere along its length. The slot 682 may be located along the length of the guide rod 670. For example, as shown in FIGS. 27-32, the slot 682 is located along a line parallel to the central axis of the guide rod 670. Of course, it is not a requirement of the present invention that the slot be formed in this manner, nor that the slot include recessed areas at its ends. As used herein with reference to the location of the slot(s) 682 and/or recessed areas 658, 659, the phrase "along the length of the guide rod" or "along its length" may mean generally longitudinally along the central axis of the guide rod, or may alternatively mean a slot formed in any orientation, since the slot and/or recessed areas 658, 659 serve to releasably hold the wire stabilization guides 660 and/or ends 656, 657 of the loop activation wire in place, and one of any number of configurations of slot 682 and/or recessed areas 658, 659 may suffice.

While not necessary to provide operability to the present invention, an opening 804 within the guide rod may be provided to expose a portion of the central guide wire 502. The central guide wire 502 can then be placed over the loop portion 680 of the loop actuation wire 654 to secure the loop to the guide rod until the central guide wire is removed.

The foregoing assumes that the wire forming the loop has a generally circular cross section. However, alternatively other wire shapes may be used, in which case the wire stabilization guides 660 and slot 682 may be mated with the wire 654, in which case the end portions 656, 657 would comprise one or more appropriate corresponding mating components.

Figures 39, 39A:
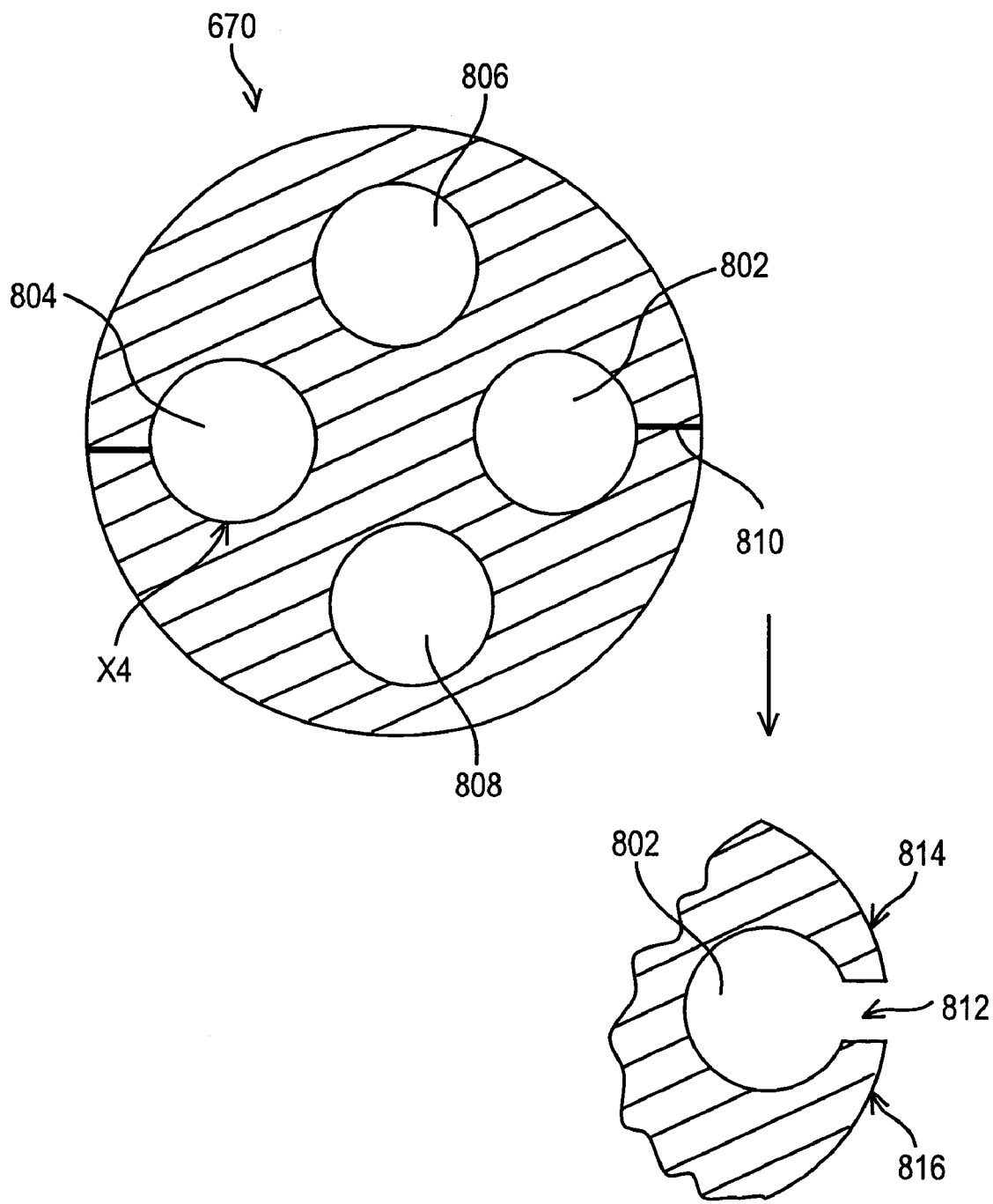
Figure 40:
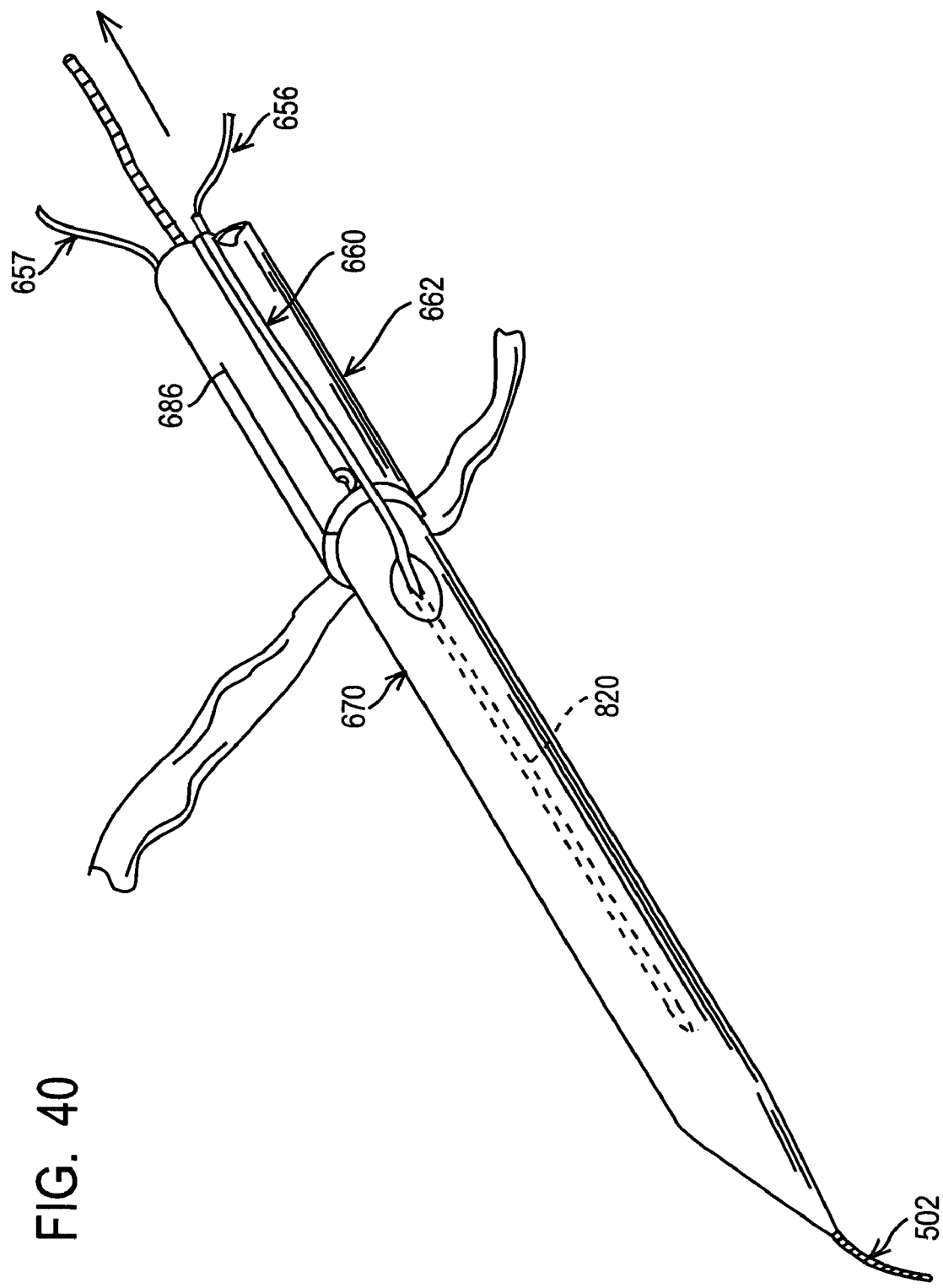

FIGS. 39 and 39A depict cross-sectional views of the guide rod 670 of this exemplary embodiment. The guide rod 670, as depicted in FIG. 40, includes a plurality of lumens: 802, 804, 806 and 808. Lumens 808 and 806 are included as a blood marking passageway (described herein) and a wire guide passageway, respectively. Lumens 806 and 808 are shown adjacent one another, but these lumens could also be formed coaxial with on another (e.g., the wire guide lumen inside of the blood marking lumen). Lumens 802 and 804 releasably hold the loop actuation wire therein, and run along the length of the guide rod, for example, as shown in FIG. 27. Lumens 802 and 804 are shown on opposing sides of the guide rod. But it is equally contemplated that the lumens need not be disposed at opposition, but rather may be formed at any angle with respect to one another. A slit 810 may be provided such that the loop actuation wire is held in lumen 802/804 until outward pressure forces the wire to "pop" out of the slit 810. To that end, the material surrounding the slit may comprise material of reduced durometer (with respect to the rest of the guide rod) such that the actuation wire can slide into and out of the lumen. Alternatively, instead of a slit, a slot may be formed as depicted in FIG. 39A. The slot 812 is defined by truncated lobes 814 and 816. Lobes 814 and 816 may also comprise material of reduced durometer with respect to the remaining portions of the guide rod. Slot 812 can be dimensioned for a particular gage wire inserted therein. Although lumens 804 and 802 are depicted as having generally circular cross-sectional shapes, the present invention equally contemplates other shapes, as may be dictated by the cross-sectional shape of the loop actuation wire (although the cross sectional shape of the wire stabilization guide, loop actuation wire and the lumen need not match).

The use of the foregoing described exemplary introducer 510' will now proceed with reference to FIGS. 27-32. As FIG. 27 illustrates, the introducer 510' is initially inserted into the percutaneous puncture over the central guide wire 502 (already in the artery), which tracks into the puncture site, and is inserted into the artery. Once it has been determined that the distal end of the guide sheath 662 has reached the approximate location of the artery or venous outer wall (via blood marking described herein, or other depth-measuring or locating method known in the art), the central guide wire 502 may be removed from the introducer assembly 510', as shown. As shown in FIG. 28, removing the central guide wire 502 allows the loop activation wire 654 to be released from the guide rod 670 through the longitudinal slots (or slits) 682 within the guide rod 670. This is accomplished by withdrawing the guide rod 670 from the guide sheath 662 as shown in FIGS. 28 and 29. Removing the guide rod from the guide sheath forces the wire stabilization guides 660 (and the loop activation wire within) out of the slots 682 defined in the guide rod by virtue of the force of the end of the sheath on the wire stabilization guides as the guide rod slides proximally out of the sheath, whereupon the loop actuation wire 654 and wire stabilization guides 660 are released to form an open loop, as shown in FIG. 29. The guide rod 670 may then be completely withdrawn from the guide sheath 662.

Figure 30:
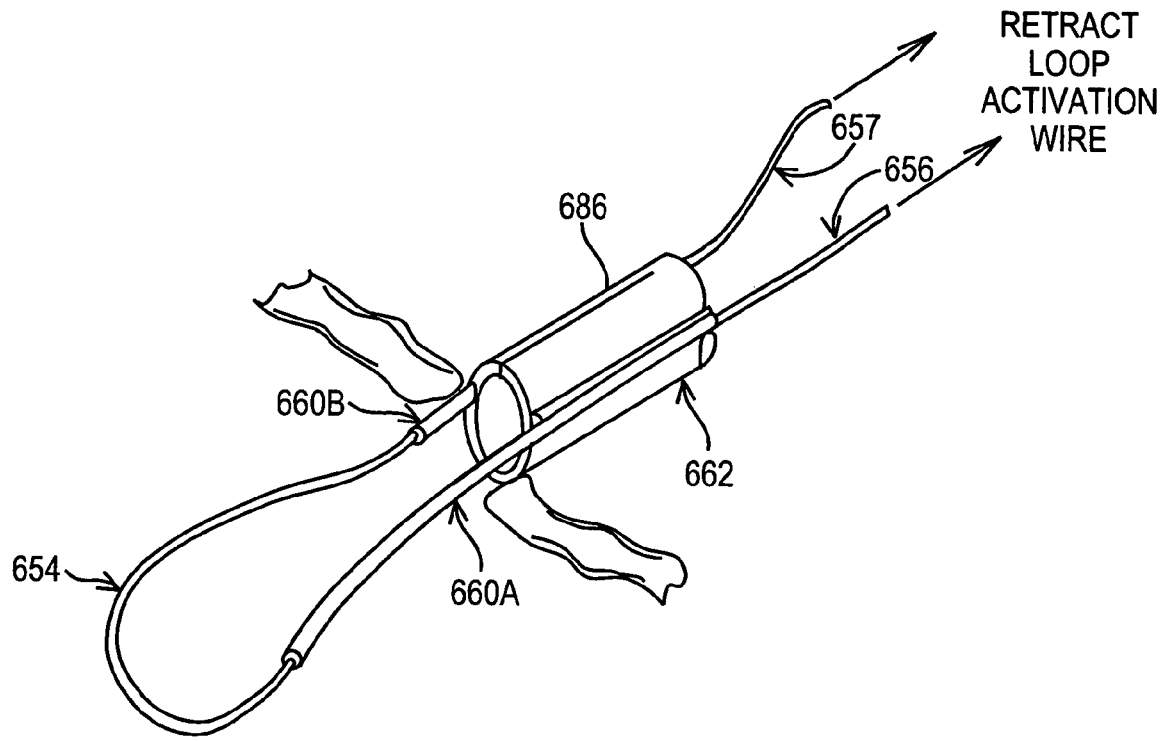
Figure 31:
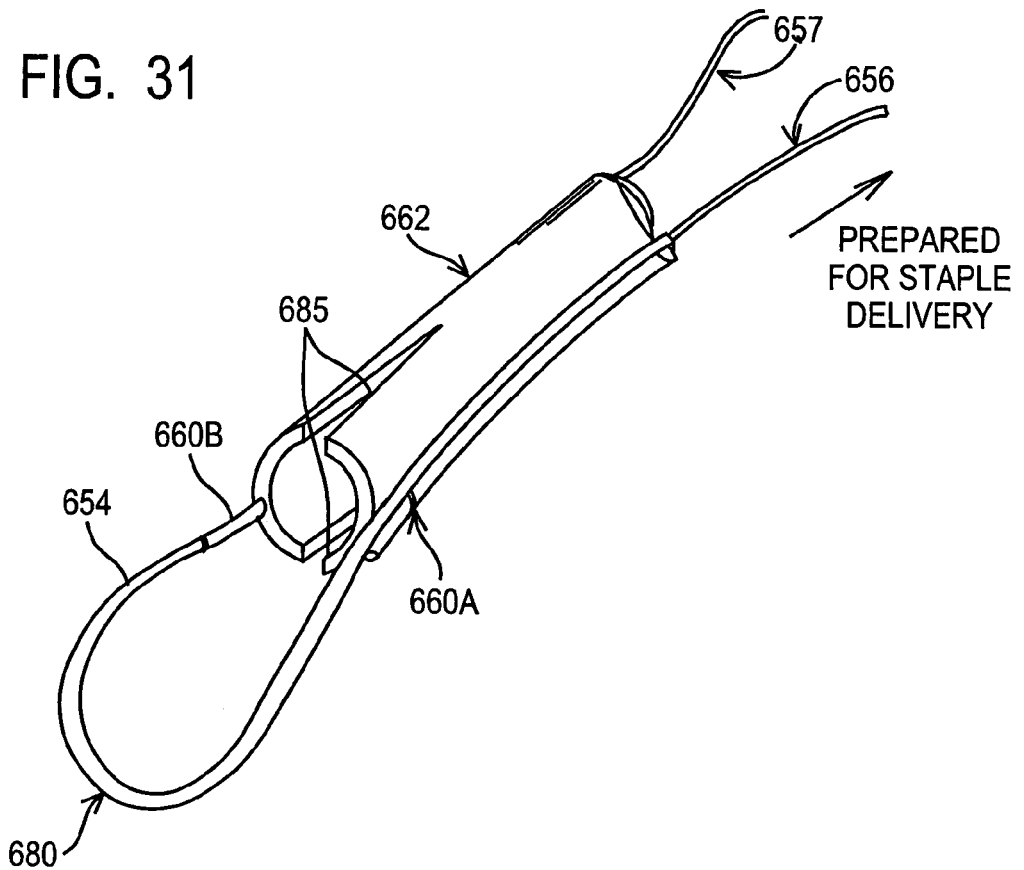
Figure 32:
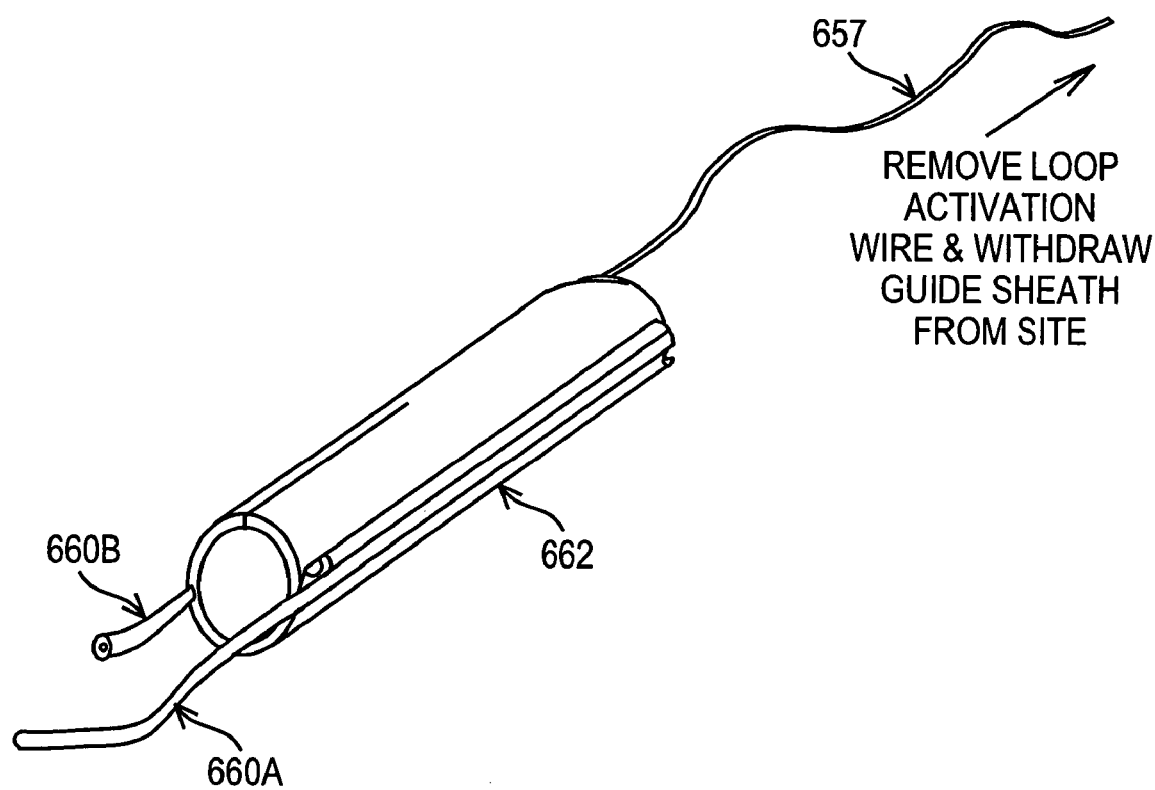

As FIGS. 30 and 31 illustrate, the stabilization guides 660 may be secured and actuated by pulling the loop actuation wire 654 at one or both end portions 656, 657 until the distal ends of the stabilization guides 660A and 660B approximate to form a stabilized loop portion 680. Slits or weakened tear seams 686 may be formed in the distal end of the guide sheath 662 to allow the diameter of the guide sheath 662 to increase when an outwardly radial force is applied to the distal end of the guide sheath 662, for example by the expansion of the loop portion by the loop actuation wire 654 depicted in FIG. 34. The foregoing action provides opposing forces outwardly to the central axis of the guide sheath 662, thereby causing the end of the guide sheath 662 to separate at its slits 686 (or weakened tear seams). Additional clearance for the expansion of a closure device (not shown) within the guide sheath 662 is thus provided. Furthermore, the tissue that is stretched by the stabilization guides 660A and 660B is caused to slide along the newly ramped angles of the stabilization guides 660A and 660B (i.e., the angle created at the junction between the guides 660A and 660B and the distal end of the sheath), thereby urging tissue against the distal end of the guide sheath 662. The foregoing action aids in retaining the guide sheath 662 within the puncture against the vessel. The closure modality (e.g., a staple, as described hereinabove) may next be delivered. As shown in FIG. 32, tension may then be applied to a single end 657 of the loop actuation wire 654 until the wire 654 is completely removed from the stabilization guides 660A and 660B, thereby freeing the distal ends of the stabilization guides 660A and 660B allowing them to slide out of the vessel puncture on either side of the closure device (not shown). Finally, the guide sheath 662 assembly may be removed from the puncture site.

The wire stabilization guides 660A and 660B depicted in FIGS. 30-32 are generally formed as tubular structures having an inside diameter sufficient to pass the wire ends 656, 657 therethrough. The guides 660A and 660B are drawn together (FIG. 31) to form the loop. As a general matter, the wire stabilization guides 660A and 660B in combination with the loop activation wire 654 add to the stiffness of the combined area (680), since it is intended that the closure of the guides causes sufficient outward force to expand the tissue surrounding the wound site in a manner described in detail above. Also, this force may be sufficient to expand the sheath radially by opening the slits or weakened tear seams. Note that the Figures depict wire guide 660A longer than 660B, however, it is not essential that the lengths of the wire guides are as depicted. Rather, the lengths may be selected to be equal or non-equal without departing from the present invention. The positions of the wire guides 660A and 660B are depicted on opposing sides of the sheath. While this arrangement will provide a more accurate centering of the sheath on the wound site, it is contemplated herein that for certain procedures centering on the wound site may not be necessary, critical, or accurate, and thus, the positions of the wire stabilization guides can be at locations about the sheath other than at opposition.

Note also that in the description of the slots in the guide rod to releasably hold the wire stabilization guides, the slots are formed in a location most convenient for placing the wire guides into the slots. Also, the slots may be defined such that one slot releasably holds the wire stabilization guide with the wire inserted therethrough, and the other slot is dimensioned to releasably hold just the wire (as may be the case when the lengths of the wire stabilization guides differ).

Thus, a single or multi-lumen sheath device may be stabilized in direct approximation to an arterial, venous or other lumenal puncture. Advantageously, the foregoing described devices and methodologies allow the positioning of a closure modality centered over such a puncture. The foregoing described introducer assembly 510' allows the distal end of the sheath 662 through which the closure device is introduced to be drawn against the artery, vein or other lumen, thereby aiding in sealing the puncture site to prevent leakage, as well as stabilizing the sheath 662 directly over the wound site.

3. Third Exemplary Introducer

Figure 35:
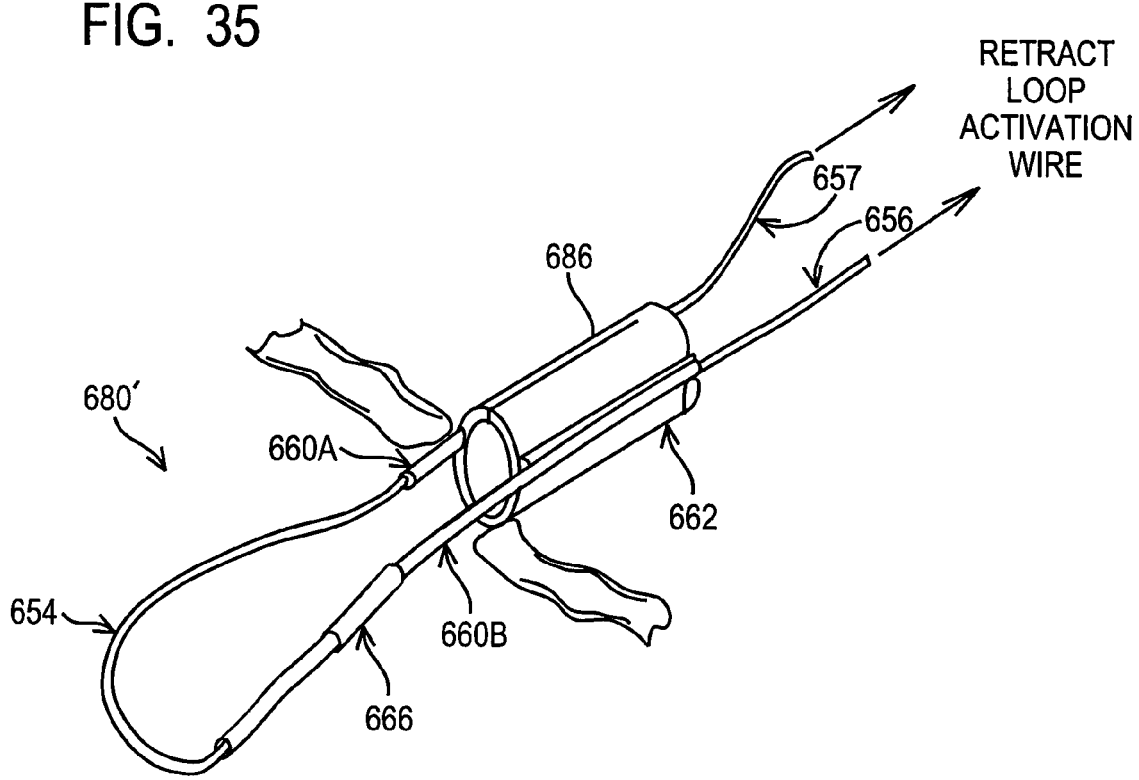
FIGS. 35 and 36 depict isometric views of a third exemplary introducer of the present invention.
Figure 36:
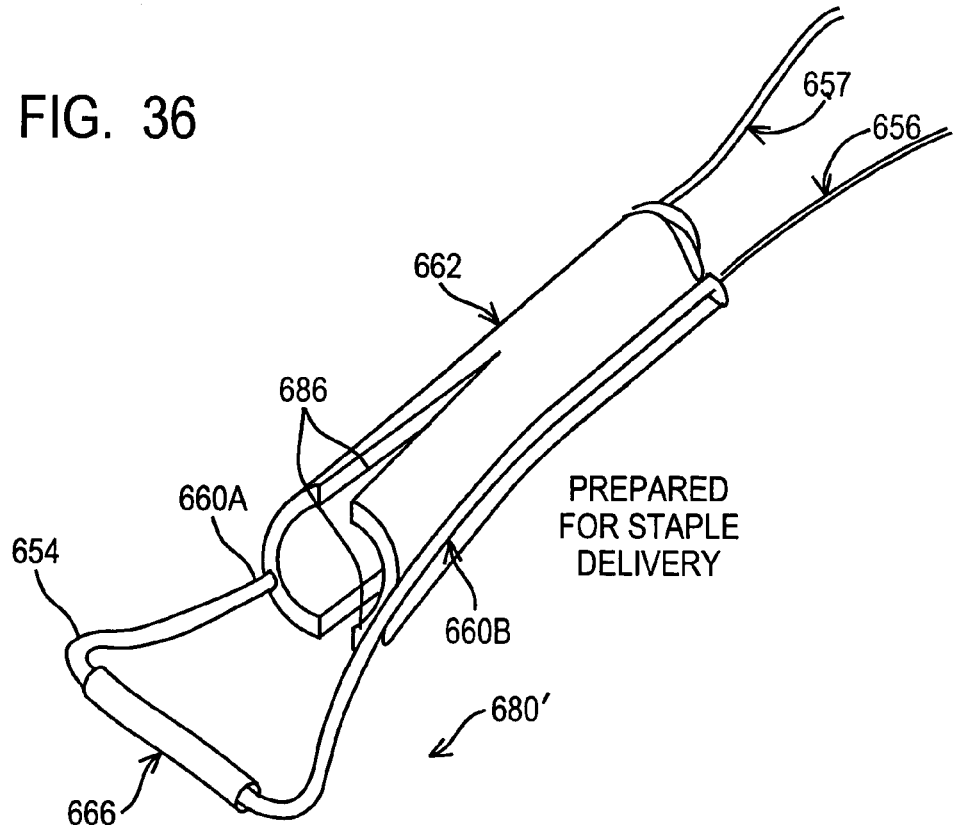

As FIGS. 35 and 36 illustrate, in another embodiment, the foregoing described stabilization loop portion may be replaced with a stabilization loop portion 680' comprising a loop actuation wire 654 having at least one reinforced section 666. The reinforced section may comprise an area of increased material or combination of materials, e.g., a section of the actuation wire 654 or stabilization guide 660A and/or 660B with greater individual or combined rigidity. In this configuration, the location of the reinforced section 0.666 may be manipulated with respect to the wound site to control the shape of the stabilization loop portion 680'. The stabilization guides 660A and 660B may be secured and actuated by pulling the loop actuation wire 654 at one or both end portions 656, 657 until the distal ends of the stabilization guides 660 approximate to form a stabilization loop portion 680' which comprises the reinforced section 666, the central axis of which is generally perpendicular to the central axis of the guide sheath 662, thereby providing opposing forces outwardly perpendicular to the central axis of the guide sheath 662 and causing the end of the guide sheath 662 to separate at its slits 686. As shown in FIG. 36, the loop portion and reinforced section forms a shape with the general appearance of a coat hanger. Additional clearance for the expansion of a closure device (not shown) within the guide sheath 662 may likewise be provided.

As in the previously described embodiment, the tissue which is stretched by the stabilization guides 660A and 660B is caused to slide along the newly ramped angles of the stabilization guides 660A and 660B and be forced against the distal end of the guide sheath 662. The foregoing action aids in retaining the guide sheath 662 within the puncture against the vessel. The closure modality (e.g., a staple, as described hereinabove) may next be delivered. As shown in FIG. 32, tension may then be applied to a single end 657 of the loop actuation wire 654 until the wire 654 is completely removed from the plurality of stabilization guides 660, thereby freeing the distal ends of the stabilization guides 660 and allowing them to slide out of the vessel puncture on either side of the closure device (not shown). Finally, the guide sheath 662 assembly may be removed from the puncture site.

4. Fourth Exemplary Introducer

FIGS. 40-45 depict another exemplary embodiment of the introducer of the present invention. In this embodiment, the wire stabilization guides are modified to include intralumenal support for procedures being performed at the vascular puncture site such as closure of the puncture or an anastomosis procedure. FIG. 40 depicts a similar introducer as is shown in FIGS. 27-32, except in this exemplary embodiment the wire stabilization guides 660A and 660B comprise a retention device 820 formed along a portion of the guide.

Figure 43:
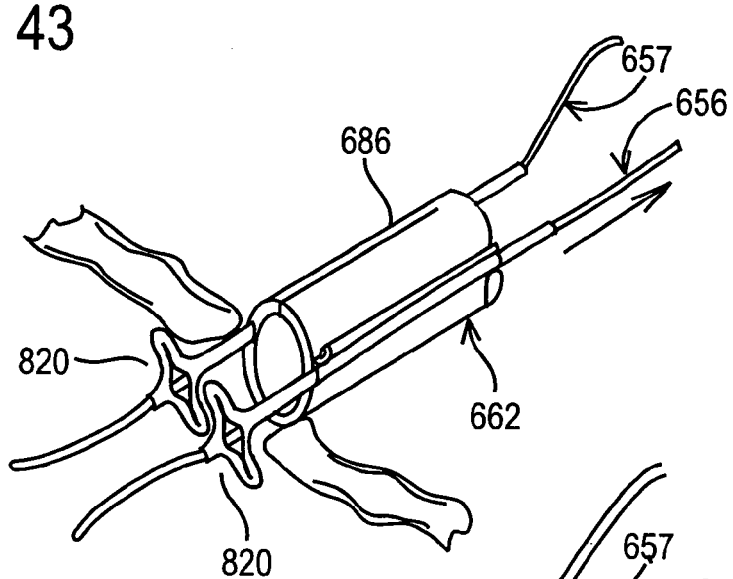

The tissue retention device 820 is generally provided herein to secure the distal end of the sheath to the tissue, e.g., to the arterial wall about the wound site. Deployment of the retention device is depicted in FIGS. 41-45. As in the previous embodiments, the wire stabilization guides 660A and 660B are deployed by moving the guide rod 670 with respect to the sheath 662. The retention device 820 is formed along the length of the wire stabilization guide at a predetermined distance from the end of the sheath. One utility of the retention device 820 is to ensure the sheath 662 remains located on the wound site, so a predetermined distance of the retention device from the end of the sheath may be chosen, for example, in accordance with the thickness of the tissue in which the device is deployed. FIG. 43 depicts the sheath, stabilization guides and retention devices in a deployed position. In this exemplary embodiment, the retention devices 820 formed on each stabilization guide secures the sheath to the arterial wall to prevent transverse movement of the sheath with respect to the wound site.

Figure 44A:
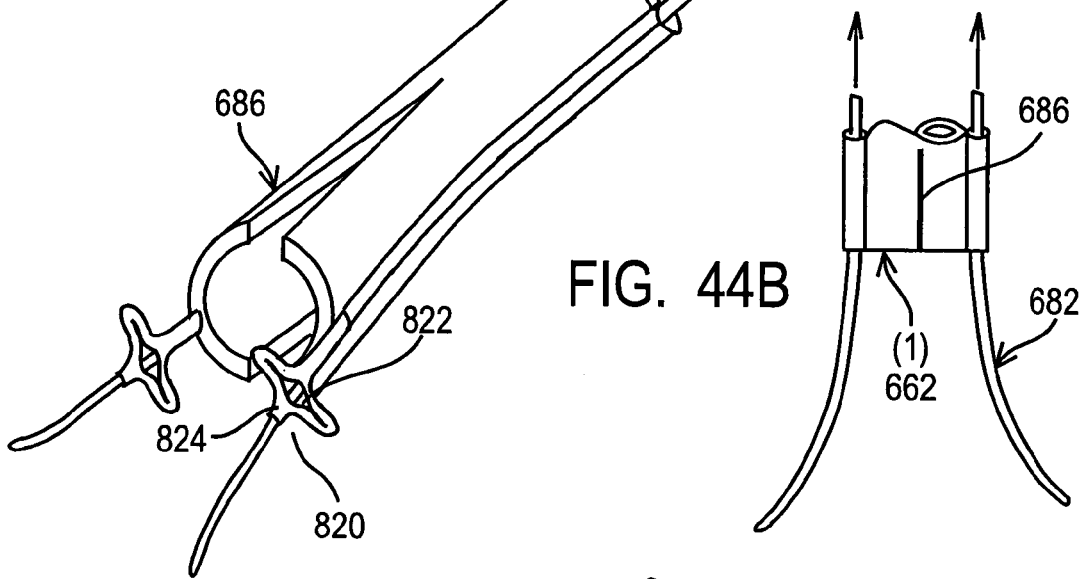
Figure 44B:
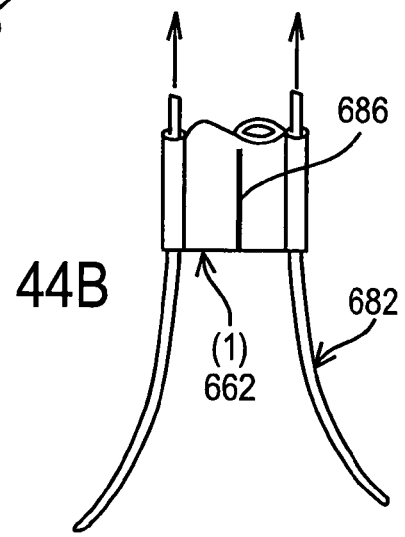
Figure 45:
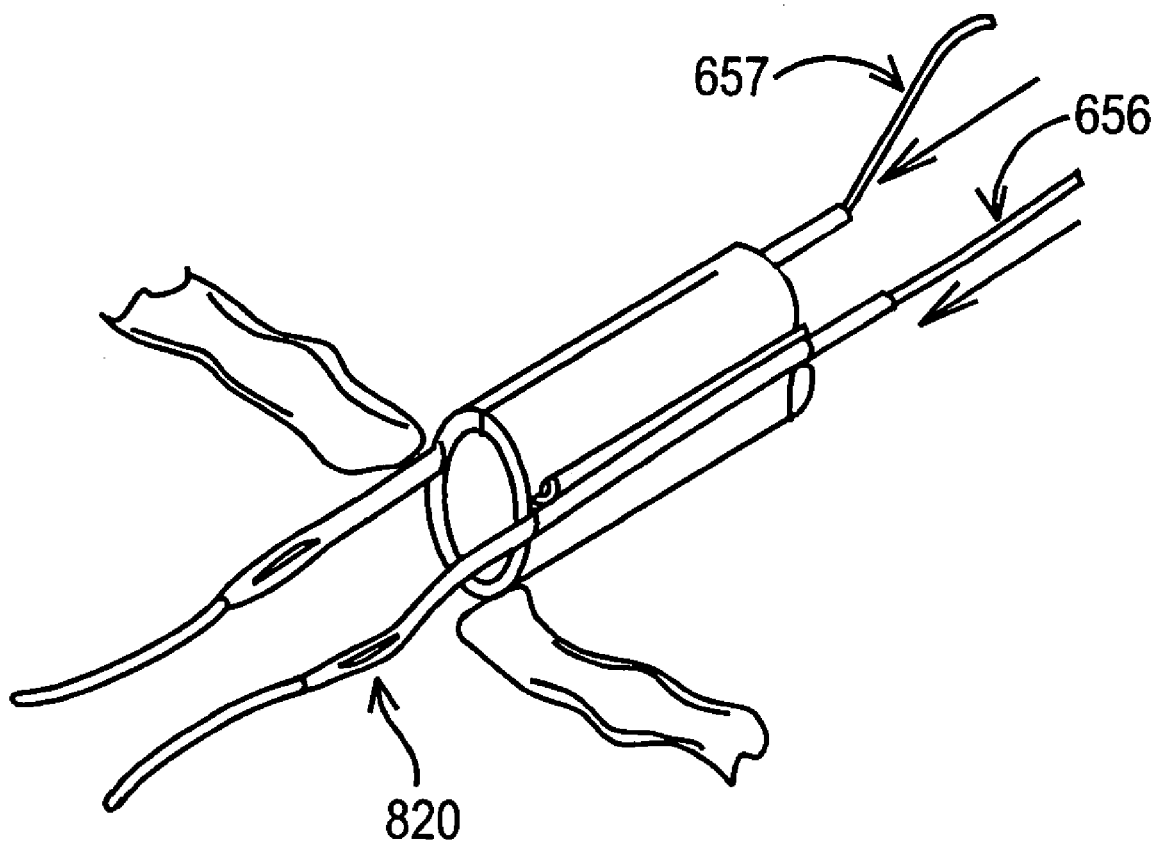

The retention device 820 of this embodiment is essentially an expanding portion of the wire stabilization guide. To that end, FIGS. 42, 43 and 44A depict the retention device deployed into the expanded position. The retention device 820 is formed by a split 822 on each side of the stabilization-guide 660. The loop actuation wire is affixed to the wire stabilization guide, for example, at point 824. To deploy the retention device, the (656 and/or 657) of the wire are pulled proximally, thus causing the distal end of the wire stabilization guide to be drawn proximally, and causing the retention device to compress and buckle at the split sections (by placing a tensile load on the stabilization guide). To release the retention device, the wire is moved distally, thereby releasing tension on the stabilization guide, as shown in FIG. 45.

Figure 44C:
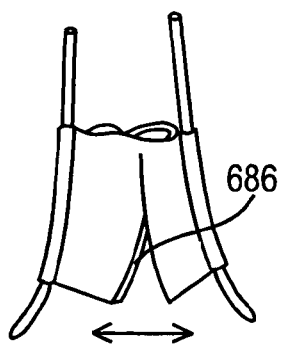

Returning again to FIGS. 44A and 44C, compression on the stabilization guide to form the retention device may also be used to expand the distal tip of the sheath at the slits or weakened tear seams 686, as shown in the relaxed position (FIG. 44B) and expanded position (FIGS. 43A and C). Optionally, the stabilization guides 660A and/or 660B may be of a more rigid nature and preformed in the configuration shown in FIG. 44B. Drawing the stabilization guides 660A and/or 660B in a proximal direction would cause an expansion of the distal tip of the sheath (FIG. 44C).

Figure 46:
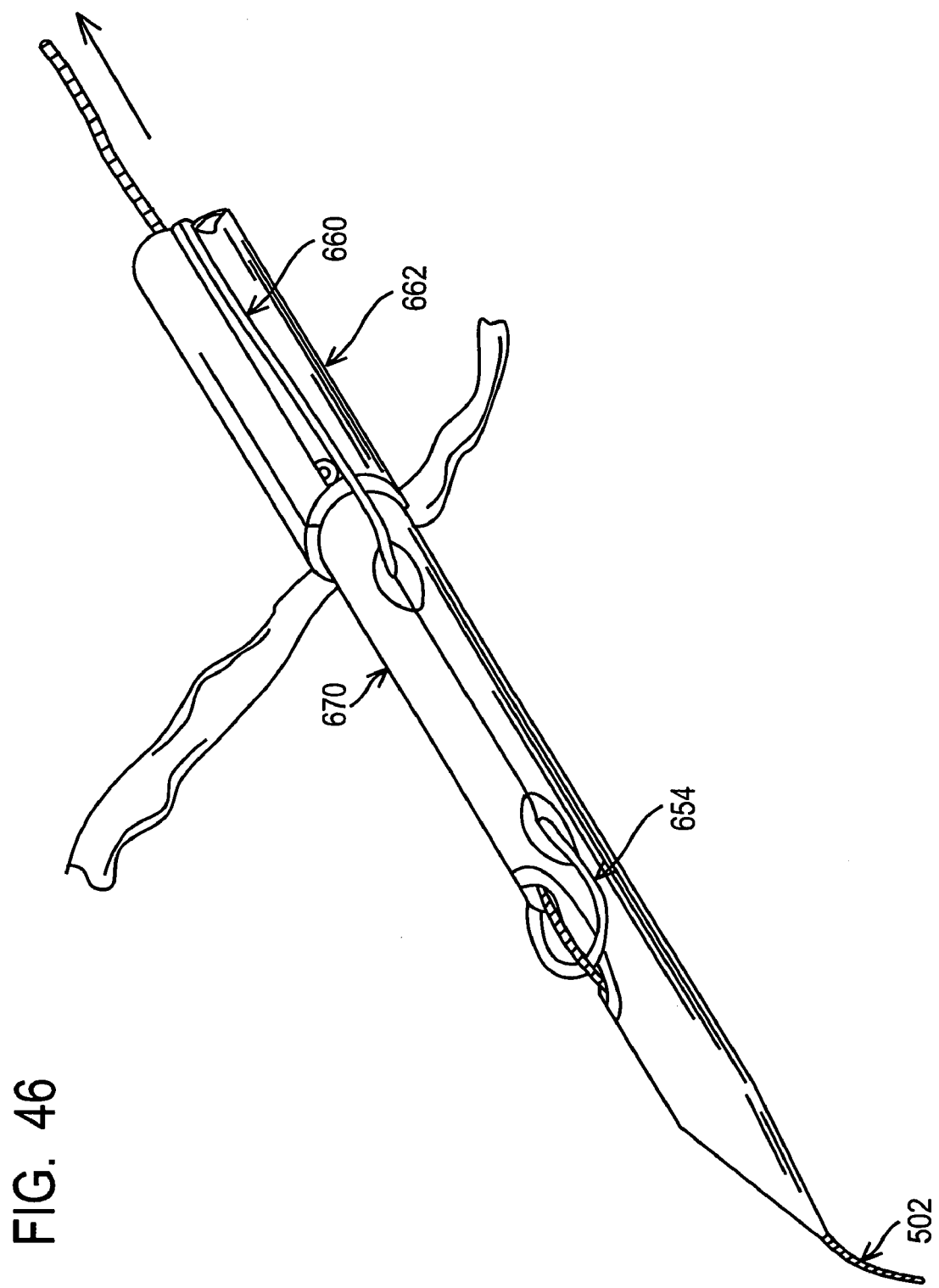
Figure 47:
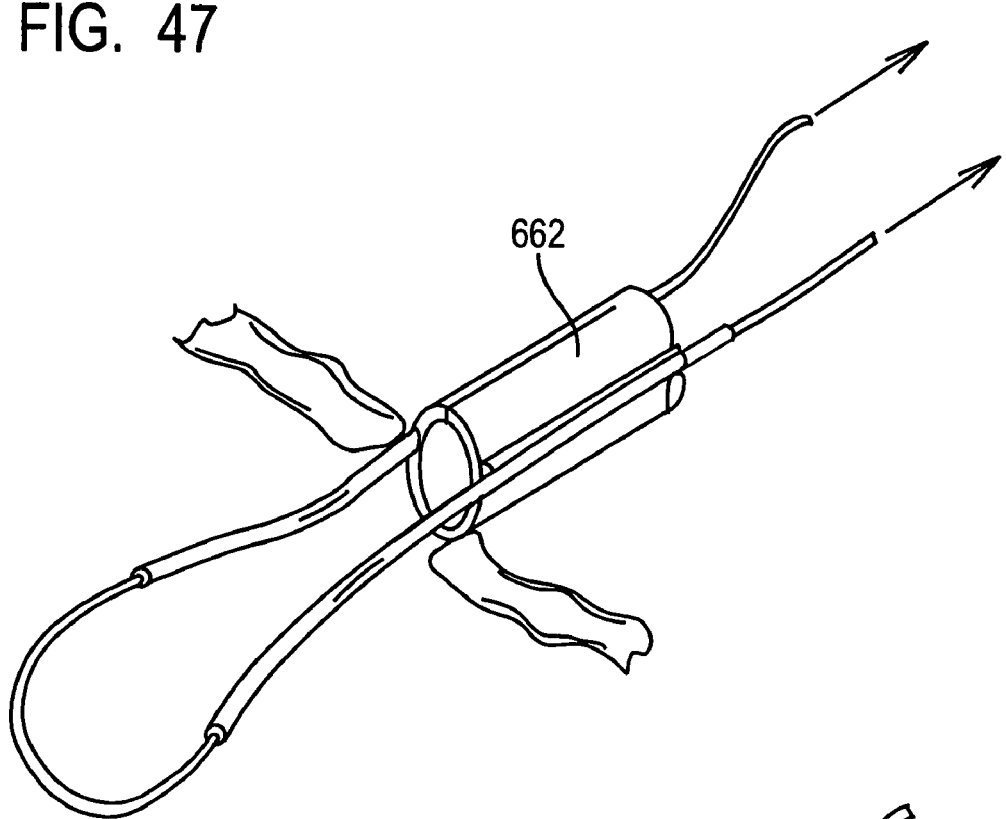
Figure 48:
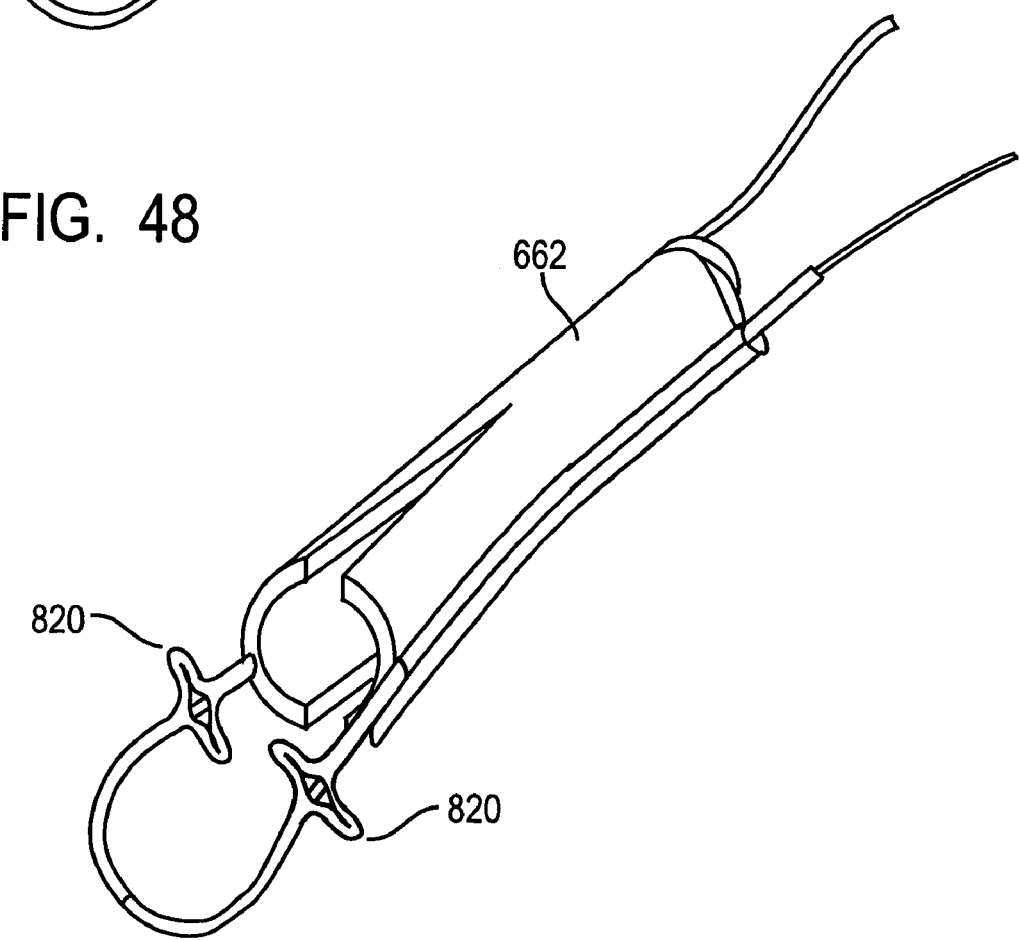
Figure 49A:
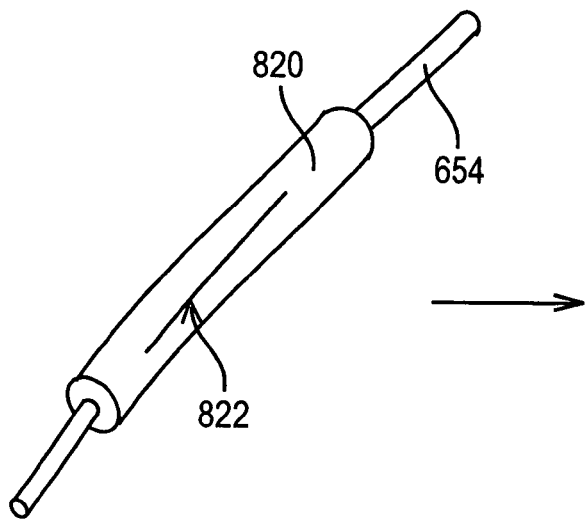
Figure 49B:
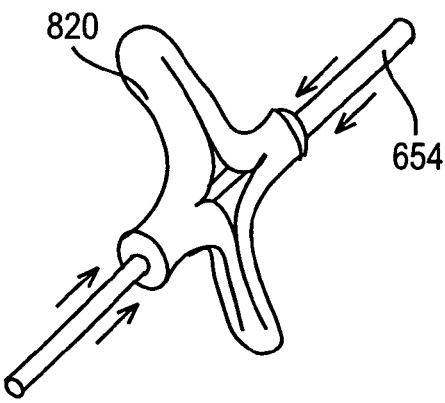

FIGS. 46-48 depict yet another exemplary embodiment of the introducer of the present invention. This embodiment is similar to the embodiment of FIGS. 27-32 and FIGS. 35 and 36, except in this exemplary embodiment the loop actuation wire comprises a retention device 820 formed along a portion of the guide. In this embodiment, the loop actuation wire forms a single loop, with a retention device 820 positioned on one or both wire stabilization guides adjacent the sheath. Other features depicted in the Figures are the same as the previous embodiment, described above.

Figure 50A:
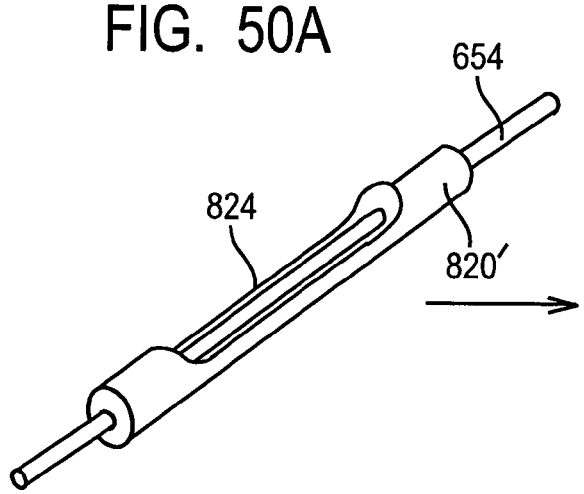
Figure 50B:
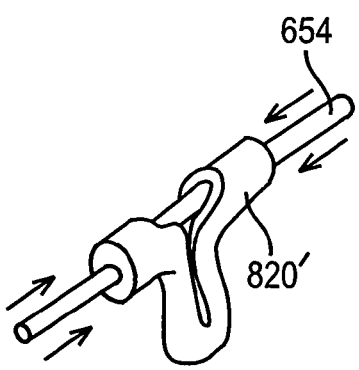
Figure 51A:
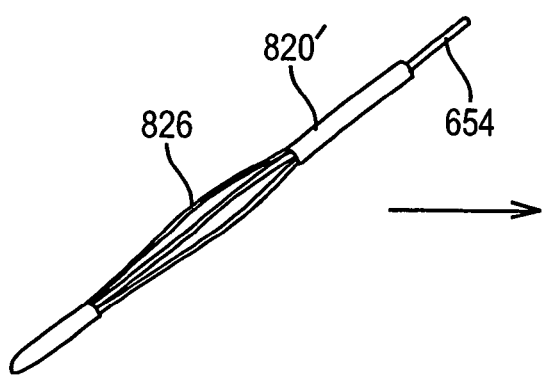
Figure 51B:
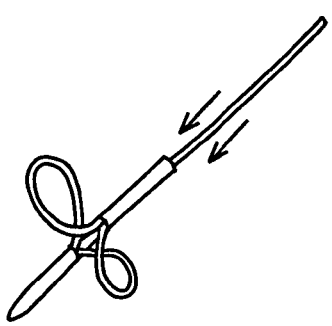
Figure 52C:
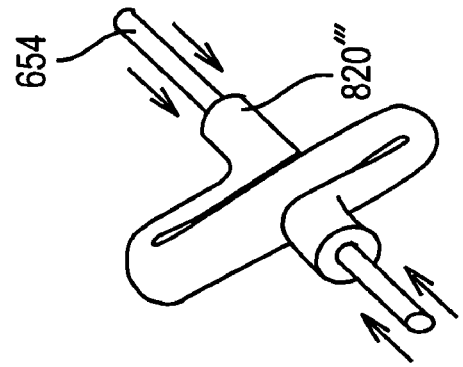
Figure 52B:
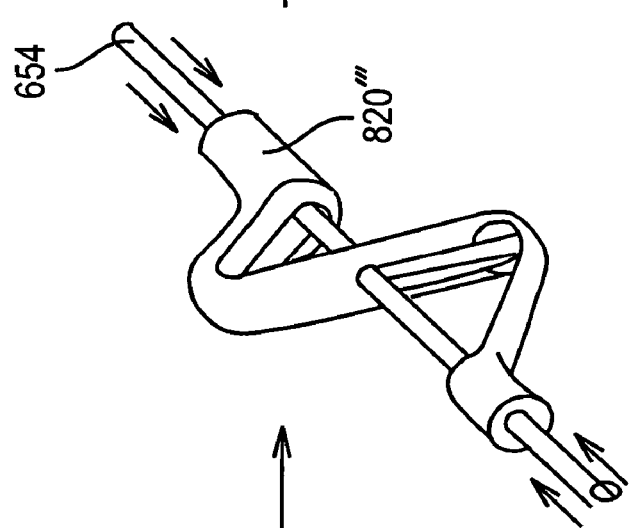
Figure 52A:
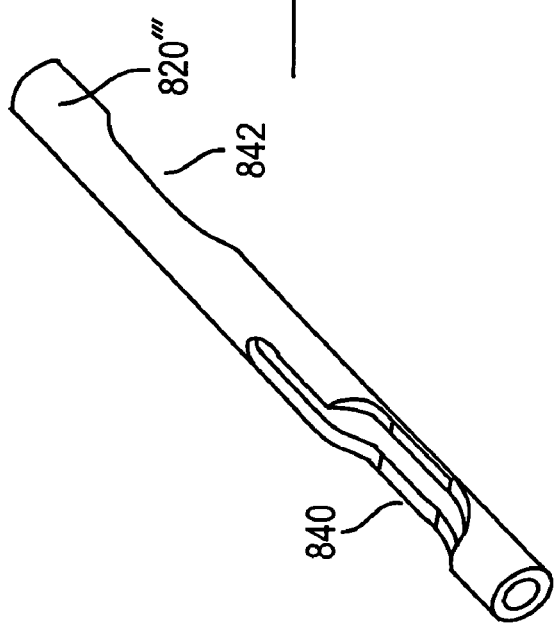

FIGS. 49-57 depict numerous exemplary embodiments of the retention device of the present invention The retention device 820 in each of the figures is depicted in partial cutaway view, showing the stabilization guide 660 and wire 654. FIG. 49A and 49B depict detailed views of the retention device 820 of the previous embodiment in the relaxed (static) and deployed positions, respectively. In FIG. 50, the retention device 820' comprises a tubular member with a hollowed out notch portion (or skive) 824 formed along the length thereof. Compression of the tubular member causes the material opposite the notch to collapse thereby forming the retention device (FIG. 50B). In FIG. 51, the retention device 820'' comprises a tubular member with a plurality of filaments 826 that fold (upon compression) to form the retention device. In this case, a small loop is formed. Alternatively, a buckle (not shown) is formed having a U-shape that does not form a complete loop. In FIG. 52, retention device 820''' comprises a tubular member with generally symmetrical notches (or skive) on either side, 840 and 842, with slots emanating from the notches which overlap approximately midway between the notches. The slots overlap forming a through-hole approximately equal to the inside diameter of the tube. The cross section of the tube in the area of the slot is that of a U-shaped beam. Compression causes the tubular member to fold at the notched sections 840 and 842, fulcruming on the wire at the location where the slots overlap, as shown in FIGS. 52B and 52C.

Figure 53A:
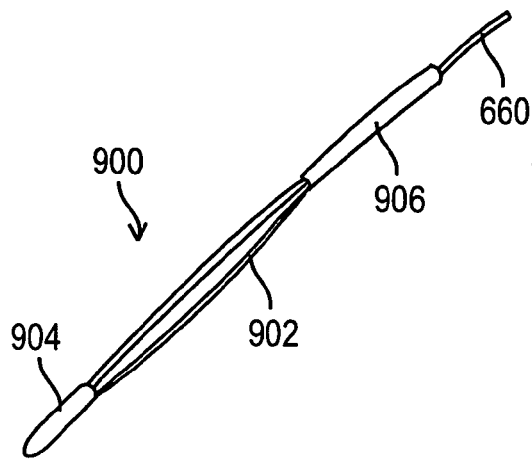
Figure 53B:
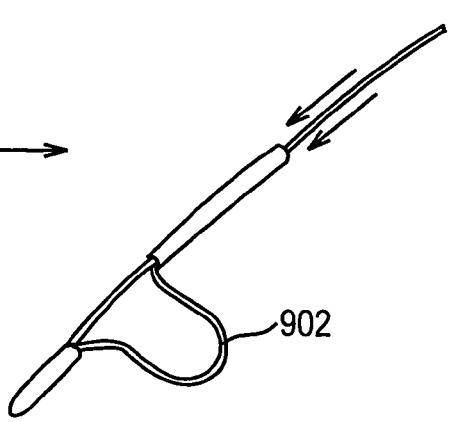
Figure 54A:
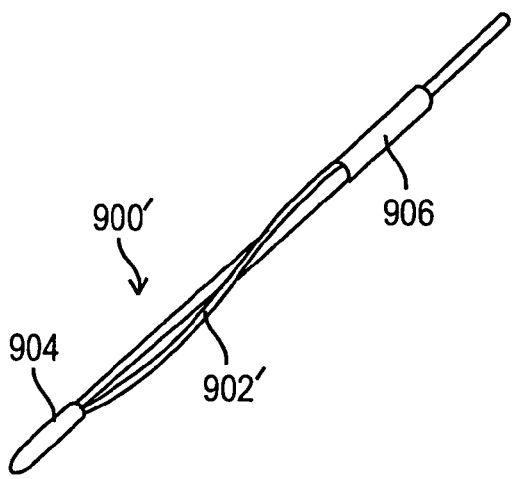
Figure 54B:
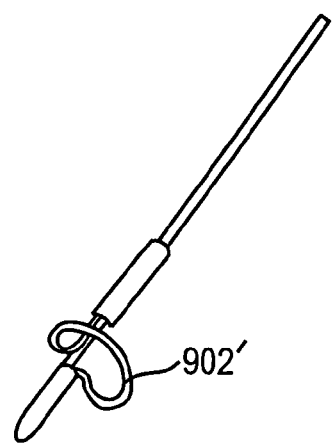
Figure 55A:
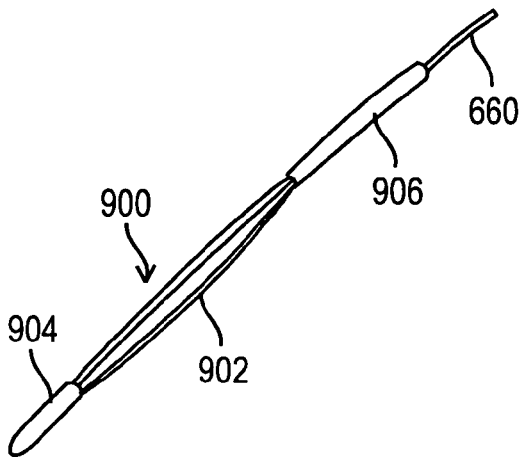
Figure 55B:
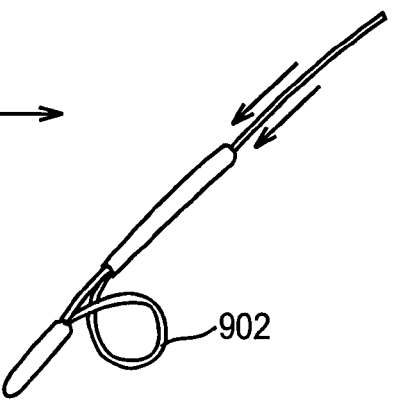
Figure 56A:
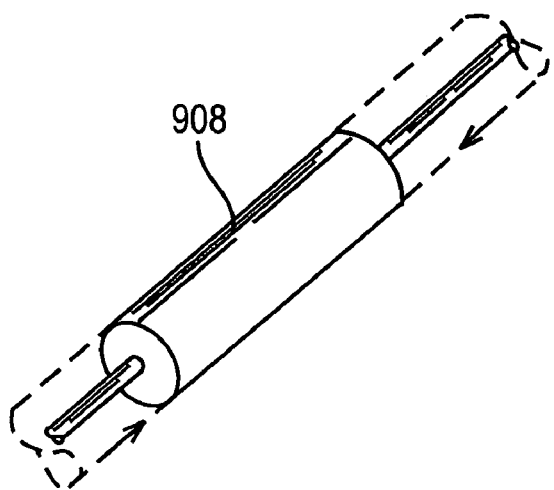
Figure 56B:
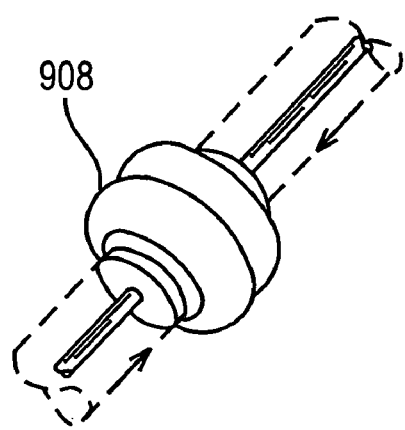
Figure 57A:
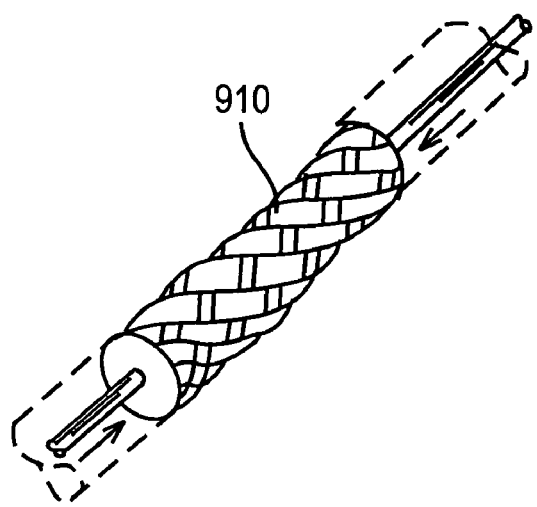
Figure 57B:
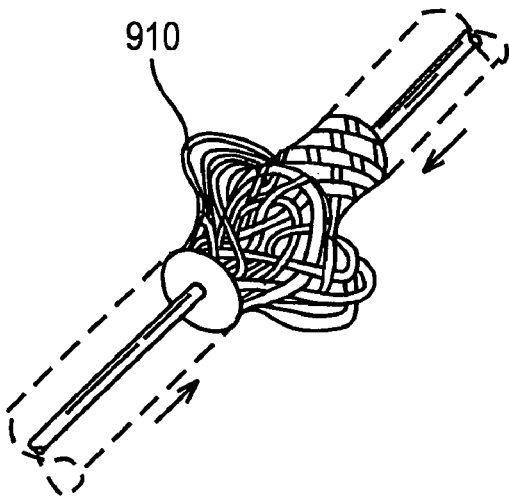

FIG. 53 depicts yet another exemplary embodiment of a retention device 900 that is similar to the example shown in FIG. 51, except the retention device 900 comprises a single strand member 902 between a stationary member 904 and a moveable member 906. The moveable member 906 is moved over the wire guide 660 towards the stationary member 904 buckling the strand 902, as shown in FIG. 53B. Similarly, in FIG. 55 the moveable member 906 is brought closer to the stationary member 904 to form a loop from the strand 902. In the retention device 900' of FIG. 54, the strand 902 is disposed off-line (i.e., off axis) between the stationary member 904 and the moveable member 906 (FIG. 54A). Movement of the moveable member 906 forms a loop as shown in FIG. 54B (the loop in FIG. 54B is somewhat distorted as compared to the loop of FIG. 55B). FIGS. 56A and 56B depict another exemplary retention device that utilizes a resiliently deformable member 908 that is compressed along the axis of the wire thus causing expansion of the member 908 in the plane substantially normal to the wire. FIG. 56B depicts expansion in all direction in the plane normal to the wire, however, the expansion in all directions is not necessary. FIGS. 57A and 57B depict an expanding mesh retention device 910. In this embodiment, mesh is formed by a plurality of individual strands which expand outwardly upon compression (as indicated by the arrows).

In the embodiments of FIGS. 40-57, the retention device of the present invention may be viewed as an extension or lobe formed on one or both stabilization guides, or, in the case of the loop structure of FIGS. 46-48, the retention device may be formed on opposing sides of the loop, as shown. The retention device examples of FIGS. 49-57 are intended to apply to both the embodiments of FIGS. 40-45 and/or 46-48. The orientation of the retention device with respect to the wire stabilization guide or loop is depicted as generally perpendicular thereto, but the retention device may be formed from greater than 0 degrees to less than 180 degrees from wire stabilization guide or loop and still work as intended. The present invention covers all such alternatives. The orientation of the retention device with respect to the wound opening is depicted, for example in FIGS. 43, 45 and 47, as being generally perpendicular to the long axis of the wound. However, this angle is not a requirement of the present invention, but rather the retention device can be disposed at any angle with respect to the long axis of the wound.

Figure 58:
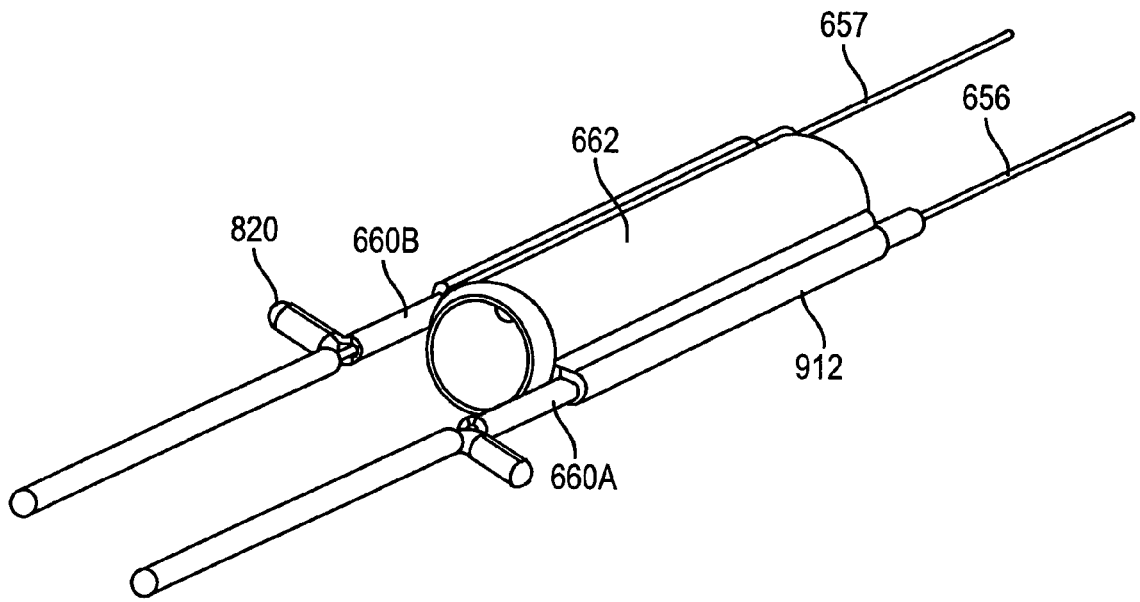
Figure 59:
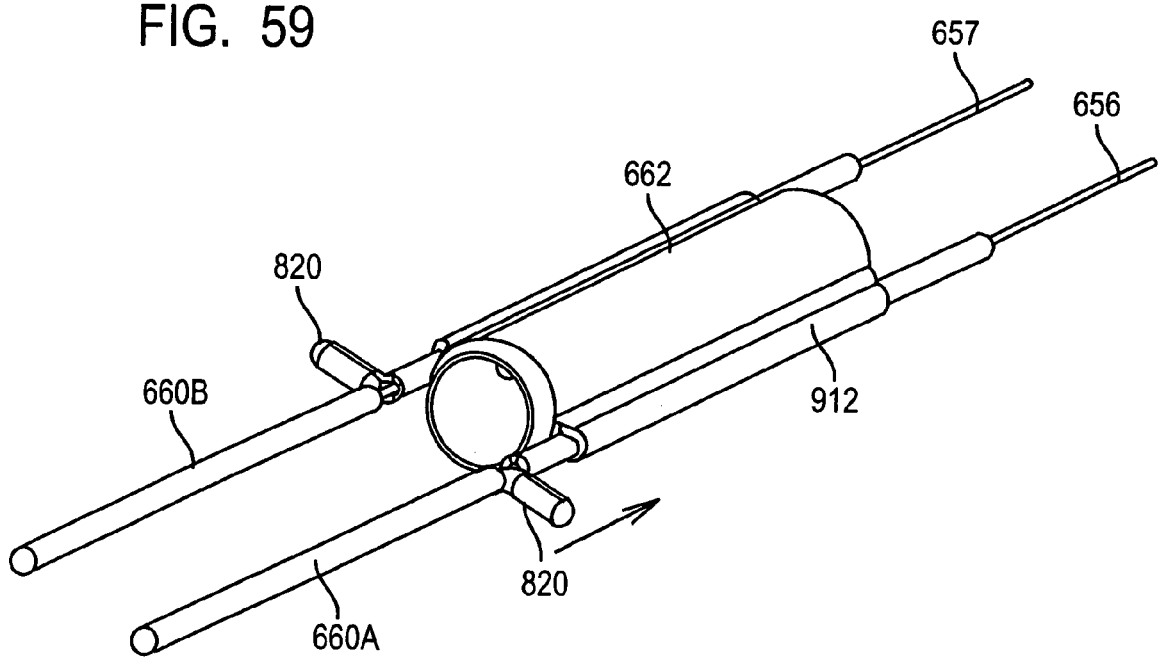

FIGS. 58 and 59 depict yet another exemplary embodiment of the retention device applicable to any of the devices shown in FIGS. 40 through 48. In this example the wire guides 660A and 660B are slidably disposed within cannulated members 912, respectively, on the sheath. Members 912A and 912B are attached to the sheath, as shown. This configuration permits the wire guide and the retention device to be drawn proximally, i.e., closer to the distal end of the sheath. Such a slidably disposed wire stabilization feature may be created with any of the retention devices represented in FIGS. 49 through 57, or any equivalent thereof 5. Fifth Exemplary Introducer Referring now to FIGS. 60-66, a fifth exemplary introducer 1000 is depicted. The introducer of this embodiment can incorporate any of the previously-described guide rod and sheath devices, and further includes additional components set forth below. This embodiment depicts the introducer 1000 during its use at a wound site, and thus also depicts another exemplary wound site management methodology according to the invention. For clarity, like components described above (for example, the sheath, dilator, wire guide, retention device, stapler, staple etc.) are numbered differently in the embodiment of FIGS. 60-66 from the previous embodiments; however, it should be understood that these components are interchangeable with any of the previously-described components.

Figure 60:
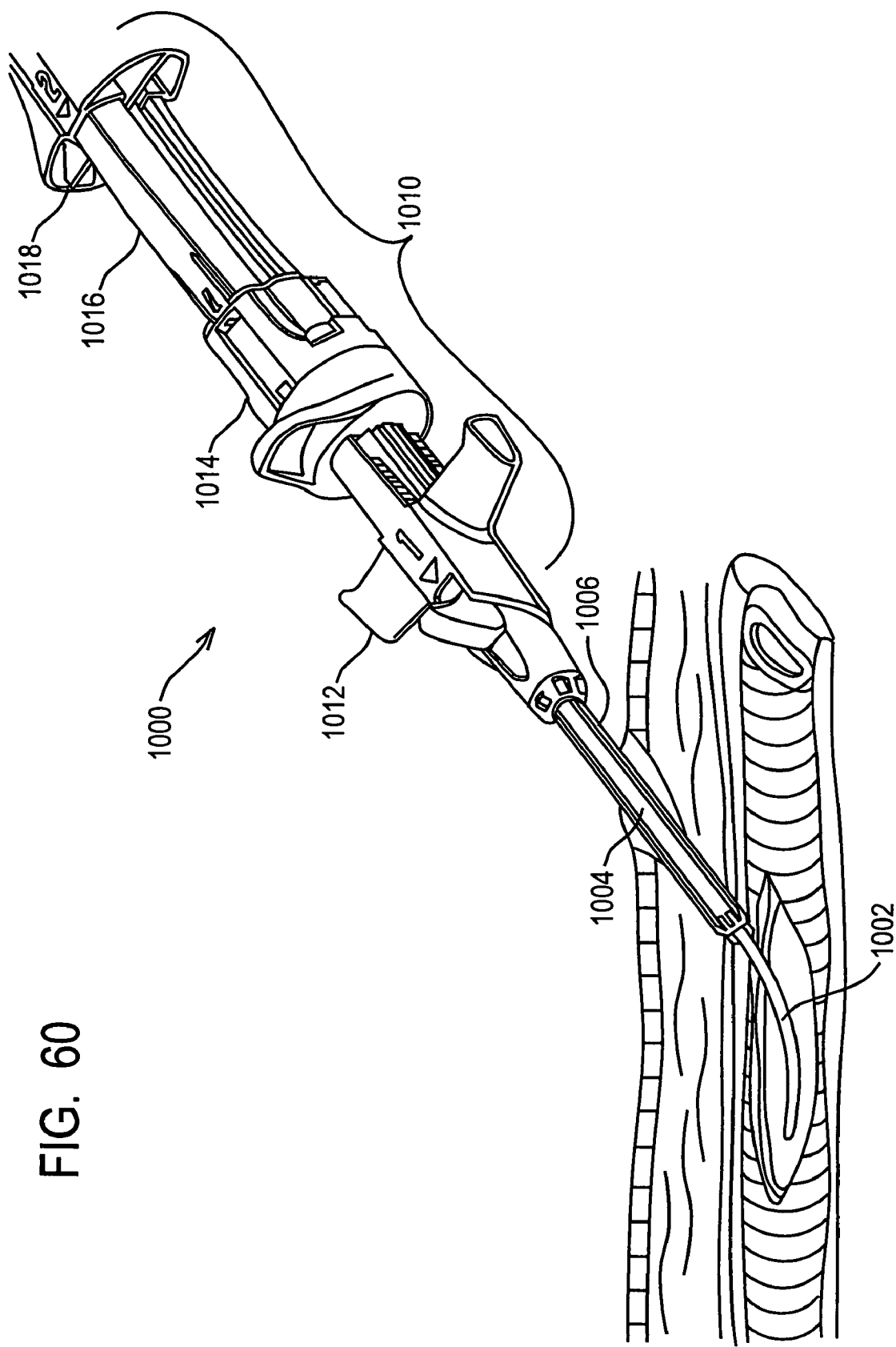

The introducer 1000 comprises a guide rod 1002, a sheath 1004 with a transition sheath 1006 covering at least the distal end of the sheath 1004, and an actuator portion 1010 comprising a transition sheath retractor 1012, a receiver 1014, a dilator slide 1016 and a dilator handle 1018. The dilator handle 1018 is slidably disposed on the dilator slide 1016. The retractor 1012 is slidably disposed on the sheath 1004 and receiver 1014 which are fixedly attached. The transition sheath 1006 is provided to smooth and protect the juncture between the distal end of the sheath 1004 and the guide rod 1002. The transition sheath is provided so that when that portion of the device is urged through the skin and superficial fascia (as depicted in FIG. 60), the transition sheath reduces the tendency of snagging on tissue.

Figure 61:
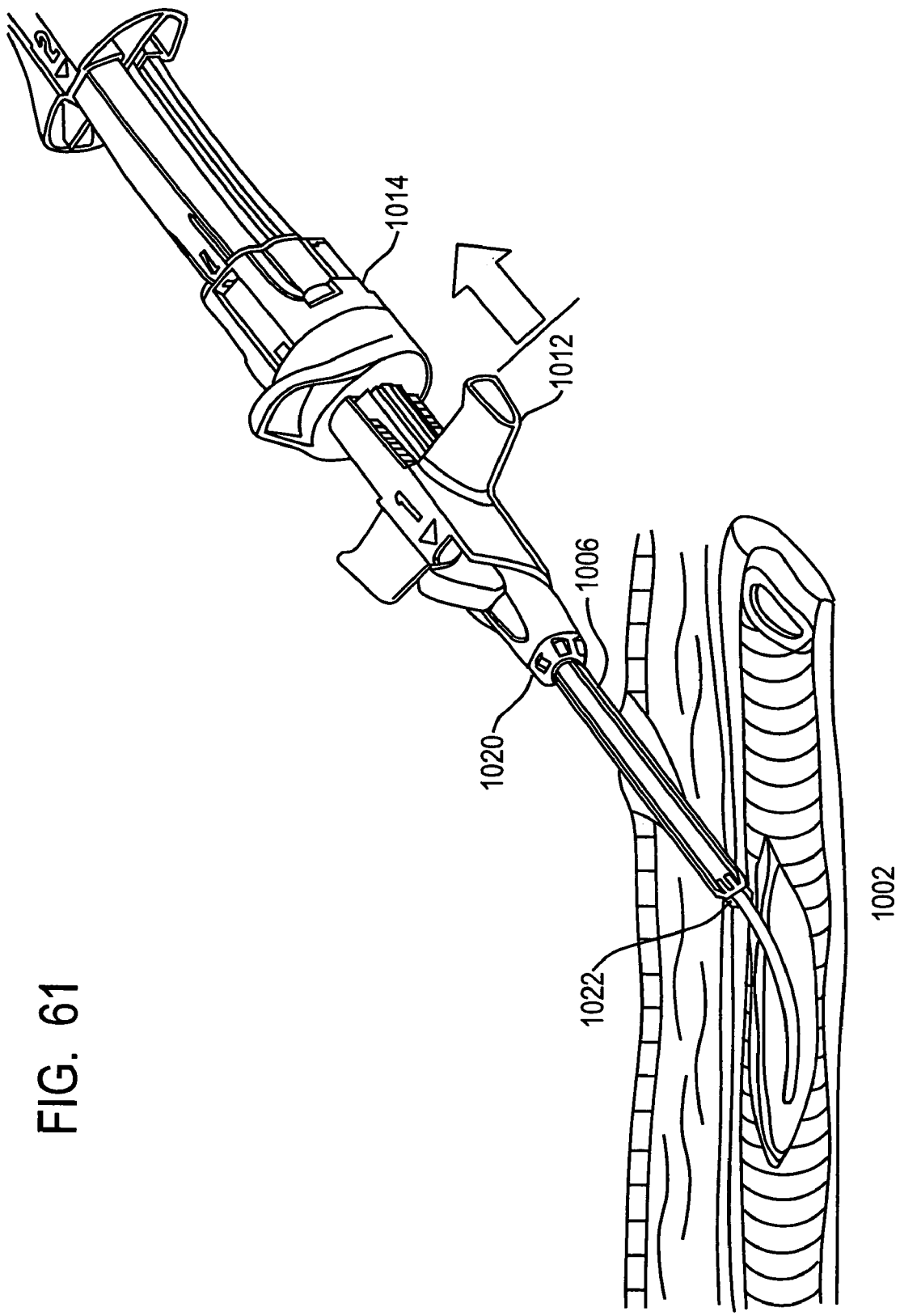

The sheath 1004 (and transition sheath 1006), transition sheath retractor 1012, receiver 1014 and dilator slide 1016 are generally tubular members that provide access therethrough to the wound site at the distal end of the sheath, as will be explained below. Referring now to FIG. 61, once the dilator tip is within the vessel (as may be determined by one or more blood marking passageways associated therewith as described herein) and the distal end of the sheath is in close proximity to the vascular wound site, the transition sheath is retracted to expose at least a portion of the distal end of the sheath To do so, the sheath retractor 1012 is moved proximally with respect to the receiver 1014 (as indicated by the arrow). The transition sheath 1006 is attached to the sheath retractor 1012 at, for example, joint 1020. The transition sheath is slidably disposed over the sheath 1004, and thus moving the transition sheath in this manner exposes the distal tip 1022 of the sheath 1004.

Figure 62:
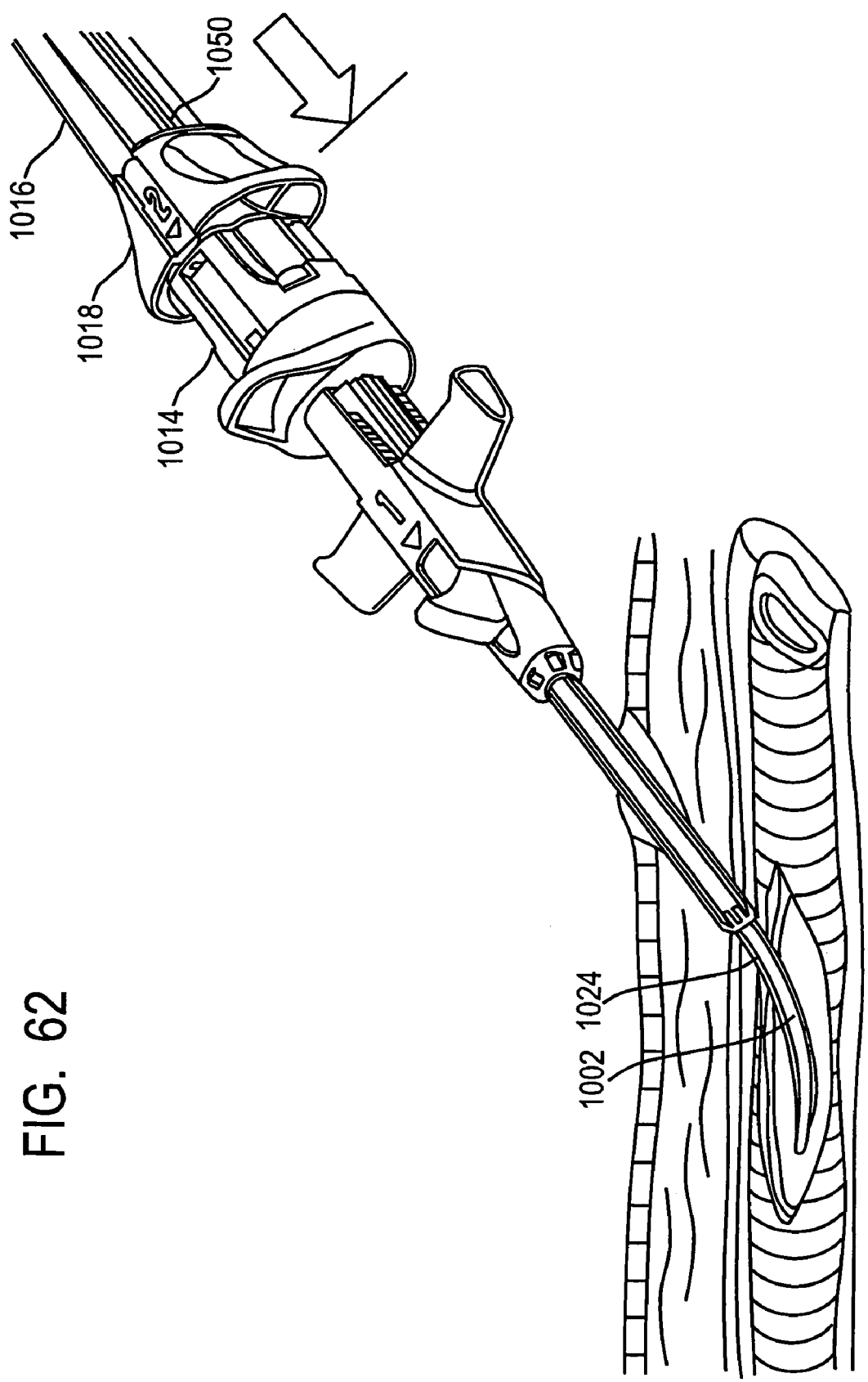

In this exemplary embodiment, the dilator 1002 is housed within the actuator portion 1010. In FIG. 62, the dilator 1002 is urged distally (i.e. further into the artery) by sliding the dilator handle 1018 distally over the dilator slide 1016. Within the dilator slide, the dilator 1002 abuts against the dilator handle, so that as the dilator handle is moved so does the dilator. To facilitate this action, a slot 1050 is defined along the length of the slide 1016, and a tab portion (not shown) of the handle 1018 extends into the slot and contacts the proximal end of the dilator (also not shown) housed within the slide 1016. Moving the dilator 1002 distally further into the vessel also exposes the wire guides 1024 that are removably affixed within the dilator (e.g., by the same manner as described in the previous embodiments). As the handle 1018 is moved distally, a finger protruding from the distal surface of the handle 1018 and into the receiver 1014 also activates a mechanism contained within the receiver 1014 which causes the retention devices 1026A and 1026B (FIG. 63) to be deployed within the vessel. This action is effected by drawing the wires disposed within the wire guides, thereby creating a retention device as is detailed above. The retention devices 1026A and 1026B operate to grip the inside wall of the artery and draw the sheath 1014 towards the arterial wall to stabilize the wound site, in a manner described above.

Figure 63:
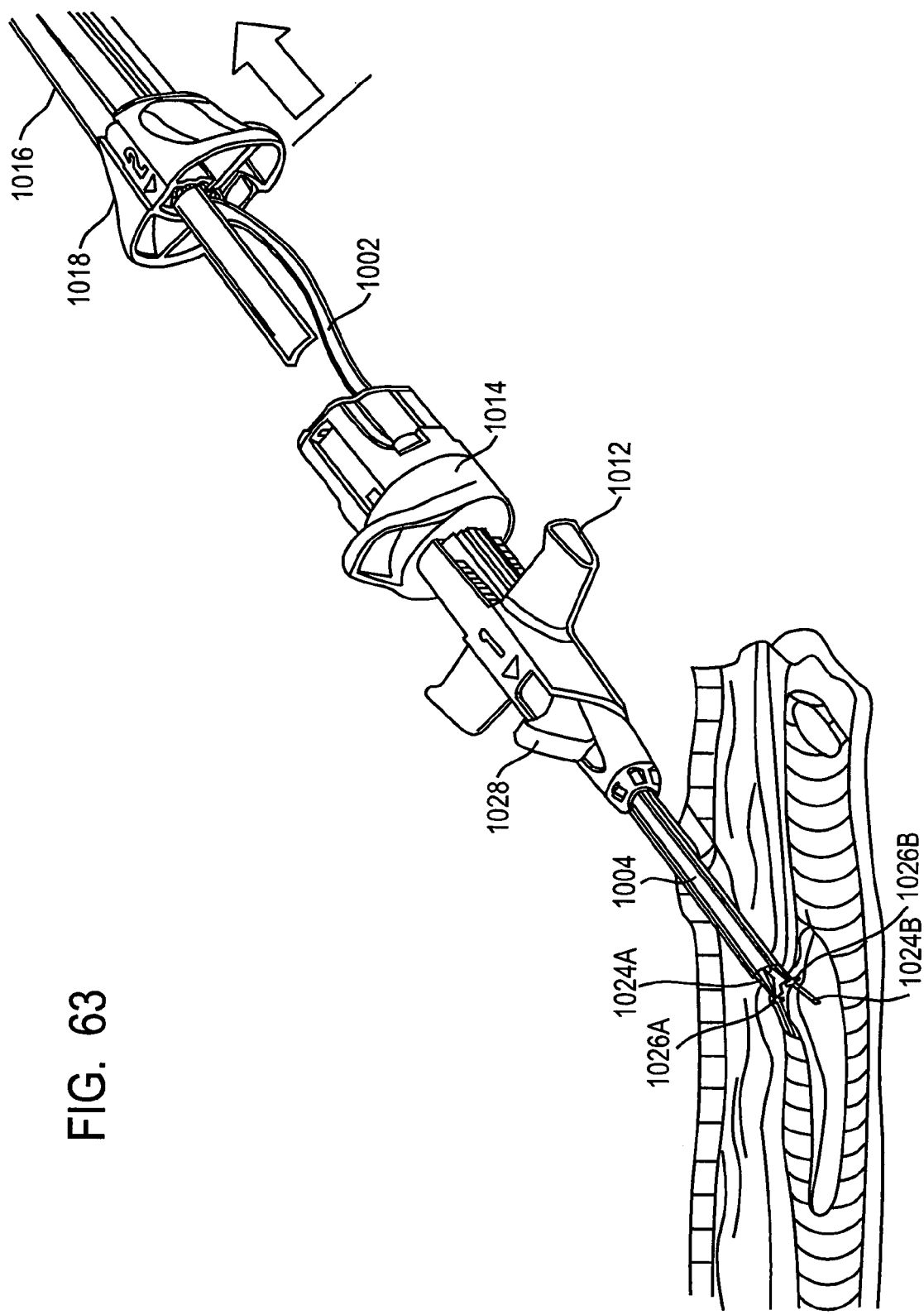

In FIG. 63, the slide 1016, handle 1018 and dilator are removed from the remaining portions of the introducer. In this exemplary embodiment, the handle 1018 and slide 1016 are removed by drawing these components proximally from the receiver 1014. By removing the dilator 1002, the retention devices 1026A and 1026B retract proximally toward the sheath 1004 to grip the tissue located between the retention feet and the sheath. A retention device actuator lever 1028 is provided to manually retract retention devices 1026A and 1026B (associated with each wire guide 1024A and 1024B, respectively).

Figure 64:
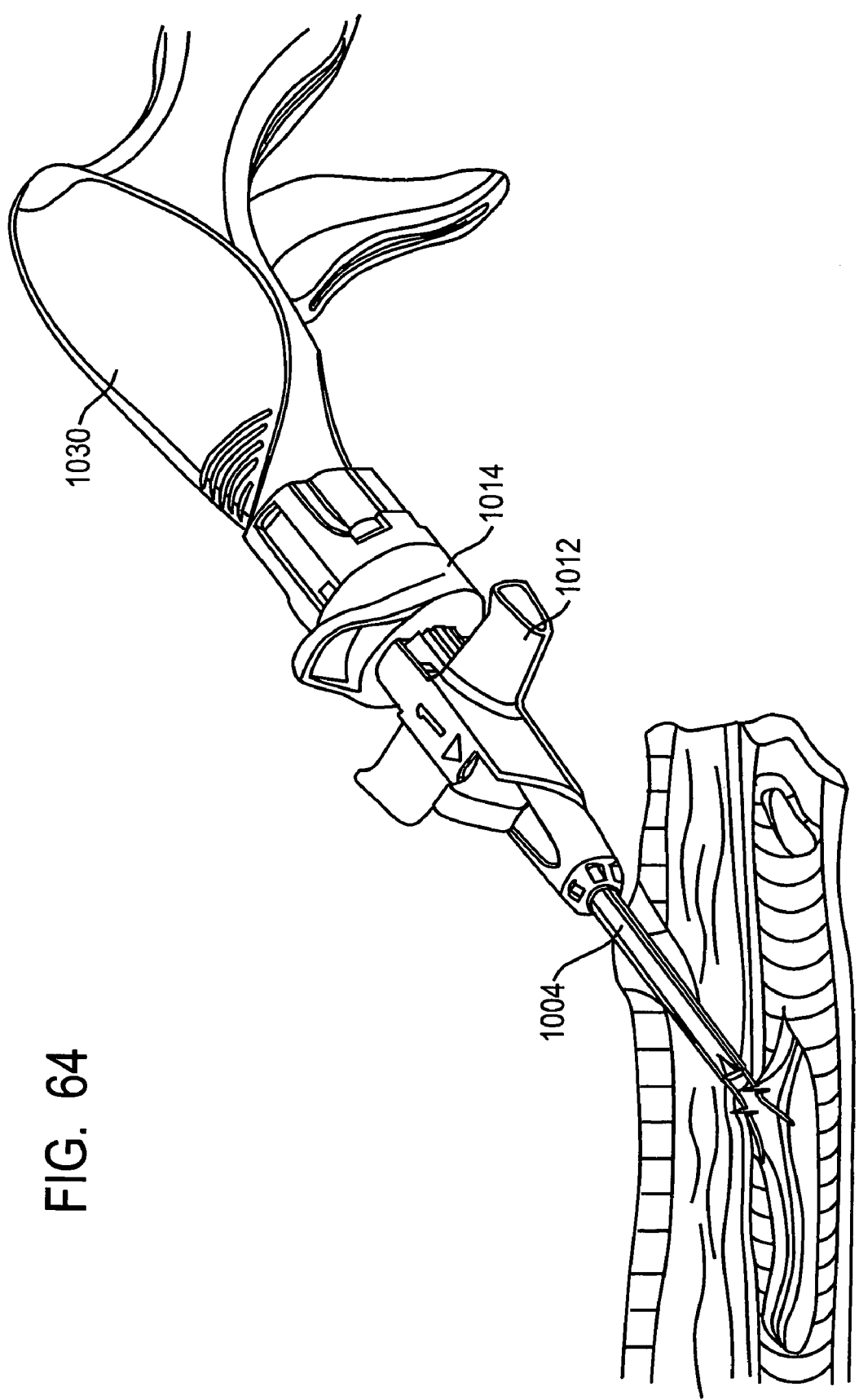

FIG. 64 depicts a closure device 1030 inserted into the tubular structures of the receiver 1014, the sheath retractor 1012 and sheath 1004, once the dilator is removed as described with reference to FIG. 63. The closure device can be a stapler as set forth in the description of FIGS. 7-17 of the present invention, or other tissue closing device such as a tissue clip delivery device and/or other stapler known in the art. FIGS. 65 and 66 depict details of staple delivery, and further details of the distal tip of the sheath. In FIG. 65, the stapler 1030 is inserted down through the remaining portions of the introducer to the wound site. FIG. 66 shows the area around the wound site in greater detail. In this exemplary embodiment (and assuming the transition sheath 1006 is retracted proximally as described above) the distal tip of the sheath 1004 includes a plurality of slots 1038A and 1038B. The slots expose the prongs of the staple 1036 which is deployed into the tissue. Recall from the above-description of the staple and stapler that the prongs of the staple are designed to expand outwardly, pierce the vessel wall, and then fold inwardly to close the wound. Lever 1032 (FIG. 65) of the stapler 1030 performs this function, and is described in detail above. After the staple is deployed, the retention devices 1026A and 1026B are released, and the entire device (including wire guides 1024A and 1024B) is removed.

6. Blood Marking

Figure 33:
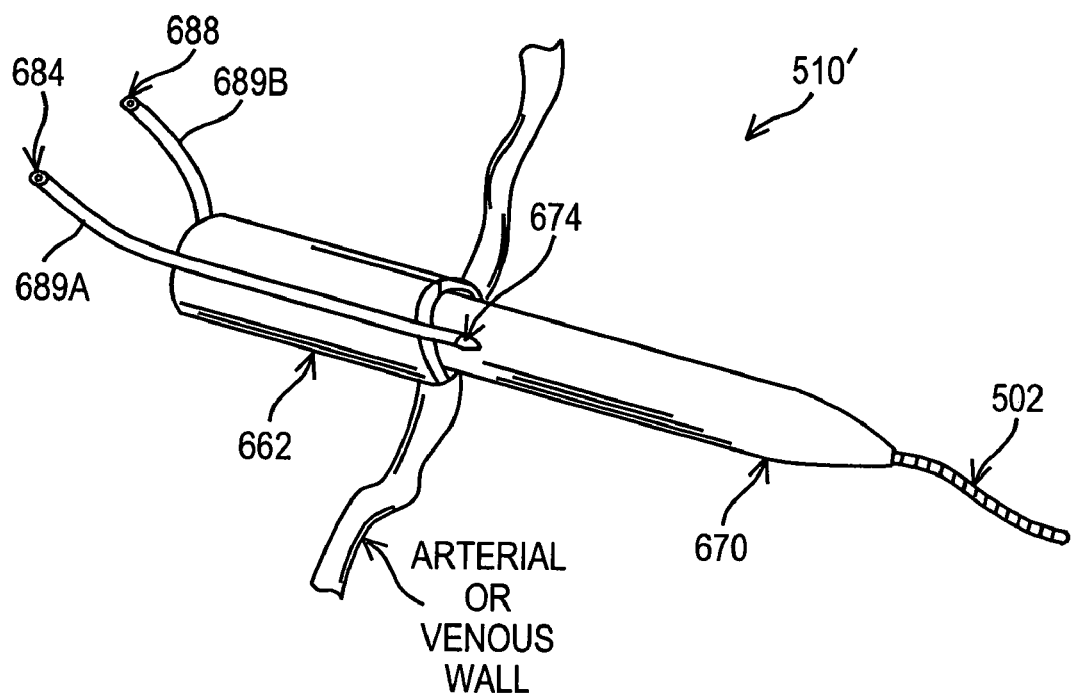
Figure 34:
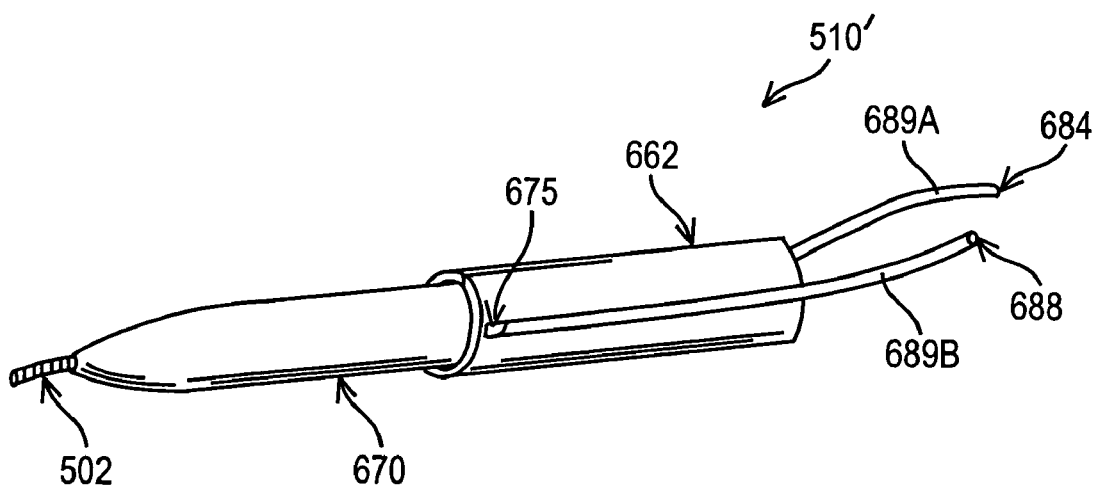

The following description of identifying insertion depth of a transluminal device applies to any of the introducer embodiments described herein. Blood marking lumens may be provided with the sheath, the guide rod (dilator), or both. FIGS. 33 and 34 show blood marking lumens associated with the sheath 602. As shown, two "flash back" blood marking lumens 689A and 689B are fixedly attached to the guide sheath 662. At the distal end of the first blood marking lumen 689A is an intraluminal blood marking port 674 located at a predetermined point in relation to the distal end of the sheath. The proximal end of the first blood marking lumen 689A is an interluminal flashback port 684 for observing the presence of blood at the intraluminal blood marking port 674. At the distal end of the second blood marking lumen 689B is a blood marking port 675 located approximately at the distal end of the guide sheath 662, and the proximal end of the second blood marking lumen is an extraluminal flashback port 688 for observing the presence of blood at the extraluminal blood marking port 675.

In operation, the introducer assembly is introduced into the percutaneous puncture which tracks into the puncture site, as described hereinabove. The location at which the guide sheath 662 has reached the approximate location of the artery or venous outer wall may be identified by observing the pressurized blood flow from the internal flashback port 684, which enters the internal blood marking port 674 when the internal blood marking port 674 has reached the inner lumen of the vessel. The absence of pressurized blood flow observed at the internal flashback port 684 indicates that the guide sheath 662 has not yet reached the vessel outer wall or that the internal blood marking port 674 has not reached the inner lumen of the vessel. The fact that the guide sheath 662 has not entered the inner lumen of the vessel may be confirmed by the absence of pressurized blood flow observed at the external flashback port 688. Blood flow would enter the extraluminal blood marking port 675 only if the extraluminal blood marling port 675 has reached the inner lumen of the vessel. Likewise, presence of blood in this lumen indicates the guide is too far into the artery or vein. The presence of pressurized blood flow at the internal flashback port 684 and absence of pressurized blood flow at the external flashback port 688 indicate that the distal end of the guide sheath 662 is sufficiently inserted into the wound site and adjacent to the arterial or venous outer wall.

Figure 37:
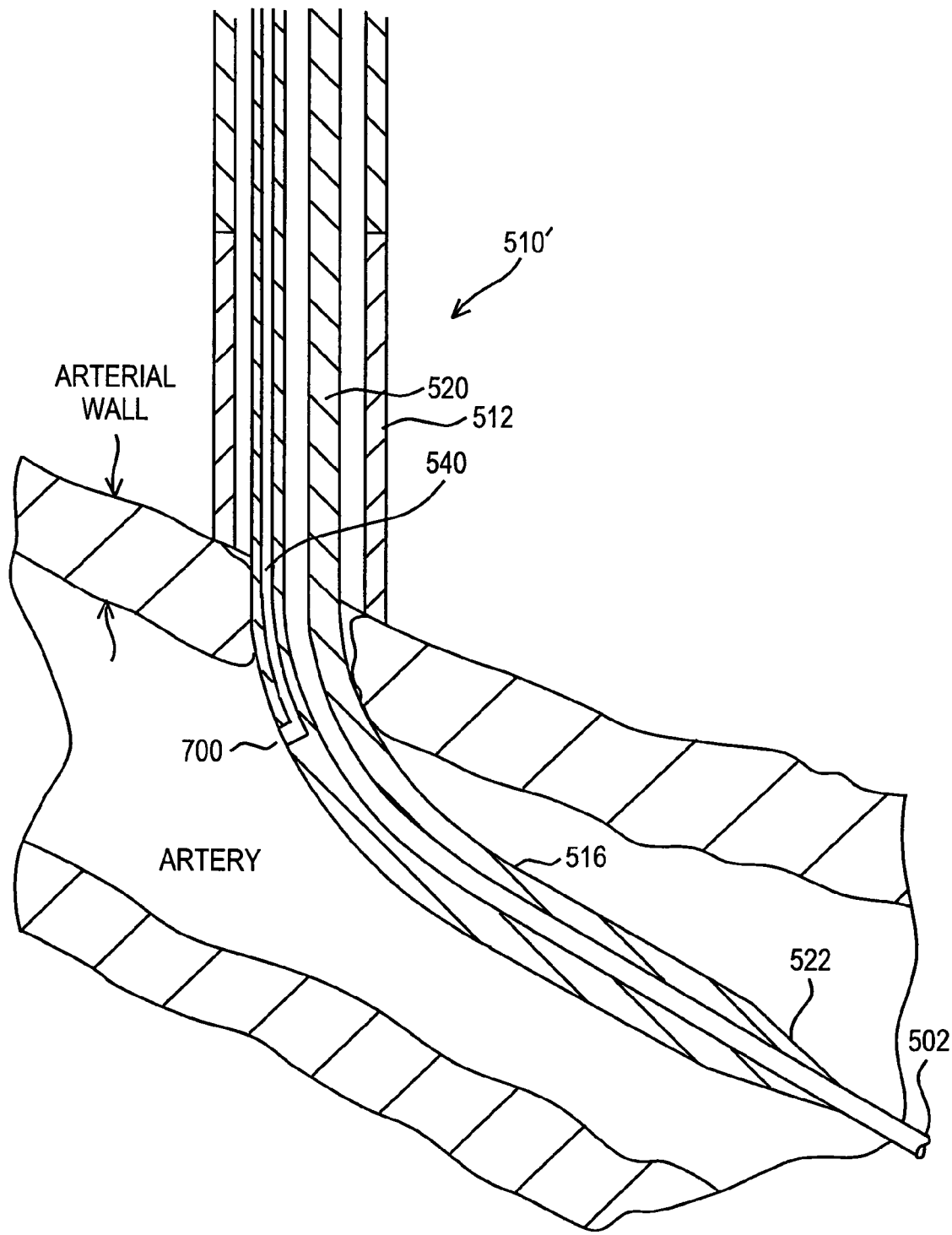
Figure 38:
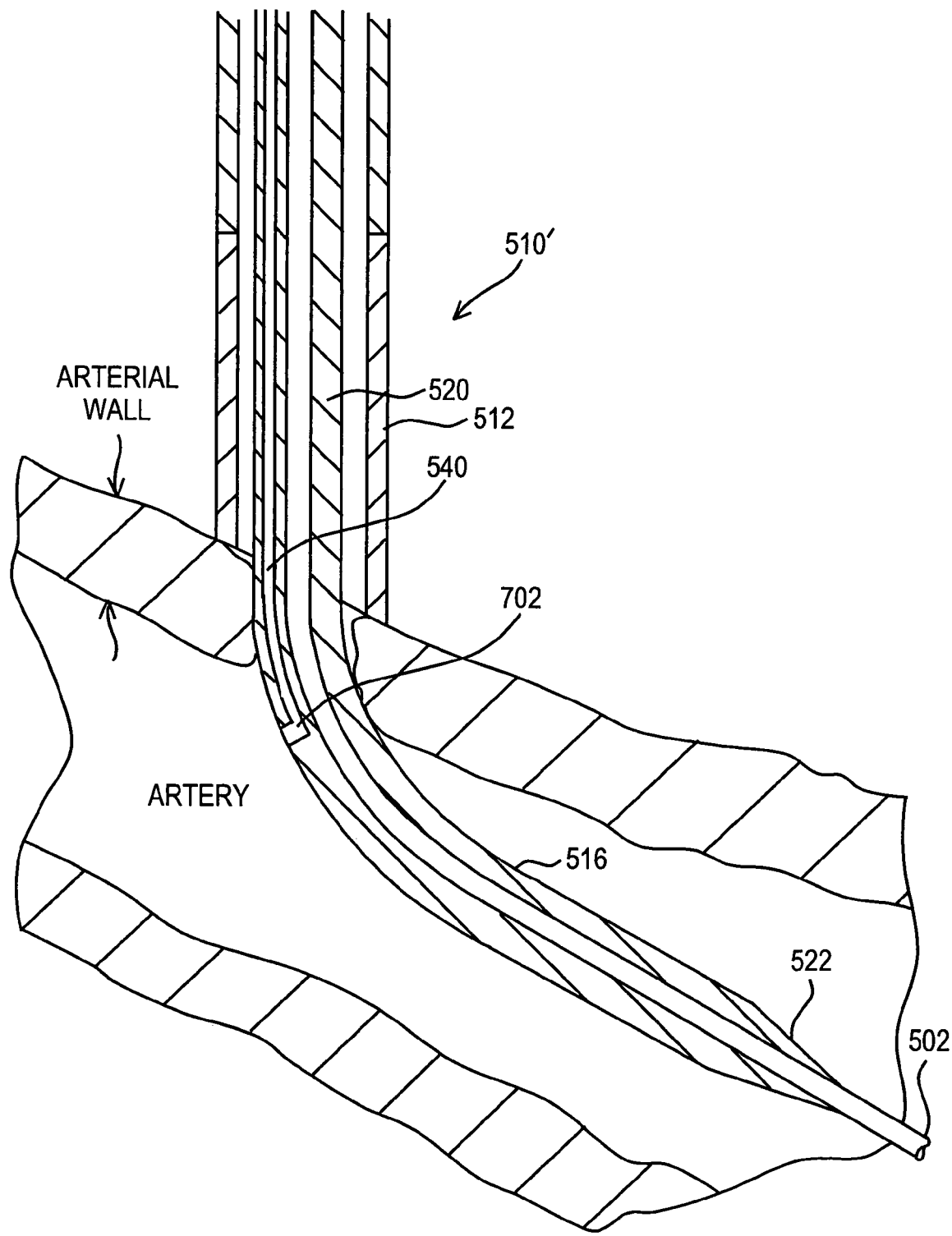

FIGS. 37 and 38 depict alternative embodiments for blood marking associated with the dilator. FIGS. 37 and 38 may be considered alternative exemplary-embodiments to the blood marking description of FIGS. 20A and 39. In FIG. 37, the BM lumen 540 includes a sensor 700 (e.g., differential pressure transducer, flow sensor, electrodes, etc.) to detect the presence of fluid or fluid flow thereon. The wiring for the sensor can be routed through the lumen 540, as shown, to transmit a signal of the pressure (or presence of fluid) at the sensor 700. In FIG. 38, an optical fiber 702 is placed in lumen 540 for direct viewing of the area around BM port to identify the presence of a vascular inner lumen.

Thus, the foregoing-described steps provide a method for identifying the depth of insertion of the transluminal device into an artery or vein based on the presence of pressurized blood internal to the vessel and the absence of pressurized blood external to the vessel. Alternatively, more than two blood marking points, lumens, and ports may be provided to further aid in determining precisely the depth of the inserted transluminal device. Furthermore, it is contemplated that the foregoing described insertion depth identifying technique may have utility in other contexts, as well, and those skilled in the art will recognize that the foregoing technique should not be limited to the context described hereinabove.

As described above, the wire guide, the stabilization loop portion, or the loop actuation wire maybe used to cause tension against the surrounding tissue, thereby aiding in approximately centering an introducer about the wound site, as well as in allowing opposing sides of the tissue surrounding the wound site to approximate one another. Also, the wire guides may be sized so that, when inserted into the artery they abut the opposing (distal) wall of the vessel so that the proximal wall at the wound site is pushed away from the distal wall to prevent the closure device from piercing the distal wall. In alternative embodiments, instead of the slits or weakened tear seams of the sheath as described herein, the sheath may instead comprise a helical structure that is expandable and contractable in the radial direction to provide the wound site stretching and expansion for the closure device that is described above. It is further contemplated that alternatives of the embodiments described above may be implemented consistent with the invention for stretching the wound site and for centrally locating procedures at the wound site. For example, in the above-described embodiments, loop portions provide a force to the wire and the guide sheath to spread the sheath outwardly and to approximate opposing portions of the wound site, as shown and described. However, in still other embodiments, the guide sheath can be formed having a biasing mechanism that forces the sheath into the opened or spread position as shown in FIGS. 31 and 36. To that end, this sheath may further comprise flexible members on either side that provide the aforementioned outwardly opposing forces on the tissue surrounding the wound site.

There are many alternatives to the foregoing description of FIGS. 18-66 that will be apparent to those skilled in the art. For example, the wire forming the loop structure described herein may be provided as a single continuous loop that is pre-threaded into the wire stabilization guides. In this case, the loop is closed by pulling on the free end of the wire. The wire may be snipped or cut so that it can be pulled free of the sheath and the wire stabilization guides. Other modifications may be made. For example, the sheath may be adapted with holding mechanisms (not shown) to hold the ends of the wire in place once the doctor has pulled on the free ends to form the loop. Still other modifications may be made. For example, instead of using wire in cooperation with the tubular wire stabilization guides to for the loop, the present invention contemplates that this arrangement can be replaced with a single elongated member (e.g. similar to the wire stabilization guide described herein) affixed to the guide sheath on opposing sides so that pulling this member forms the loop as shown in the drawings. In other words, the wire stabilization guide and wire described above may be replaced with a single member of sufficient modulus to for the loop as set forth herein. The wire described herein may comprise a tube, filament, stranded filaments, or other structures that are equivalent.

With any of the embodiments described above, the slits or weakened tear seams formed on the distal tip of the sheath (FIGS. 22A, 24A, 25A, 27-36, 40-48, and 66) permits expansion of the distal tip to cause the wire guides to stretch the wound site, as detailed above. Although the drawings have been described as having two slits or weakened tear seams on opposing sides of the sheath, the present invention is not so limited. The present invention could alternatively comprise a single slit or tear seam, where expansion of the distal tip is caused by "buckling" of the device to cause radial expansion. Alternatively, three or more slits or tear seams could be formed. In still other alternative embodiments, the sheath may generally comprise an expandable distal tip. For example, the distal tip of the sheath may include bellows or baffles to permit expansion thereof. Alternatively, the distal tip may be formed of an elastomeric material that permits expansion in the radial direction. All such alternatives are deemed within the scope of the present invention.

Still other modifications can be made. For example the stabilization guides have been described herein as being generally tubular so that wire can be threaded therethrough. However, this is only an exemplary arrangement. The stabilization guides and wire could be coupled together in other configuration, for example, sliding engagement that may comprise a tongue-and-groove coupling, dovetail coupling, or other arrangement that would permit relative motion between the stabilization guides and the wire, while still providing mechanical strength along at least one axis. Although the present invention has been described in relation to particular embodiments thereof, many other variations and modifications and other uses will become apparent to those skilled in the art.

Further Exemplary Staple and Stapler Mechanism

Figure 67:
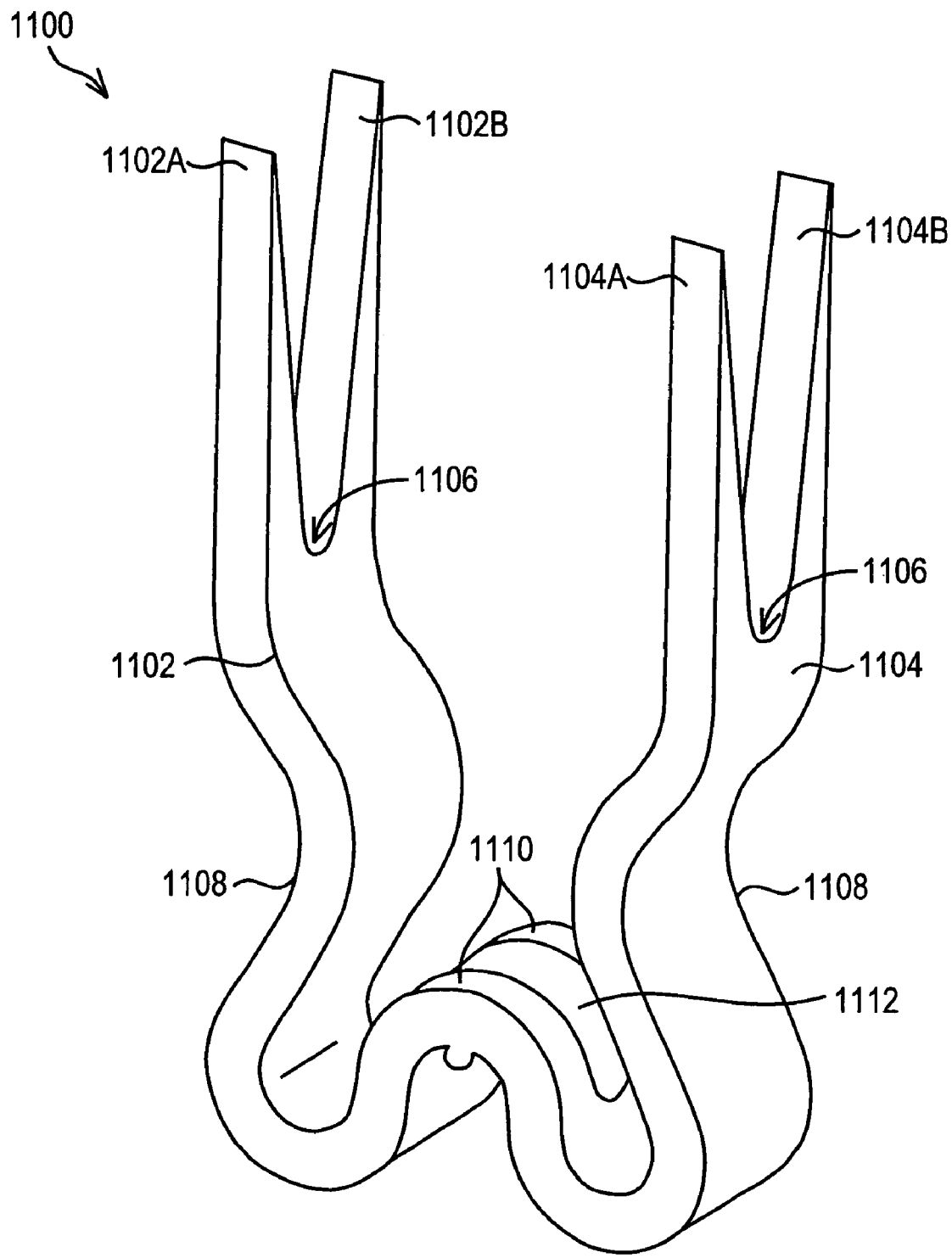
FIGS. 67-71 depict another exemplary staple and stapler mechanism according to the present invention.

FIGS. 67-71 depict another exemplary staple and stapler mechanism according to the present invention. FIG. 67 depicts an isometric view of a staple 1100 according to this exemplary embodiment. The staple 1100 includes generally parallel leg members 1102 and 1104. Each leg may include a fork section at the distal end of the leg that splits into two (or more) tissue-piercing prong portions 1102A, 1102B and 1104A, 1104B, respectively, as depicted The fork is formed at a selected location along the length of each leg 1102, 1104, and defines a tissue stop 1106 at the start of the fork. The tissue stop 1106 defines the piercing depth of the prongs, and may be placed at a desired location for a given tissue application. Alternatively, one or both of the legs may terminate into a pointed prong section, as depicted in FIG. 1. In this case, the leg may include a tissue stop extension, e.g., 32A as depicted in FIG. 3A. Each leg includes an indent 1108 defined at a desired location along the length of the leg. The particular geometry of the indent 1108 is not important, and is generally depicted having an S shape. The indents on each leg are formed at generally the same location along the length of the leg, so that the indents bend in toward one another. The indent is formed to cooperate with an mandrel associated with a stapler mechanism to expand the prongs outwardly, as will become apparent from the description below.

The legs 1102 and 1104 are joined together by tabs 1110. The tabs are formed as arcuate members that together form a pronounced arc that extends distally between the legs from the proximal ends of the legs, generally to form an inverted U shape. This shape is not required by the present invention, and a myriad of alternative shapes may be used to accomplish a staple according to the present invention. All such alternatives are deemed equivalent structures and thereby fall within the scope of the present invention The tabs are formed to define a slot 1112 between each tab, generally centered around the top of the arc, as depicted. The slot 1112 is dimensioned to permit an mandrel associated with a stapler mechanism to pass therethrough while compressing the tabs 1110 downward to close the prongs inwardly, as will become apparent from the description below.

Figure 68:
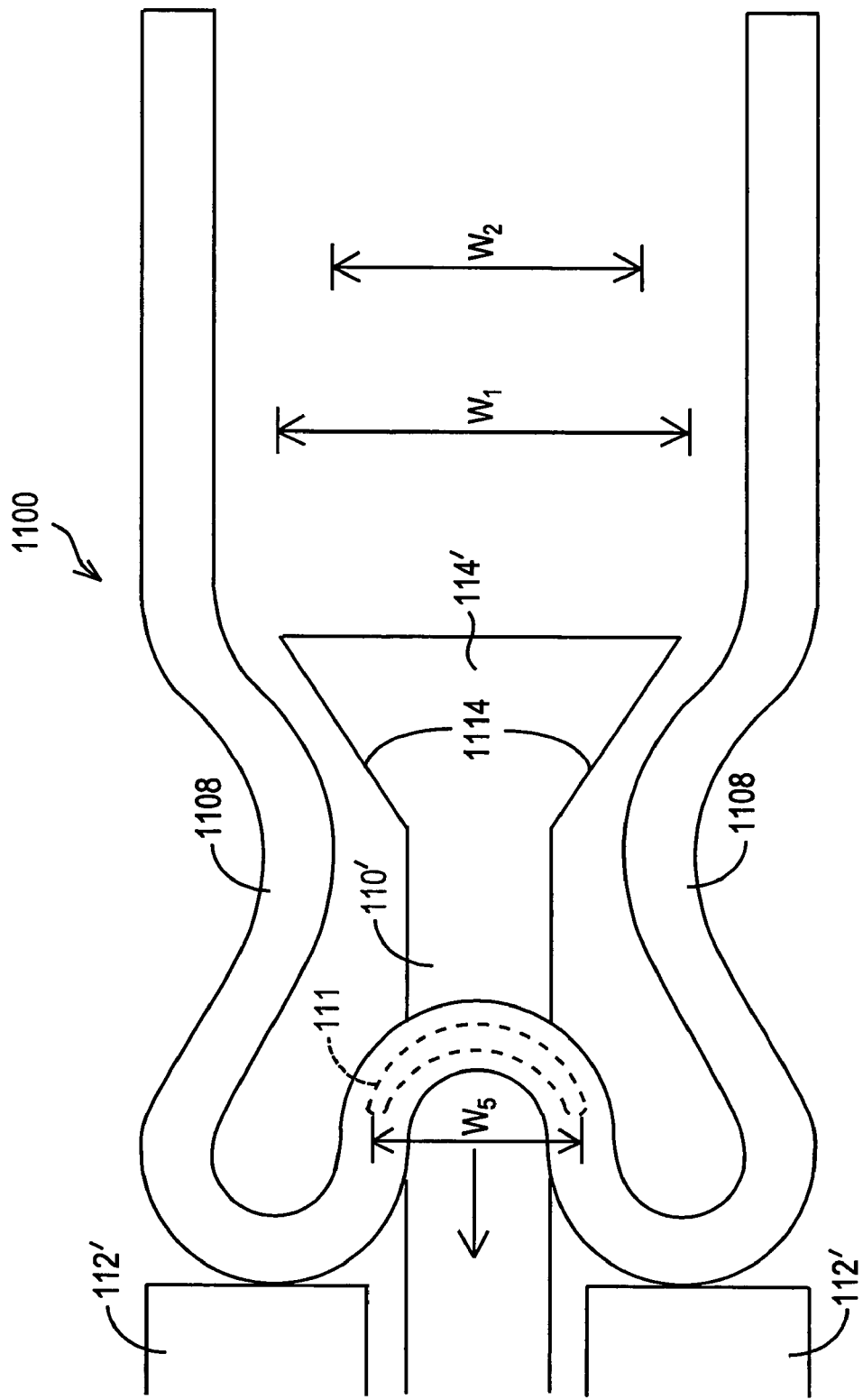
Figure 69:
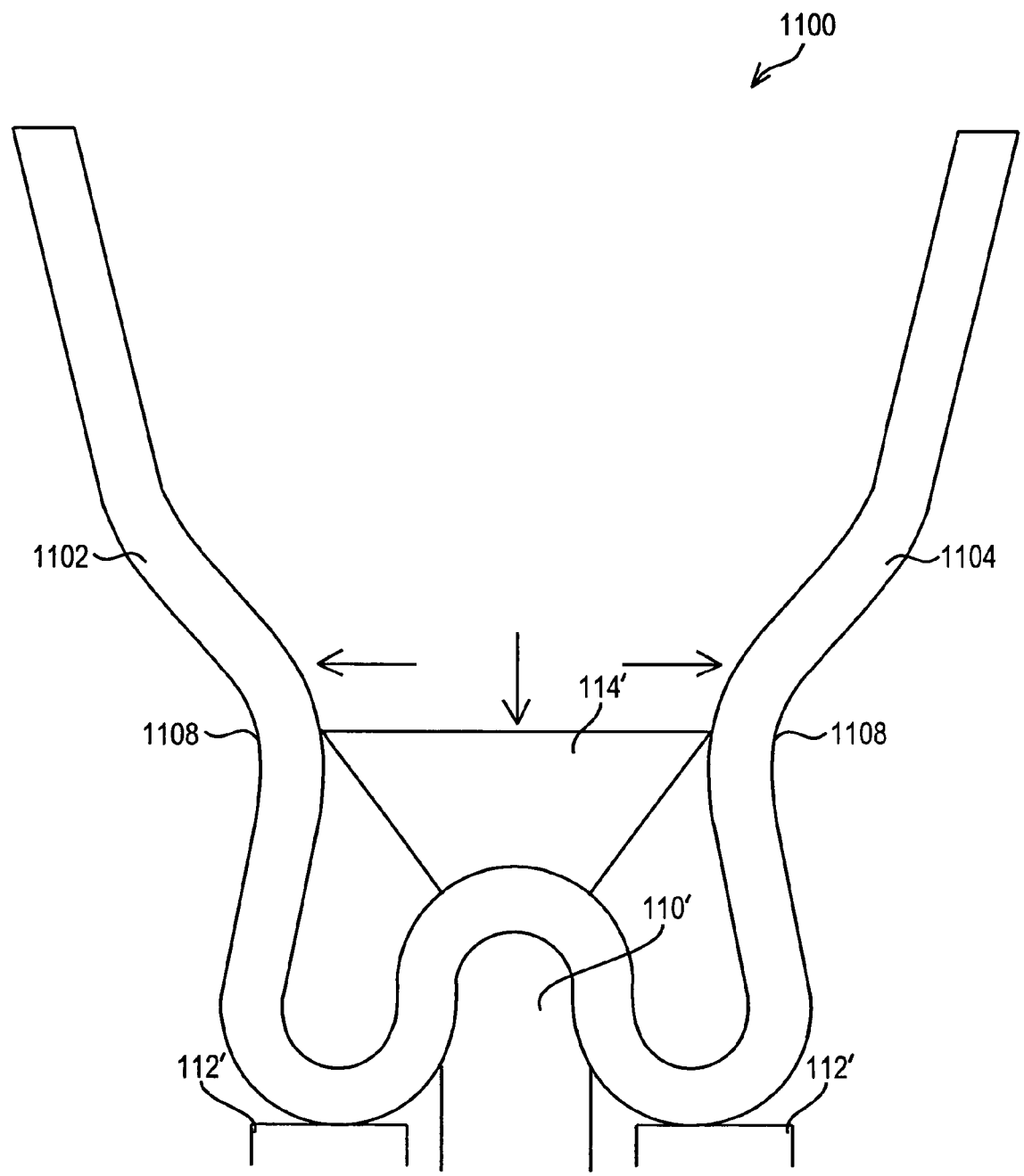
Figure 70:
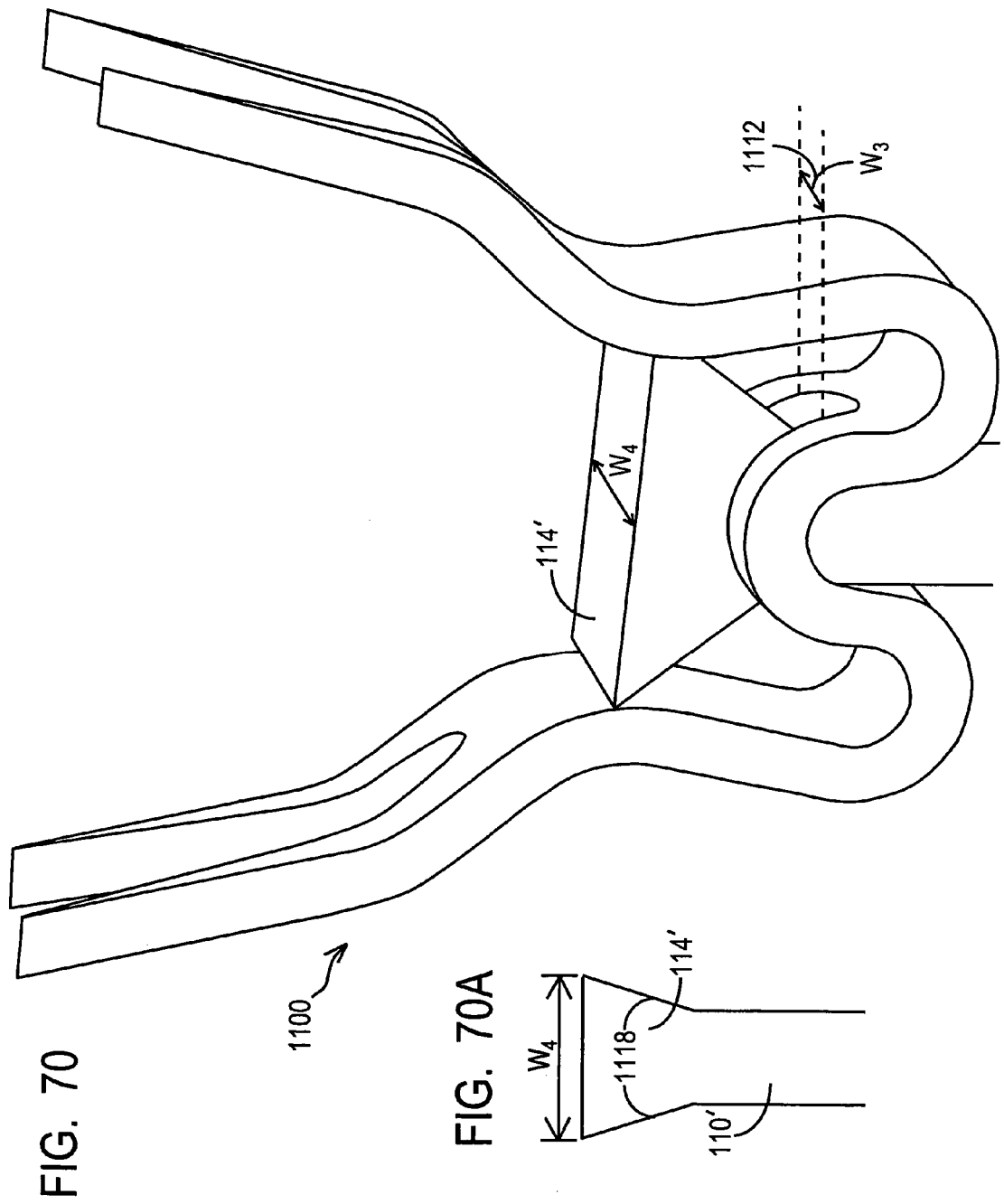

FIG. 68 depicts a cross-sectional view of the staple 1100 and the actuating tip portion of a stapler. The actuating tip (previously referred to herein as the "distal tip" section) includes an inner rod 110' slidable within an outer sleeve 112'. The rod includes a flared mandrel 114'. The mandrel 114' has flared wall sections 1114 that are dimensioned to engage the indents 1108 of the legs of the staple. The flared wall sections 1114 flare to define a width W1 of the mandrel 114'. At the area between the indents the width is W2, where W1>W2. Thus, as the mandrel slides into the sleeve 112' (or the sleeve slides over the mandrel), the relative width of the mandrel and the indents cause the prongs to expand outwardly, as depicted in FIG. 69. The maximum width of expansion is therefore set by the relative widths W1 and W2, and can be adjusted to meet a particular desired result. FIG. 70 depicts another isometric view of the staple 1100 and the mandrel 114', where the mandrel 114' has cleared the indents 1108. The mandrel has a depth, depicted as W4, that is dimensioned to fit within the width W3 of the slot 1112 defined by the tabs 1110. FIG. 70A depicts the specific cross section of the mandrel 114' showing an exemplary shape of the mandrel to define W4 in the depth dimension.

Figure 71:
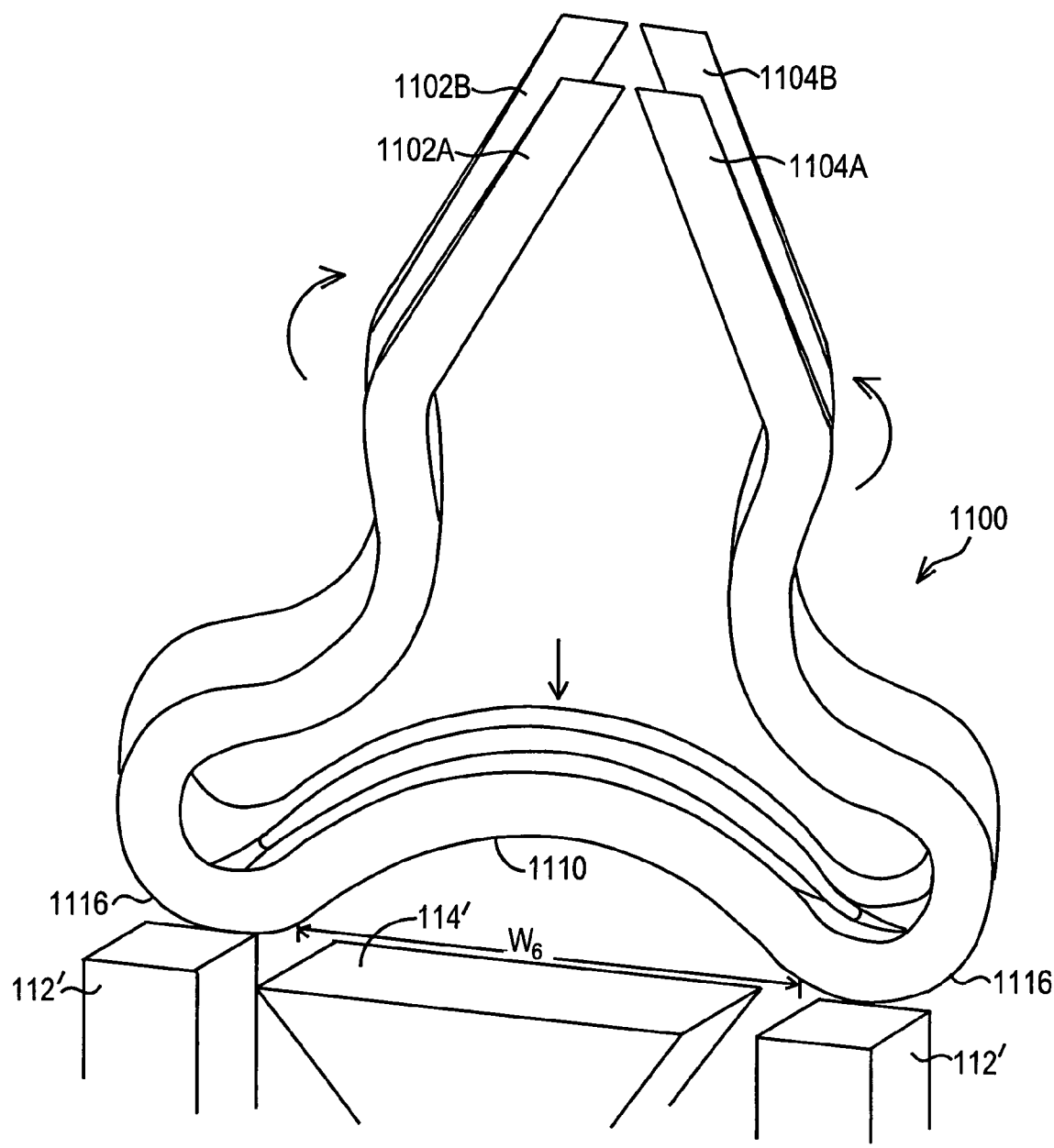

Turning again to FIG. 68, the width of the slot (1112) W5 when the staple is in the static position (i.e., before the mandrel engages the staple) is depicted. The width of the slot W5 in the static position is less than the width W1 of the mandrel. FIG. 71 depicts the staple 1100 in the closed position, as when the mandrel passes through the slot 1112. As the mandrel passes through the slot, the tabs are compressed, thereby "flattening out" the arc defined by the tabs until the width of the slot 1116 increase to permit the mandrel to pass therethrough. This width is depicted in FIG. 71 as W6. The point 1116 where the staple rests against the sleeve 112' is a pivot point and is generally where the ends of the tabs 1110 meet the ends of the leg members 1102, 1104. The opening and closing action described above generally pivots around point 1116. Further details of the stapler mechanism may be derived from the above description of FIGS. 12-17.

The legs of the staple are described herein as "generally parallel" to one another. In this application, generally parallel is to be interpreted broadly, and may include a wide range of variants from parallel, for example, +/-30 degrees off parallel with respect to one another.

What is claimed is:

1. A tissue staple system comprising:
   a tissue staple comprising two generally parallel legs having a first region defining a first width therebetween and a second region defining a second width therebetween, said second width being narrower than said first width, said legs being connected proximally by an arcuate member and each leg terminating distally in a prong, and having a tissue stop disposed on each prong and spaced from a distal tip thereof; and
   a stapler comprising a mandrel having a flared portion having a region with a third width that is wider than said second width defined by said staple, said flared portion being configured to deform said staple to expand said prongs outwardly when said second region of said staple is forced distally over said flared portion, and said stapler being configured to deform said staple to a closed configuration wherein said prongs extend toward each other.

2. A tissue staple system according to claim 1, wherein said stapler is configured to deform said staple to the closed configuration when said arcuate member is forced distally against said flared portion.

3. A tissue staple system according to claim 1, further comprising a sleeve slidably disposed relative to said mandrel, said sleeve having a distal surface capable of pushing the staple distally with respect to the flared portion.

4. A tissue staple system according to claim 1, wherein an indentation in each leg defines said second region.

5. A tissue staple system comprising:
   a tissue staple having two generally parallel legs and having a first region defining a first width between said legs and having a second region defining a second width between said legs, said second width being narrower than said first width, said legs being connected proximally by an arcuate member and each leg having a tissue stop disposed thereon and spaced from a distal tip thereof; and
   a stapler comprising a mandrel having a flared portion having a region with a third width that is wider than said second width defined by said staple, said flared portion being configured to deform said staple to splay said legs outwardly when said second region of said staple is forced distally over said flared portion, and said stapler being configured to deform said staple to a closed configuration wherein said legs extend toward each other.

6. A tissue staple system according to claim 5, wherein said stapler is configured to deform said staple to the closed configuration when said arcuate member is forced distally against said flared portion.

7. A tissue staple system according to claim 5, further comprising a sleeve slidably disposed relative to said mandrel, said sleeve having a distal surface capable of pushing said staple distally with respect to said flared portion.

8. A tissue staple system according to claim 5, wherein an indentation in each leg defines said second region.

* * * * *

UNITED STATES PATENT AND TRADEMARK OFFICE
CERTIFICATE OF CORRECTION

| | | |
|---|---|---|
| PATENT NO. | : 7,597,706 B2 | Page 1 of 1 |
| APPLICATION NO. | : 10/899911 | |
| DATED | : October 6, 2009 | |
| INVENTOR(S) | : Kanner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 659 days.

Signed and Sealed this

Twenty-eighth Day of September, 2010

David J. Kappos
*Director of the United States Patent and Trademark Office*